US012733922B2

(12) United States Patent
Heneveld et al.

(10) Patent No.: US 12,733,922 B2
(45) Date of Patent: Sep. 15, 2026

(54) MULTI-FUNCTION SYSTEMS, APPARATUS AND METHODS FOR APPROXIMATING, LIGATING AND FIXATING SOFT TISSUE

(71) Applicant: Passer Stitch, LLC, Henderson, NV (US)

(72) Inventors: Scott Heneveld, Whitmore, CA (US); John Valadez, Agua Dulce, CA (US); Christopher Morris, Santa Clarita, CA (US); Justin Anderson, Henderson, NV (US); Brad Topper, Santa Clarita, CA (US); Jeffrey Sonntag, South Bend, IN (US)

(73) Assignee: Passer Stitch, LLC, Henderson, NV (US)

( * ) Notice: Subject to any disclaimer, the term of this patent is extended or adjusted under 35 U.S.C. 154(b) by 0 days.

(21) Appl. No.: 19/634,724

(22) Filed: Mar. 31, 2026

(65) Prior Publication Data

US 2026/0224214 A1 Aug. 6, 2026

Related U.S. Application Data

(63) Continuation-in-part of application No. 19/330,007, filed on Sep. 16, 2025, now Pat. No. 12,616,463,
(Continued)

(51) Int. Cl.
*A61B 17/04* (2006.01)
*A61B 17/06* (2006.01)
(Continued)

(52) U.S. Cl.
CPC .............................. *A61B 17/0469* (2013.01); *A61B 2017/00367* (2013.01); *A61B 2017/047* (2013.01);
(Continued)

(58) Field of Classification Search
CPC ........... A61B 17/0469; A61B 17/0483; A61B 17/0482; A61B 17/06004;
(Continued)

(56) References Cited

U.S. PATENT DOCUMENTS 7,972,344 B2 7/2011 Murray et al.
8,177,796 B2 5/2012 Akyuz et al.
(Continued)

*Primary Examiner* — Tuan V Nguyen
(74) *Attorney, Agent, or Firm* — Francis Law Group

(57) ABSTRACT

A system for passing suture into and through soft tissue that includes a multi-function jaw mechanism, and a needle adapted to engage a suture and pierce into the soft tissue. The multi-function jaw mechanism adapted to capture sutures, soft tissue and surgical instruments and devices, provide highly reliable suture loading and retrieval with minimal visual guidance, and measure stitch placement positions in the soft tissue in a confined surgical site for accurate and precise provision of complex stitch patterns. The system also includes system control means for synchronizing articulation of the multi-function jaw mechanism, articulation of the needle, and engagement of the suture by the needle and release of the suture therefrom.

28 Claims, 54 Drawing Sheets

Related U.S. Application Data which is a continuation-in-part of application No. 19/271,062, filed on Jul. 16, 2025, now Pat. No. 12,490,973, which is a continuation of application No. 18/623,903, filed on Apr. 1, 2024, now Pat. No. 12,390,213.

(60) Provisional application No. 63/766,960, filed on Mar. 4, 2025, provisional application No. 63/602,605, filed on Nov. 26, 2023, provisional application No. 63/456,513, filed on Apr. 2, 2023.

(51) Int. Cl.
*A61B 17/00* (2006.01)
*A61B 17/29* (2006.01)

(52) U.S. Cl.
CPC ................. *A61B 2017/2925* (2013.01); *A61B 2017/2926* (2013.01)

(58) Field of Classification Search
CPC ...... A61B 17/06066; A61B 2017/2936; A61B 2017/2933; A61B 2017/2934; A61B 2017/2944; A61B 2017/294
See application file for complete search history.

(56) References Cited

U.S. PATENT DOCUMENTS

| | | | | |
|---|---|---|---|---|
| 8,460,318 | B2 | 6/2013 | Murray et al. | |
| 10,383,621 | B2 | 8/2019 | Gregoire et al. | |
| 12,076,003 | B2 | 9/2024 | Otrando et al. | |
| 2011/0118760 | A1* | 5/2011 | Gregoire ............ | A61B 17/0469 606/145 |
| 2017/0172565 | A1 | 6/2017 | Heneveld | |
| 2017/0333030 | A1* | 11/2017 | Bourland, III ....... | A61B 17/062 |
| 2018/0235601 | A1 | 8/2018 | Malkowski et al. | |
| 2019/0167257 | A1 | 6/2019 | Heneveld | |
| 2020/0093479 | A1 | 3/2020 | Murillo et al. | |
| 2020/0360012 | A1 | 11/2020 | Heneveld | |
| 2021/0000463 | A1 | 1/2021 | Murillo et al. | |

* cited by examiner 100
114a
112
110
114b
108
104
103
R
106
102

MULTI-FUNCTION SYSTEMS, APPARATUS AND METHODS FOR APPROXIMATING, LIGATING AND FIXATING SOFT TISSUE

CROSS-REFERENCES TO RELATED APPLICATIONS

This application is a continuation-in-part of U.S. application Ser. No. 19/330,007, filed on Sep. 16, 2025, which claims the benefit of U.S. Provisional Application No. 63/766,960, filed on Mar. 4, 2025, and is a continuation-in-part of U.S. application Ser. No. 19/271,062, filed on Jul. 16, 2025, now U.S. Pat. No. 12,490,973, which is a continuation of U.S. application Ser. No. 18/623,903, filed on Apr. 1, 2024, now U.S. Pat. No. 12,390,213, which claims the benefit of U.S. Provisional Application No. 63/456,513, filed on Apr. 2, 2023, and U.S. Provisional Application No. 63/602,605, filed on Nov. 26, 2023.

FIELD OF THE INVENTION

The present invention relates to multi-function systems, apparatus and associated methods for approximating, ligating and fixating soft tissue; particularly, soft tissue that is accessed via an endoscopic procedure.

BACKGROUND OF THE INVENTION

As is well established, approximating, ligating and fixating soft tissue, such as fascia, muscles, ligaments and tendons, is a fundamental aspect of many surgical procedures. The process of approximating, ligating and fixating soft tissue often involves passing suture through the soft tissue with a suture passing system or device.

Various suture passing systems and devices have thus been developed and employed to pass suture through soft tissue, such as the device disclosed in U.S. Pat. No. 10,383,621 to Gregoire, et al. The Gregoire, et al. device, as well as most conventional suture passing devices, include an elongated shaft and a low-profile distal jaw mechanism that is adapted to be advanced into a surgical site via access cannula in minimally invasive surgical procedures. The jaw mechanism typically comprises top and bottom jaw members that are adapted to capture and position the soft tissue for passage of a suture therethrough.

Conventional suture passing systems and devices also typically comprise means for positioning and capturing a portion of a suture and retracting the suture into the device after it is passed through soft tissue. Such means typically comprises a bendable needle having a suture capture end that is advanced into and through elongated shaft of the device and through a distal opening in the bottom jaw member.

Several conventional suture passing systems also include suture retainment means that is adapted and configured to retain a portion of suture (usually in a top jaw member of a jaw mechanism) after the portion of suture has been drawn through soft tissue for manipulation by the system in a surgical site, e.g., forming a particular suture pattern.

Although many conventional suture passing systems can effectively be employed to pass suture into and through soft tissue in a surgical site and retain a portion of the suture after passage through soft tissue, there are numerous drawbacks and disadvantages associated with the use of conventional suture passing systems and associated devices to approximate, ligate and fixate soft tissue.

Major drawbacks and disadvantages associated with most conventional suture passing systems include difficultly manipulating soft tissue in a confined surgical site, cumbersome operation and, often complicated and sight dependent, suture loading procedures, and difficulty manipulating and retrieving suture in a confined surgical site.

A further major drawback and disadvantage associated with conventional suture passing systems is that such systems are typically devoid of any means for effectively engaging and capturing sutures and soft tissue or a portion thereof (prior to or after passing suture therethrough), and other soft tissue and surgical instruments and devices in a surgical site during a surgical procedure.

Yet another major drawback and disadvantage associated with conventional suture passing systems is that such systems are also devoid of any means for stitch measurement and placement in soft tissue to accurately produce complex stitch patterns, such as modified Mason-Allen stitch patterns. The conventional systems solely rely on visual guidance by an operator to produce common and complex stitch patterns, which significantly limits a surgeon's ability to consistently provide precise stitch patterns.

Difficulties with manipulation of suture and soft tissue in a confined surgical site and the absence of any means for measuring stitch placement positions in soft tissue also limits the types of soft tissue that can be approximated and fixated by the conventional suture passing systems.

A further drawback and disadvantage associated with conventional suture passing systems is that such systems are also typically devoid of any means for protecting the needles employed therewith from breakage in a surgical site during a surgical procedure, e.g., breakage resulting from contact with hard tissue, such as bone.

A further drawback and disadvantage associated with conventional suture passing systems is that such systems typically have a limited life cycle due to needle wear and fatigue.

There is thus a need for improved suture passing systems, apparatus and methods that substantially reduce or eliminate the disadvantages and drawbacks associated with conventional suture passing systems, apparatus and methods.

It is thus an object of the present invention to provide improved suture passing systems, apparatus and methods that substantially reduce or eliminate the disadvantages and drawbacks associated with conventional suture passing systems, apparatus and methods.

It is another object of the present invention to provide improved suture passing systems, apparatus and methods systems that can be readily employed to effectively grasp, approximate, ligate, fixate soft tissue and soft tissue structures in a confined surgical site.

It is another object of the present invention to provide improved suture passing systems, apparatus and methods that can be readily employed to pass suture into and through soft tissue and soft tissue structures without collateral damage to extraneous soft tissue and bone structures.

It is another object of the present invention to provide improved suture passing systems, apparatus and methods that provide an enhanced degree of control of soft tissue and soft tissue structure engagement, needle articulation and suture manipulation by an operator with minimal complexity.

It is another object of the present invention to provide improved suture passing systems, apparatus and methods that enable an operator to load suture with greater ease and efficiency compared to conventional suture passing systems.

It is another object of the present invention to provide improved suture passing systems, apparatus and methods that provide enhanced suture manipulation in a confined surgical site with minimal visual guidance.

It is another object of the present invention to provide improved suture passing systems, apparatus and methods that enable an operator to precisely measure stitch placement locations in soft tissue and soft tissue structures in a confined surgical site for accurate and precise provision of complex stitch patterns.

It is another object of the present invention to provide improved suture passing systems, apparatus and methods that can be readily employed to effectively capture and engage soft tissue, soft tissue structures, sutures and surgical instruments and devices within a confined surgical site.

It is another object of the present invention to provide improved suture passing systems, apparatus and methods that provide enhanced needle durability over thousands of cycles of suture passing in and through soft tissue and soft tissue structures.

It is another object of the present invention to provide improved suture passing systems and apparatus that can be readily employed to endure multiple use cycles with limited impact on suture passing efficacy.

It is another object of the present invention to provide improved suture passing systems, apparatus and methods that prevent needle breakage in a surgical site during a surgical procedure.

It is another object of the present invention to provide multi-function jaw mechanisms and suture passing systems, apparatus and methods employing same that (i) enable an operator to load suture with greater ease and efficiency compared to conventional suture passing systems, and (ii) provide enhanced suture manipulation and retrieval in a confined surgical site with minimal visual guidance, and (iii) enable an operator to precisely measure stitch placement locations in soft tissue and soft tissue structures in a confined surgical site for accurate and precise provision of complex stitch patterns, such as modified Mason-Allen stitch patterns, and (iv) can be readily employed to effectively capture and engage soft tissue, soft tissue structures and surgical instruments within a confined surgical site, and (v) provide enhanced needle durability over thousands of cycles of suture passing in and through soft tissue and soft tissue structures, and (vi) prevent needle breakage in a surgical site during a surgical procedure.

SUMMARY OF THE INVENTION

The present invention is directed to apparatus, systems and methods for grasping and capturing (or retaining) sutures, soft tissue and structures (referred to herein as "soft tissue") and surgical instruments (and devices), and approximating, ligating and fixating soft tissue.

In one embodiment of the invention, there is thus provided a system for grasping and capturing (or retaining) sutures, soft tissue and surgical instruments (and devices), and approximating, ligating and fixating soft tissue, the system comprising a needle and a multi-function jaw mechanism, the needle comprising a tissue piercing distal end configured and adapted to releasably engage a suture and pierce into and through soft tissue with the suture the releasably engaged thereto; and a multi-function jaw mechanism adapted to receive and cooperate with the needle, wherein the needle is allowed to linearly articulate with respect to the jaw mechanism, the multi-function jaw mechanism comprising top and bottom jaw members, the top jaw member adapted to axially articulate with respect to the bottom jaw member, whereby the jaw mechanism is adapted to transition from a fully open jaw configuration, wherein the top and bottom jaw members provide an open jaw mechanism region, to a closed jaw configuration, the open jaw mechanism region configured to receive a suture and at least first soft tissue therein, the multi-function jaw mechanism further adapted to transition to a partially open configuration from the fully open jaw configuration and the closed jaw configuration, the partially open jaw configuration similarly configured to the receive the suture and the at least first soft tissue therein, the top jaw member comprising a top jaw member longitudinal axis, a top jaw member proximal end and a top jaw member distal end, the bottom jaw member comprising a bottom jaw member proximal end and a bottom jaw member distal end, the top jaw member distal end disposed proximate the bottom jaw member distal end when the multi-function jaw mechanism is in the closed jaw configuration, the top jaw member distal end comprising a first suture-tissue engagement region, the first suture-tissue engagement region comprising a top jaw member tissue engagement region, a top jaw member suture engagement region and a recessed region disposed between the top jaw member tissue engagement region and the top jaw member suture engagement region, the top jaw member suture engagement region extending proximally from the top jaw member distal end no greater than 4.0 mm, the top jaw member tissue engagement region comprising a first tissue engaging surface adapted to grasp second soft tissue, the top jaw member suture engagement region comprising a first suture engaging surface adapted to removably engage the suture, the bottom jaw member distal end comprising a second suture-tissue engagement region, the second suture-tissue engagement region comprising a bottom jaw member tissue engagement region and a bottom jaw member suture engagement region, the bottom jaw member tissue engagement region comprising a second tissue engaging surface-adapted to grasp the second soft tissue, the bottom jaw member suture engagement region comprising a second suture engaging surface adapted to removably engage the suture, the first suture-tissue engagement region of the top jaw member positioned relative to the second suture-tissue engagement region of the bottom jaw member, whereby, when the multi-function jaw mechanism is in the closed jaw configuration, the first suture-tissue engagement region of the top jaw member and the second suture-tissue engagement region of the bottom jaw member are aligned and form a jaw mechanism suture-tissue engagement region, wherein at least the top jaw member suture engagement region and the bottom jaw member suture engagement region are in contact, the first suture-tissue engagement region of the top jaw member and the second suture-tissue engagement region of the bottom jaw member further forming a jaw mechanism suture-tissue capture region when the multi-function jaw mechanism is in the partially open jaw configuration, wherein, when the suture is received in the open jaw mechanism region and/or jaw mechanism suture-tissue capture region formed by the top and bottom jaw members of the multi-function jaw mechanism and the multi-function jaw mechanism is in the closed jaw configuration, the top jaw member suture engagement region and the bottom jaw member suture engagement region jointly grasp and retain the suture in the jaw mechanism suture-tissue engagement region.

In a preferred embodiment, when the second soft tissue is received in the open jaw mechanism region and/or jaw mechanism suture-tissue capture region formed by the top and bottom jaw members of the multi-function jaw mechanism and the jaw mechanism is in the closed jaw configuration, the top jaw member tissue engagement region and the bottom jaw member tissue engagement region jointly grasp and retain at least a portion of the second soft tissue in the jaw mechanism suture-tissue engagement region between the top jaw member and the bottom jaw member.

In a preferred embodiment, when a surgical instrument or device is received in open jaw mechanism region and/or jaw mechanism suture-tissue capture region formed by the top and bottom jaw members of the multi-function jaw mechanism and the jaw mechanism is in the closed jaw configuration, the top jaw member tissue engagement region and the bottom jaw member tissue engagement region similarly jointly grasp and retain the surgical instrument and/or device in the jaw mechanism suture-tissue engagement region between the top jaw member and the bottom jaw member.

In a preferred embodiment, the top jaw member suture engagement region comprises a width no greater than approximately 4.0 mm.

In a preferred embodiment, the jaw mechanism suture-tissue engagement region extends proximally less than 20% of the length of the top jaw member or 20% of the length of the bottom jaw member from the distal end thereof when the jaw mechanism in in the closed configuration.

In a preferred embodiment, the system further comprises a retractable suture control ribbon adapted to control access of the suture into the open jaw mechanism region of the jaw mechanism, the releasable engagement of the suture by the needle, and release of the suture by the needle.

In a preferred embodiment, the system further comprises system control means for synchronizing the axial articulation of the top jaw member, the linear articulation of the needle, the access of the suture into the open jaw mechanism region of the jaw mechanism, the releasable engagement of the suture by the needle, and the release of the suture by the needle.

In a preferred embodiment, the multi-function jaw mechanism further comprises means for measuring a stitch placement location in the soft tissue when the soft tissue is advanced into the open jaw mechanism region of the multi-function jaw mechanism.

In a preferred embodiment, the multi-function jaw mechanisms of the invention described herein and, thereby, suture passing systems employing the multi-function jaw mechanisms provide, among several seminal features, (i) uncomplicated and highly reliable suture loading with minimal visual guidance, (ii) enhanced suture manipulation and retrieval in a confined surgical site with minimal visual guidance, (iii) precise and consistent stitch measurement and placement in soft tissue in a confined surgical site for accurate and precise provision of complex stitch patterns, such as modified Mason-Allen stitch patterns, and (iv) highly effective means for engaging, capturing sutures, soft tissue (and soft tissue structures) and surgical instruments and devices within a confined surgical site.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 26Y1 is a perspective view of one embodiment of a distal needle wear resistance member, in accordance with the invention;

FIG. 26Y2 is a perspective view of one embodiment of a proximal needle wear resistance member, in accordance with the invention;

DETAILED DESCRIPTION OF THE PREFERRED EMBODIMENT

Figure 1A:
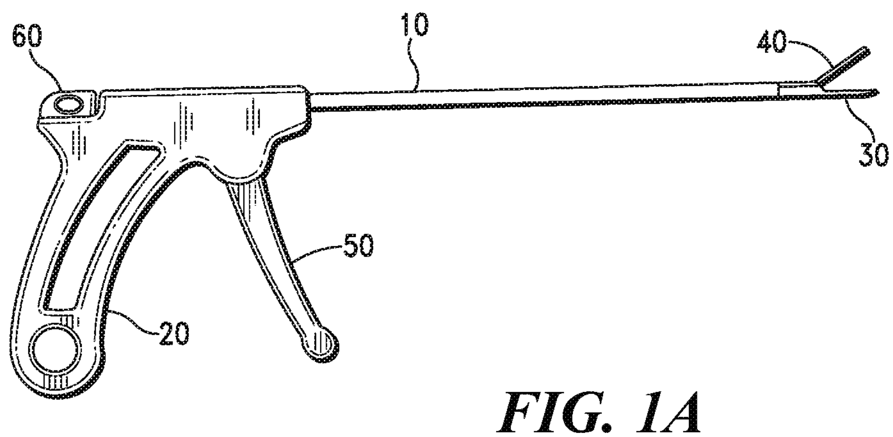
FIGS. 1A-1C are side plan views of an embodiment of a suture passing system in various stages of deployment, in accordance with the invention.

Before describing the present invention in detail, it is to be understood that this invention is not limited to particularly exemplified systems, apparatus, structures or methods as such may, of course, vary. Thus, although a number of systems, apparatus, structures and methods similar or equivalent to those described herein can be used in the practice of the present invention, the preferred systems, apparatus, structures and methods are described herein.

It is also to be understood that, although the present invention is described and illustrated in connection with endoscopic procedures, the invention is not limited to such procedures. According to the invention, the systems, apparatus and methods of the invention can also be employed in connection with a multitude of other surgical procedures, including open surgical procedures.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms “a”, “an” and “the” include plural referents unless the content clearly dictates otherwise. Thus, for example, reference to “an active” includes two or more such actives and the like.

Further, ranges can be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as “approximately” that particular value in addition to the value itself. For example, if the value “10” is disclosed, then “approximately 10” is also disclosed. It is also understood that when a value is disclosed that “less than or equal to” the value, “greater than or equal to the value” and possible ranges between values are also disclosed, as appropriately understood by the skilled artisan. For example, if the value “10” is disclosed then “less than or equal to 10”, as well as “greater than or equal to 10” is also disclosed.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The words used in the description to describe the invention and its various embodiments are to be understood not only in the sense of their commonly defined meanings, but to include by special definition in this specification the generic structure, material or acts of which they represent a single species.

Definitions

The terms “tissue”, “soft tissue” and “biological tissue” are used interchangeably herein, and mean and include mammalian biological tissue, such as, by way of example, human abdominal tissue.

The term “biological cavity”, as used herein, means and includes any cavity or space in a mammalian tissue structure.

The term “surgical site”, as used herein, means and includes any space or region in a mammalian tissue structure where a surgical procedure is conducted.

The terms “endoscopy” and “endoscopic procedure”, as used herein, mean and include any minimally invasive surgical procedure conducted through at least one opening in a subject’s body, including, but not limited to arthroscopy, laparoscopy, hysteroscopy and the like.

The terms “system”, “apparatus” and “device” are used interchangeably herein, and mean and include an assembly or component thereof that is configured and adapted to facilitate approximation, ligation and/or fixation of soft tissue.

The term “finite” as used in conjunction with grasping and/or engaging a suture and soft tissue with the systems, apparatus and devices of the invention, means and includes a definitive, partial portion of a suture; particularly a fine suture, e.g., a 0.01 mm suture.

The term “pharmacological agent”, as used herein, means and includes an active agent, compound, composition or mixture thereof, including its formulation, which provides some therapeutic, often beneficial, effect. This includes any physiologically or pharmacologically active substance (or composition comprising same) that produces a localized or systemic effect or effects in animals, including warm-blooded mammals.

The term “pharmacological agent” thus means and includes, without limitation, antibiotics, anti-microbial agents, anti-viral agents, analgesic agents, anti-inflammatory agents, anti-neoplastic agents, anti-spasmodic agents, anticoagulant agents and agents the modulate proliferation and growth of tissue.

The term “pharmacological agent” thus means and includes, without limitation, the following antibiotics and compositions comprising same: penicillin, carboxypenicillins, such as ticarcillin, tetracyclines, such as minocycline, gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin and rifampin.

The term “pharmacological agent” thus also means and includes, without limitation, the following anti-inflammatory agents and compositions comprising same: dexamethasone, betamethasone, prednisone, prednisolone, methylprednisolone sodium succinate, methylprednisolone, cortisone, ketorolac, diclofenac and ibuprofen.

The term “pharmacological agent” thus also means and includes, without limitation, the following metal-based antimicrobials and compositions comprising same: silver particles, copper particles, cobalt particles, nickel particles, zinc particles, zirconium particles, molybdenum particles, lead particles and mixtures thereof.

The term “therapeutically effective”, as used herein, means that the amount of the “pharmacological agent” administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms “one embodiment”, “one aspect”, and “an embodiment” and “an aspect”, as used herein, means that a particular feature, structure, or characteristic described in connection with the embodiment may be included in at least one embodiment and not that any particular embodiment is required to have a particular feature, structure or characteristic described herein unless set forth in the claim.

The phrase “in one embodiment” or similar phrases employed herein do not limit the inclusion of a particular element of the invention to a single embodiment. The element may thus be included in other, or all embodiments discussed herein.

The phrase “in one configuration” or similar phrases employed herein do not necessarily refer to the same configuration and, unless specifically stated, do not limit the inclusion of a particular element of the invention to a single configuration. The element may thus be included in other, or all configurations discussed herein.

The term “substantially”, as used herein, means and includes the complete or nearly complete extent or degree of an action, characteristic, property, state, structure, item, or result to function as indicated. For example, an object that is “substantially” enclosed would mean that the object is either completely enclosed or nearly completely enclosed. The exact allowable degree of deviation from absolute completeness may in some cases depend on the specific context, such that enclosing nearly all of the length of a lumen would be substantially enclosed, even if the distal end of the structure enclosing the lumen had a slit or channel formed along a portion thereof.

Use of the term “substantially” is equally applicable when used in a negative connotation to refer to the complete or near complete lack of an action, characteristic, property, state, structure, item, or result. For example, structure which is “substantially free of” a bottom would either completely lack a bottom or so nearly completely lack a bottom that the effect would be effectively the same as if it completely lacked a bottom.

The term “comprise” and variations of the term, such as “comprising” and “comprises,” means “including, but not limited to” and is not intended to exclude, for example, other components, elements or steps.

The terms “patient” and “subject” are used interchangeably herein, and mean and include warm-blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present disclosure is directed to apparatus, systems and methods for grasping, approximating, ligating and/or fixating soft tissue; particularly, soft tissue that is accessed via an endoscopic procedure.

As is well known in the art, sutures are often employed in both open and endoscopic surgical procedures to approximate, ligate and fixate soft tissue or otherwise treat tissue. Generally, suture needles with attached suture are grasped either manually or by forceps and passed through the surgical site to approximate, ligate and fixate soft tissue.

Although such surgical procedures are relatively uncomplicated in open surgery procedures where most suture sites are readily accessible, surgeons must often use auxiliary devices to grasp the suture, i.e. strands thereof, and pass the suture through desired soft tissue in endoscopic procedures where access to a desired suture site is not readily available.

Referring now to FIG. 1A, there is illustrated one embodiment of a suture passing system of the present invention that is adapted to pass suture through soft tissue. As illustrated in FIG. 1A, the suture passing system comprises an elongated tubular body 10, a hand grip 20, a tip 30, a jaw mechanism 40, an actuator 50 and a needle assembly 60.

Figure 1B:
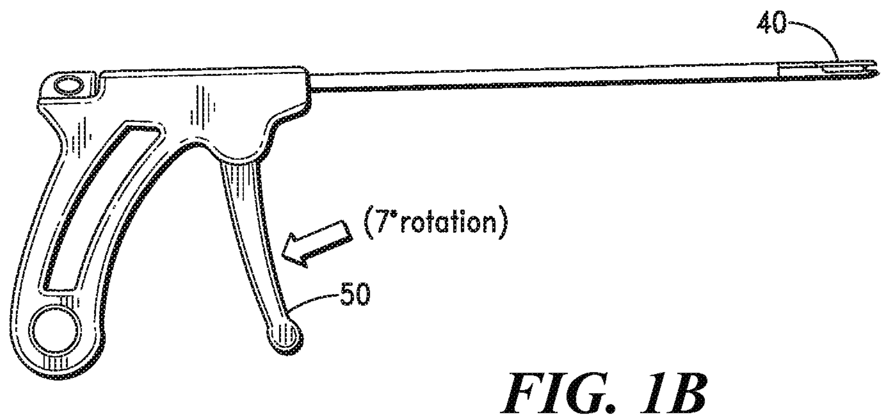
Figure 1C:
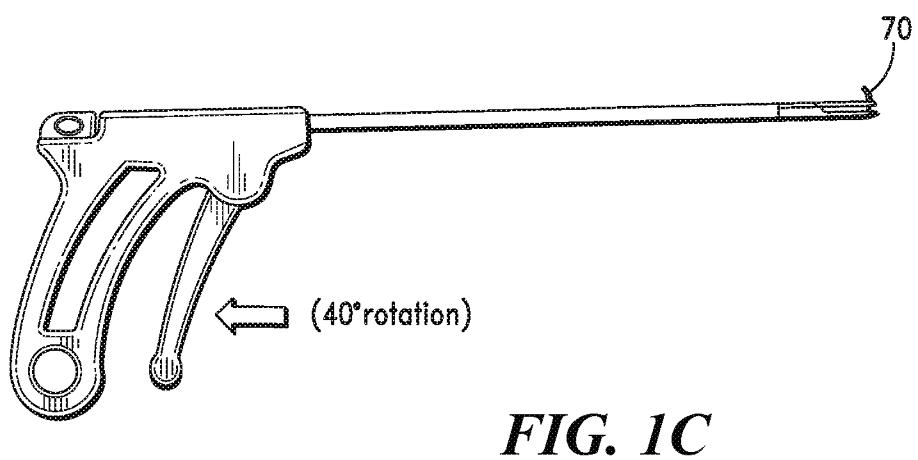

According to the invention, with actuator 50, a surgeon can seize and maintain soft tissue by movement of the jaw mechanism 40 against tip 30, as shown in FIG. 1B. Using actuator 50, a surgeon can also deploy a tubular needle 70 carrying a suture 71 through soft tissue, as shown in FIG. 1C and described below.

Figure 2A:
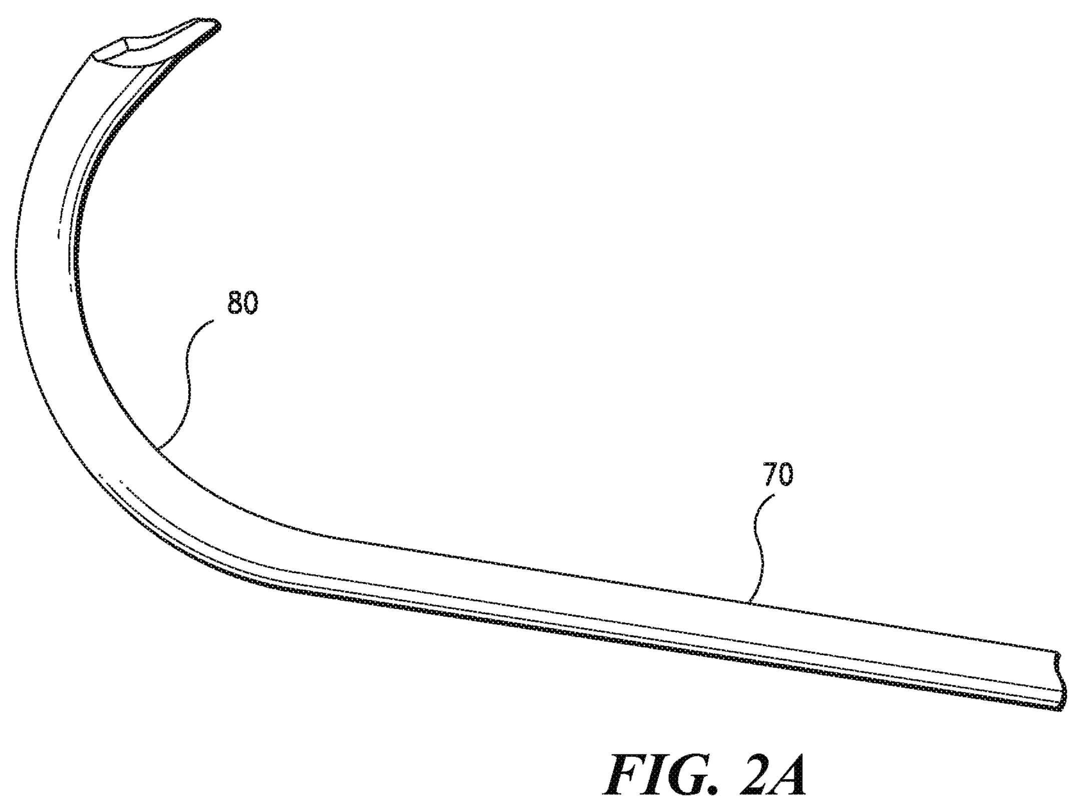
FIG. 2A is a partial side plan view of a notch-less tubular needle comprising a preformed memory shape, in accordance with the invention.

Referring now to FIG. 2A, there is illustrated one embodiment of a needle of the invention, i.e., a notchless tubular needle 70, in its natural, unconstrained state.

As used throughout the specification, the term "notchless" shall refer to the absence of notches, slots, eyelets, or other such transverse openings for receiving suture as typically formed in needles of prior art suture passers.

According to the invention, the needle 70 can also comprise a solid structure.

As illustrated in FIG. 2A, the distal end 80 of the needle 70 comprises a curvilinear configuration.

Figure 2B:
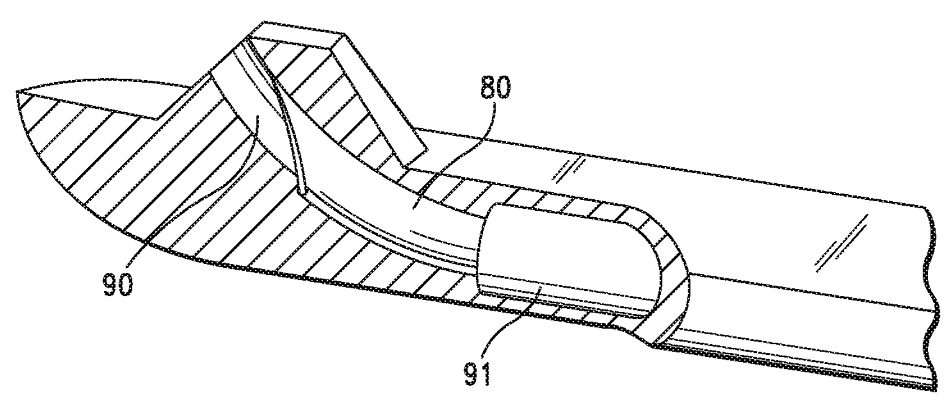
FIG. 2B is a partial side plan partial sectional view of a preformed tubular needle in a retracted, constrained state, in accordance with the invention.

As illustrated in FIG. 2B, the needle 70 comprises a formed end 80 sheathed in a constraining channel 91. In a preferred embodiment, the needle channel 91 also includes a curvilinear portion 90, or guide-path, which approximates the same geometry curve as the distal end 80 of the needle 70, thereby facilitating the consistent return of the needle 70 to its preformed curved shape each time the needle 70 exits the channel.

According to the invention, the constrained state needle 70 contained in the needle assembly 60 is loaded into the handle end of the elongated tubular body 10 and advanced through a guide channel or track in the tubular body 10.

FIG. 1A illustrates the hand grip 20 and actuator 50 of the suture passing device, which, as set forth in Applicant's U.S. Pat. No. 12,029,412, provide articulation of jaw 40 relative to tip 30.

Figure 3A:
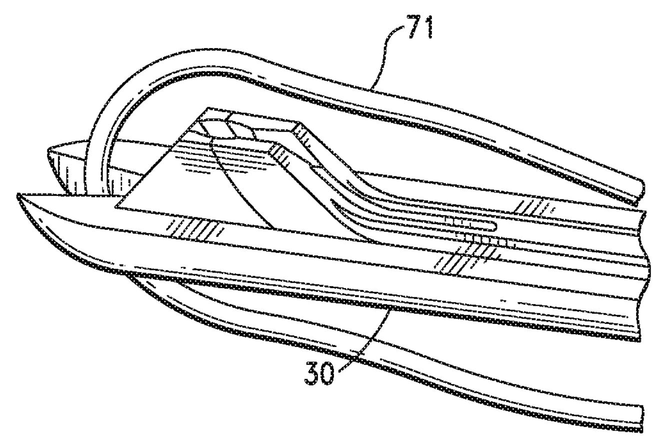
FIG. 3A is a partial perspective view of a lower jaw member of the system shown in FIG. 1A and a suture prior to loading in the lower jaw member, in accordance with the invention.
Figure 3B:
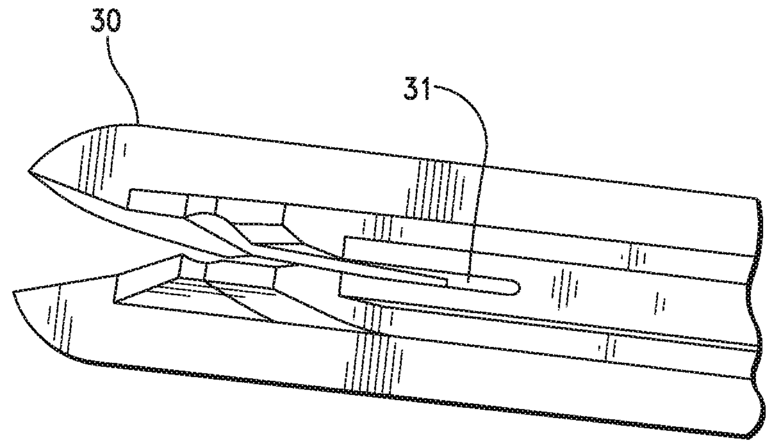
FIG. 3B is another perspective view of the lower jaw member shown in FIG. 3A showing the slot formed in the jaw member, in accordance with the invention.

As set forth in U.S. Pat. No. 12,029,412 and illustrated in FIGS. 3A and 3B, a loop of suture 71 is loaded into distal end of tip 30 with slot 31. According to the invention, the slot 31 facilitates spring action for gripping the loop of suture 71 when the loop of suture 71 is guided into the tip 30.

Figure 3C:
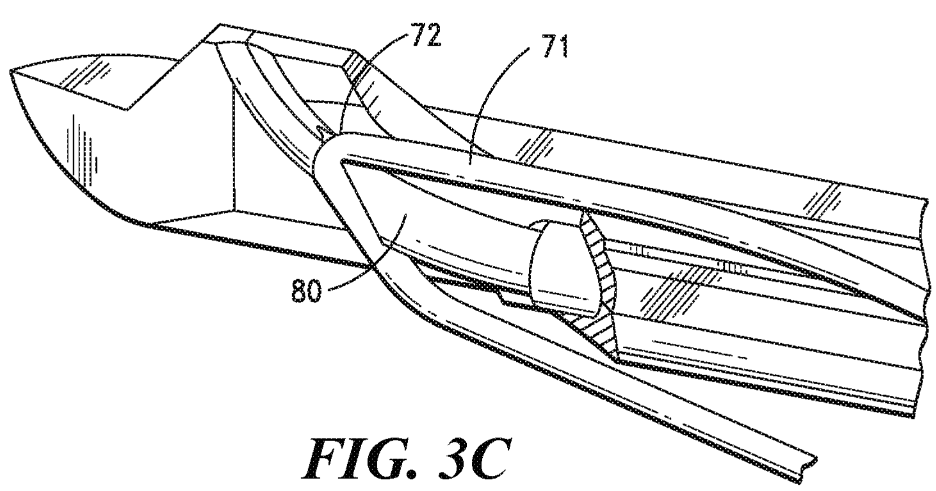
FIG. 3C is a partial perspective partial sectional view of the lower jaw member, tubular needle, and suture shown in FIG. 3A, in accordance with the invention.

In one embodiment of the invention, illustrated in FIG. 3C, tubular needle 70 pierces the loop of suture 71 and, thereby, creates a bifurcation 72 in the suture 71.

According to the invention, when additional force is applied to the suture 71, the bifurcation 72 advances along the shaft of the needle 70.

Figure 4A:
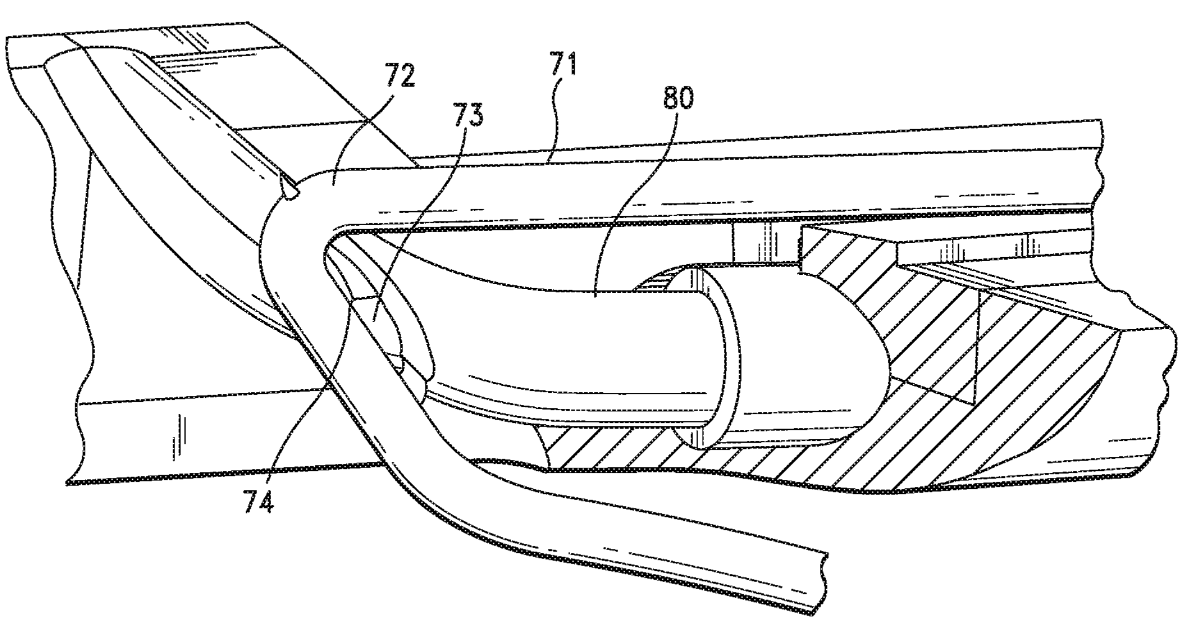
FIG. 4A is a partial perspective partial sectional view of the lower jaw member and tubular needle shown in FIG. 3A showing a cleat member engaged to the suture, in accordance with the invention.

As further set forth in U.S. Pat. No. 12,029,412 and illustrated in FIG. 4A, to prevent the bifurcation 72 from advancing along the shaft of the tubular needle 70, in some embodiments, a prong cleat 73 is positioned in the tubular needle 70 and adapted to pierce the loop of suture 71 loop in a second location. According to the invention, the pierce of the prong cleat 73 can partially engage the thickness of the suture 71 or create a second bifurcation 74 in the suture.

Figure 4B:
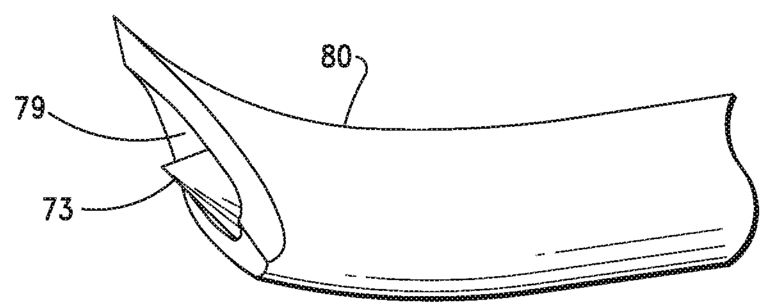
FIG. 4B is a partial perspective view of the tubular needle shown in FIG. 3A and the cleat member disposed in the lumen thereof, in accordance with the invention.
Figure 4C:
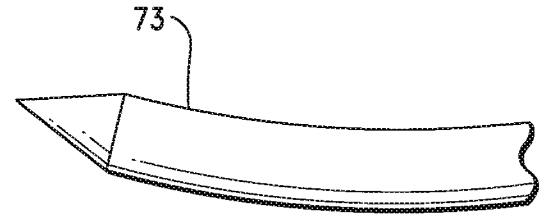
FIG. 4C is a partial perspective view of the cleat member shown in FIG. 4B, in accordance with the invention.

As illustrated in FIG. 4C, in a preferred embodiment, the prong cleat 73 comprises a wire rod or tube that is housed within the lumen 79 of the tubular needle 70. As further illustrated in FIG. 4C, the prong cleat 73 comprises a sharp distal tip, which slightly extends from the lumen 79 of the tubular needle 70, as illustrated in FIG. 4B. The piercing action of the needle 70 and the prong cleat 73 at different locations in the suture 71 act in conjunction to stabilize the suture 71 and prevent the suture 71 from advancing along the shaft of the needle 70.

Figure 5A:
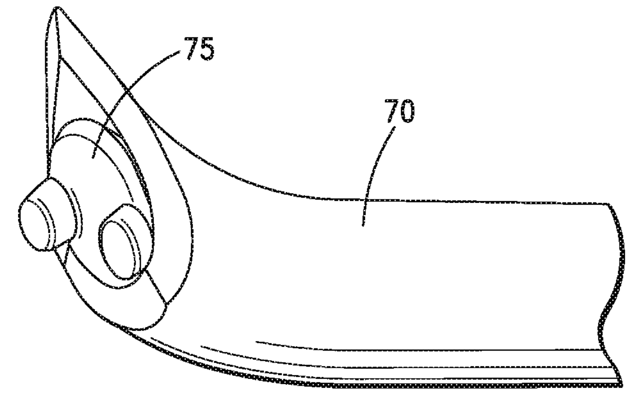
FIG. 5A is a partial perspective view of the tubular needle shown in FIG. 4B comprising another embodiment of a cleat member disposed in the lumen thereof, in accordance with the invention.
Figure 5B:
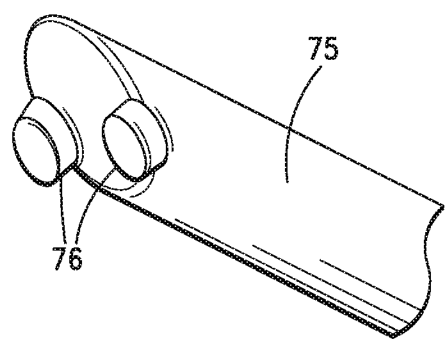
FIG. 5B is a partial perspective view of the cleat member shown in FIG. 5A, in accordance with the invention.
Figure 5C:
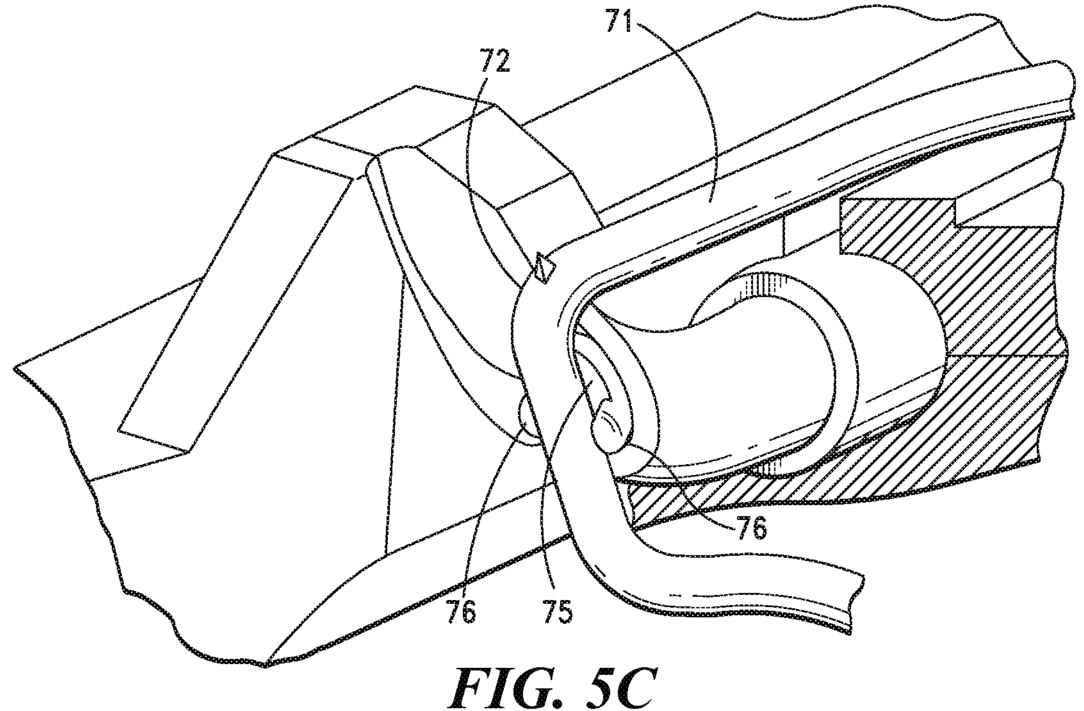
FIG. 5C is a partial perspective view of the lower jaw member, tubular needle, the embodiment of the cleat member shown in FIG. 5A, and suture, in accordance with the invention.

Referring back to FIG. 3C, in another embodiment, tubular needle 70 pierces the loop of suture 71 and creates a bifurcation 72 in the suture 71. When additional force is applied to the suture 71, the bifurcation 72 advances along the shaft of the needle 70. To prevent the bifurcation 72 from advancing along the shaft of the needle 70, a lateral post cleat 75, illustrated in FIGS. 5A and 5B, is positioned to engage the bifurcated section of the suture 71 with cleat posts 76, as illustrated in FIG. 5C.

Figure 6A:
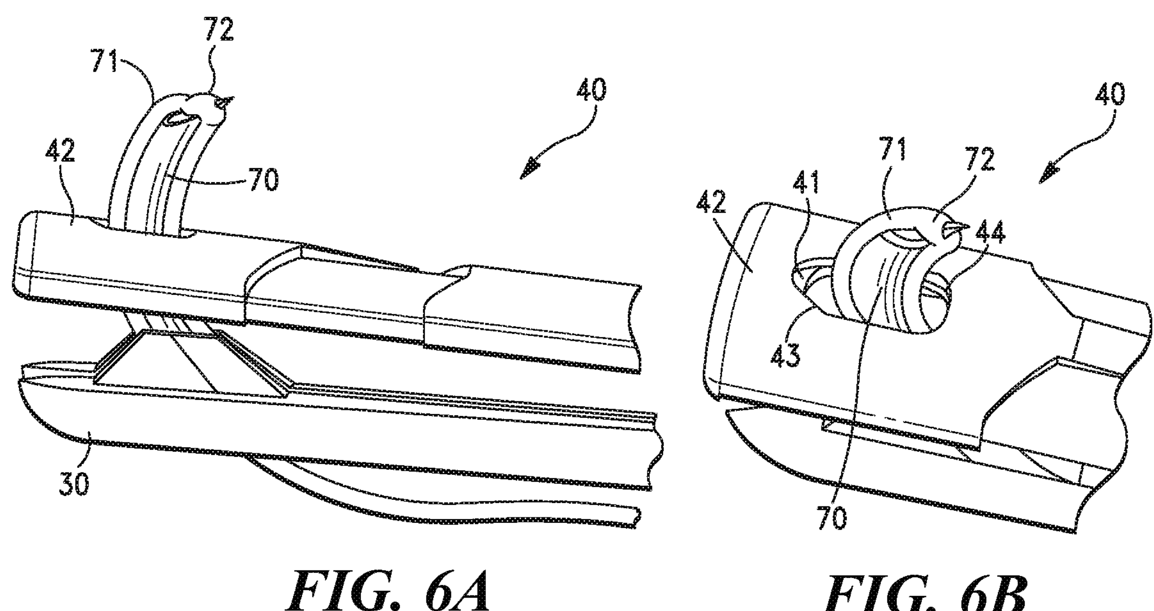
FIG. 6A is a partial side view of the tubular needle that is extended to engage and carry the suture through the aperture of the jaw mechanism and pawl, in accordance with the invention.
Figure 6B:
FIG. 6B is a partial perspective view of the tubular needle that is extended to carry the suture through the aperture of the jaw mechanism and pawl shown in FIG. 6A, in accordance with the invention.

Referring now to FIGS. 6A and 6B, there is illustrated one embodiment of a jaw mechanism 40 having an aperture 41 therein, which is sized and configured to receive tubular needle 70 and suture 71 and allow tubular needle 70 and suture 71 to pass therethrough.

Figure 6C:
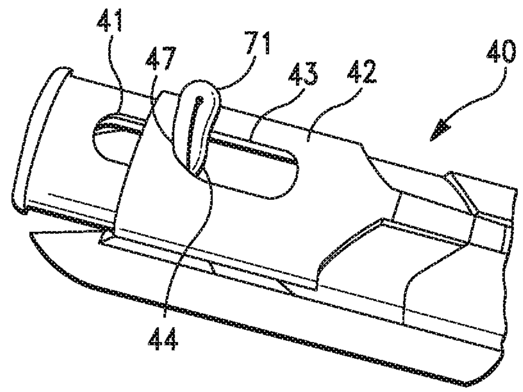
FIG. 6C is a perspective view of the suture captured by the pawl shown in FIG. 6A, in accordance with the invention.

As illustrated in FIGS. 6B and 6C, the jaw mechanism 40 further comprises a retractable pawl 42, which includes a window 43 that aligns with aperture 41 when the retractable pawl 42 is extended forward in the open position. When the tubular needle 70 and suture 71 are deployed within aperture 41 via actuator 50, the retractable pawl 42 is then moved to a retracted or rearward position, as illustrated in FIG. 6C. In some embodiments, the retractable pawl actuation mechanism includes a spring bias to provide a relatively constant force of the retractable pawl 42 against the deployed tubular needle 70 and suture 71.

Figure 6D:
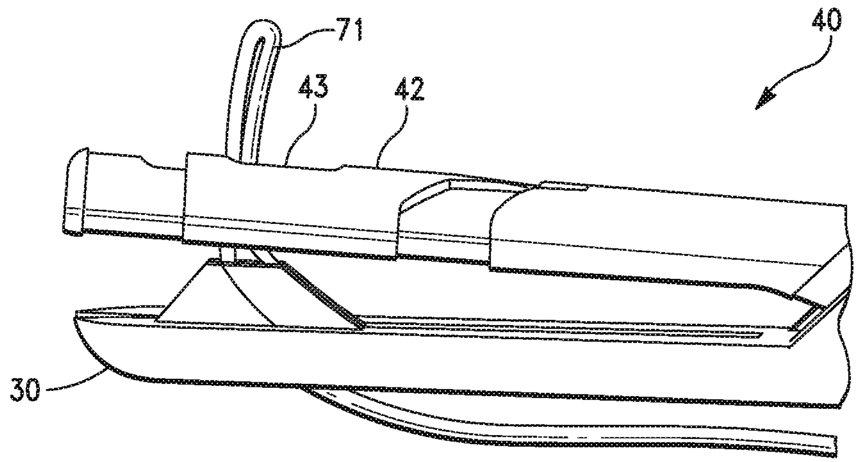
FIG. 6D is a side plan view of the suture captured by the pawl shown in FIG. 6A, in accordance with the invention.

As set forth in U.S. Pat. No. 12,029,412, upon release of the actuator 50, a spring in the actuator mechanism returns the tubular needle 70 to the constraining channel 90. The spring bias of the retractable pawl 42 allows the tubular needle 70 to return yet allows the retractable pawl 42 to maintain a grip on the suture 71 and pulls it in a rearward movement to become captured in between the proximal edge 44 of the aperture 41 in the jaw 40 and distal edge 47 of pawl window 43, as is shown in FIGS. 6C and 6D. Complete release of the actuator 50 disengages the jaw mechanism 40 to the default open position, thus, completing the passage of suture 71 through the soft tissue.

Figure 7A:
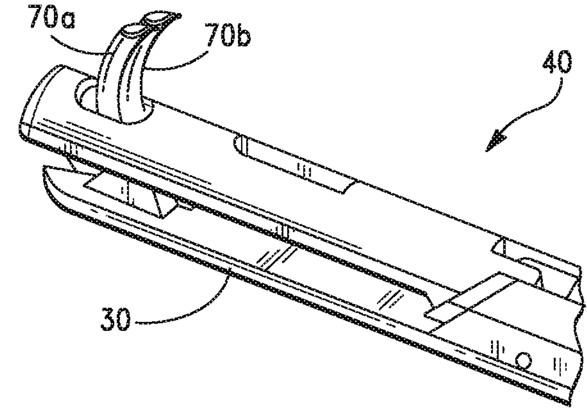
FIG. 7A is a partial perspective view of another embodiment of a suture passing device comprising two (2) tubular needles and a jaw mechanism with the two tubular needles extended through the aperture of the jaw mechanism, in accordance with the invention.

As further set forth in U.S. Pat. No. 12,029,412, in some embodiments, the suture passing system is configured to comprise two (2) or more tubular needles 70. In one embodiment, the suture passing system can throw more than one segment of suture 71 through soft tissue simultaneously. An exemplar two (2) needle suture passing device is illustrated in FIG. 7A, which shows a left tubular needle *70a* and a right tubular needle *70b* after being released to their natural states.

The segments of suture being passed by multiple tubular needles 70 can be attached to form a continuous loop of suture, thus enabling the formation of a desired suture pattern, e.g., a horizontal mattress stitch.

In some embodiments of the invention, the suture passing system is configured to deploy the left needle *70a* and right needle *70b* independently.

Figure 7B:
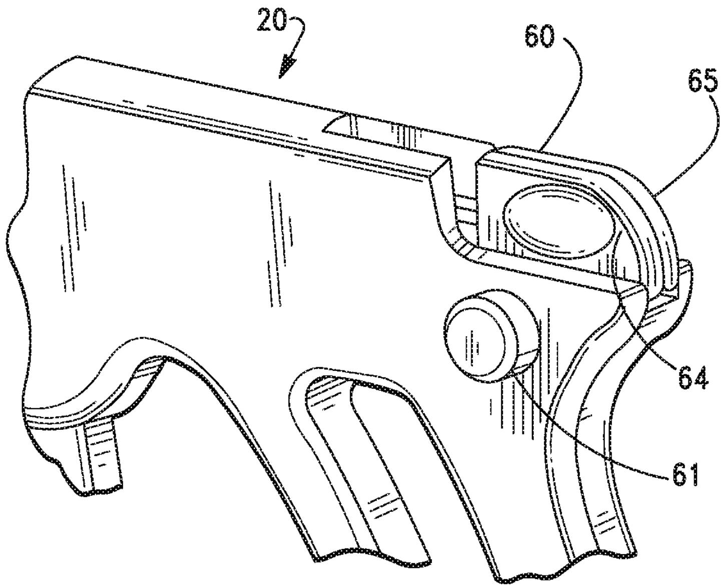
FIG. 7B is a partial perspective view of the hand grip, toggle switch and needle assemblies of the suture passing device shown in FIG. 7A, in accordance with the invention.

Referring now to FIG. 7B, there is illustrated another embodiment of handle mechanism 20 that is adapted to modulate multiple needles independently. As illustrated in FIG. 7B, the handle mechanism 20 comprises a switch 61 to toggle and engage one needle assembly at a time in the drive track 60. When the switch 61 of the handle mechanism 20 is toggled to engage the left needle assembly 64, the jaw mechanism 40 can be actuated to grasp a desired location of soft tissue and the left tubular needle *70a* is deployed to pass and capture suture in a first soft tissue location.

As further set forth in U.S. Pat. No. 12,029,412, fully releasing the actuator 50 returns the left tubular needle *70a* to its constrained state and disengages jaw mechanism 40. The suture passing device can then be repositioned to a second desired soft tissue location. When the switch 61 is toggled to engage the right tubular needle *70b*, the jaw mechanism 40 can be actuated to grasp a second desired location of soft tissue and the right needle *70b* is deployed to pass and capture suture in a second soft tissue location. Fully releasing the actuator 50 returns the right tubular needle *70b* to its constrained state and disengages jaw mechanism 40 from soft tissue. The suture passing system can then be removed from the cannula to expose the two ends of the suture.

As further set forth in U.S. Pat. No. 12,029,412 and illustrated in FIGS. 8A-8C, in some embodiments, the suture passing system described above comprises a floating pivot mechanism to facilitate a lower profile when the jaw mechanism 40 and tip 30 are separated. In some embodiments, the jaw mechanism 40 thus includes a pivot interface 36 with a linkage 35. At the opposite end of linkage 35 is another pivot interface 37 that joins linkage 35 and drive rod 38.

Figure 8A:
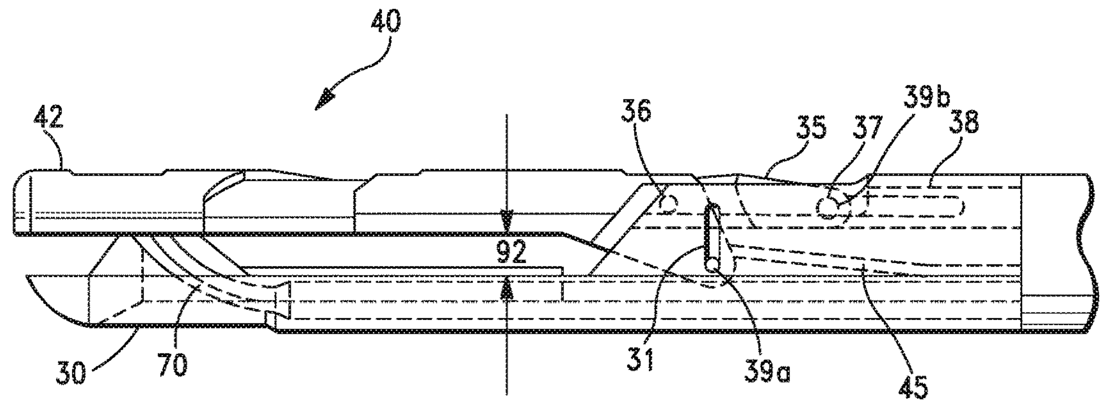
FIG. 8A is a side plan view of the jaw mechanism shown in FIG. 6A with a slot and floating pivot mechanism in the collapsed state, in accordance with the invention.
Figure 8B:
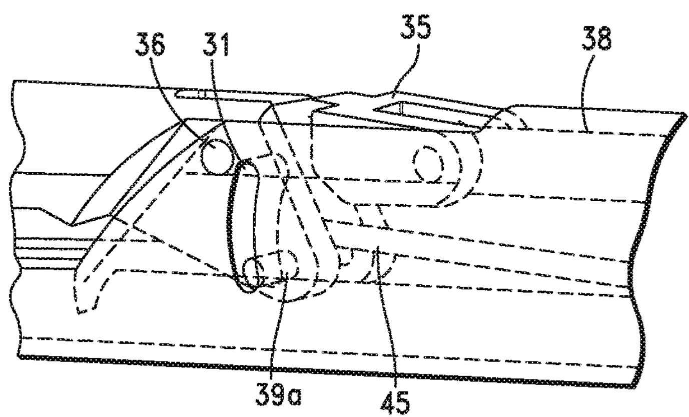
FIG. 8B is a perspective view of the floating pivot mechanism, in accordance with the invention.

As illustrated in FIGS. 8A and 8B, the tip 30 includes a slot 31 in which a pin 39*a* slidably translates within. The pin 39*a* is fixed to jaw mechanism 40. Axial movement of drive rod 38 in relation to the tip 30 causes jaw mechanism 40 to rotate about pin 39*a* in relationship to the tip 30.

As further illustrated in FIGS. 8A and 8B, a leaf spring 45 exerts a force on the pin 39*a* to bias the pin 39*a* against the lower end of slot 31, thus, resulting in the jaw mechanism 40 being positioned in a collapsed state and the gap 92 between the inner surfaces of the tip 30 and jaw mechanism 40 being minimized.

The collapsed state of the jaw mechanism 40 is advantageous for providing a minimum profile for advancing the device through an access cannula. According to the invention, the device can be configured to be advanced into the through an access cannula having a diameter in the range of 2.0 mm-15.0 mm, more preferably, in the range of 5.0 mm-8.0 mm.

Figure 8C:
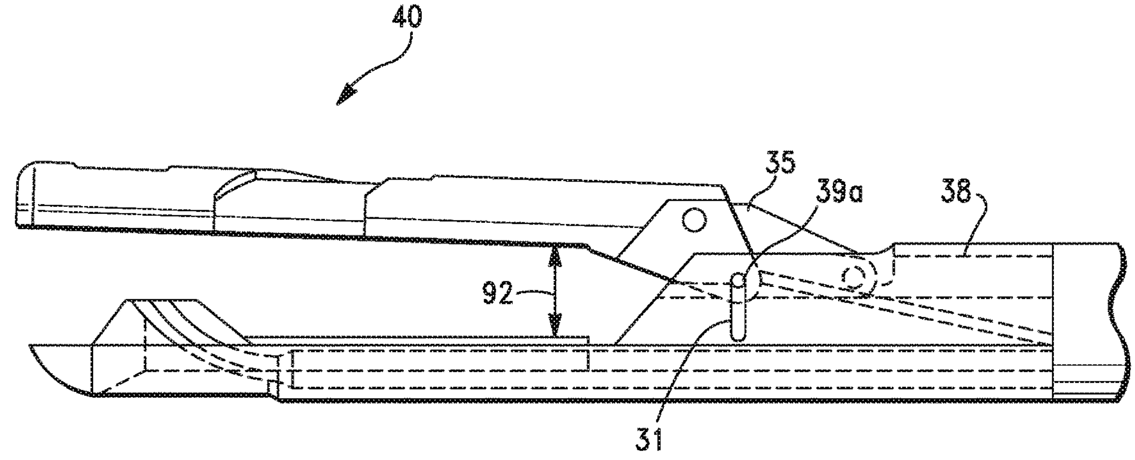
FIG. 8C is a side plan view of the jaw mechanism shown in FIG. 6A with a slot and floating pivot mechanism in the expanded or vertically articulated state, in accordance with the invention.

When the tip 30 and jaw mechanism 40 are positioned proximate soft tissue, advancement of the drive rod 38 causes the jaw mechanism 40 to rotate about pin 39*a* to clamp onto the tissue. The resisting force of the soft tissue to compression between tip 30 and the jaw mechanism 40 results in a force applied to the inner surface of the jaw mechanism 40. If the force applied to the inner surface of the jaw mechanism 40 exceeds the force of the leaf spring 45 provided to hold the pin 39*a* against the lower end of slot 31, the pin 39*a* will ride up the slot 31, and increase the gap 92 between the inner surfaces of tip 30 and the jaw mechanism 40, as illustrated in FIG. 8C.

In some embodiments, the gap 92 between the inner surfaces of tip 30 and the jaw mechanism 40 comprises a width in the range of 0.5 mm-5.0 mm, more preferably, a width in the range of 1.5 mm-3.3 mm.

Figures 9A, 9B, 9C:
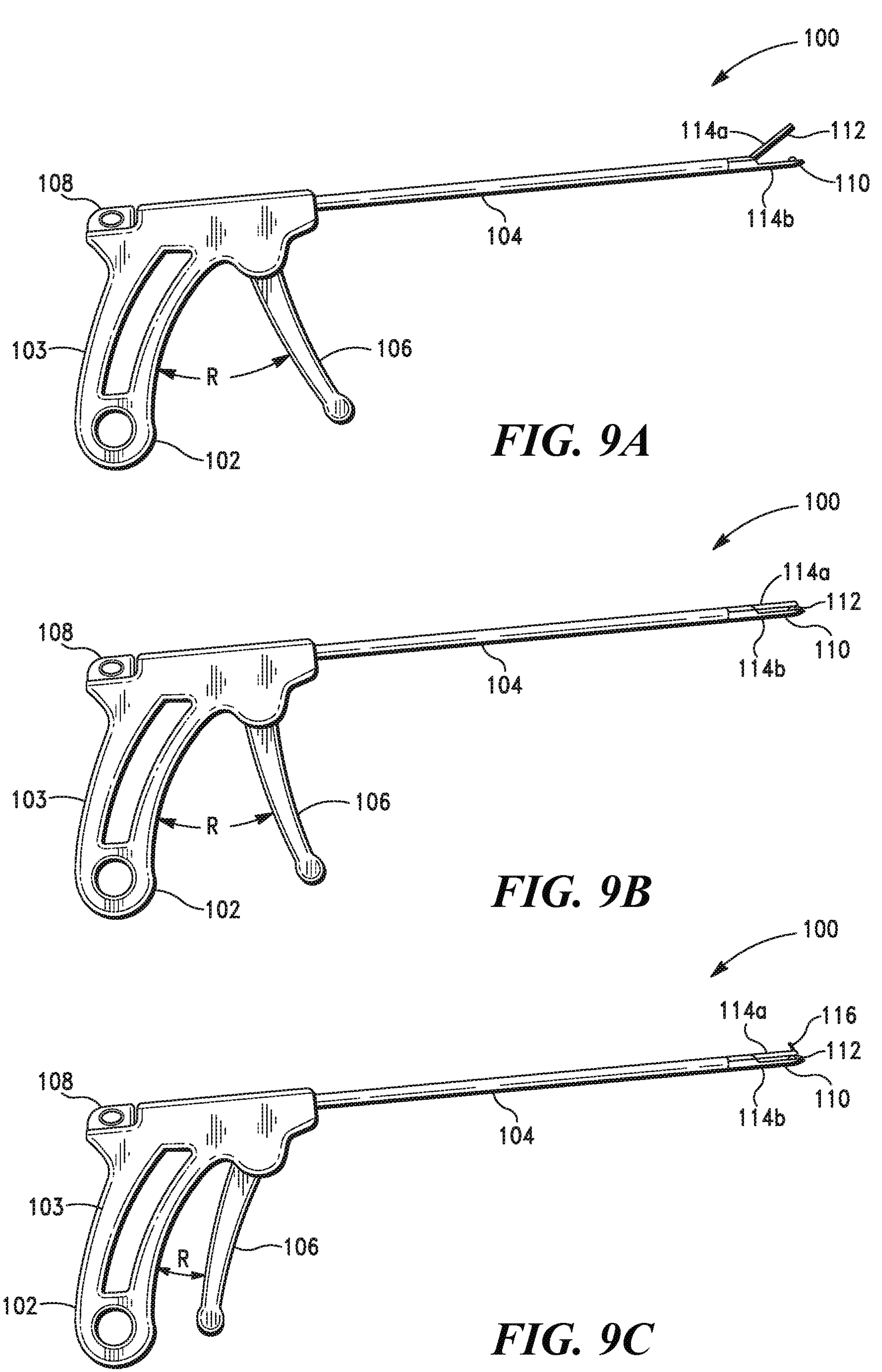
FIGS. 9A-9C are side plan views of another embodiment of a suture passing system in various stages of deployment, in accordance with the invention.

Referring now to FIGS. 9A-9C, there is shown another embodiment of a suture passing system 100 at various stages of actuation. As illustrated in FIG. 9A, the suture passing system 100 of the present invention comprises a hand grip 102 in operative communication with elongated tubular body or member 104 having a distal end 110.

As further illustrated in FIG. 9A, hand grip 102 comprises a proximal end 103, an actuator 106 and a needle assembly 108, and elongated tubular member 104 comprises a jaw mechanism 112 having top and bottom jaw members 114*a*, 114*b* disposed proximate the elongated tubular member 104 distal end 110. In a preferred embodiment, the jaw mechanism 112 top and bottom jaw members 114*a*, 114*b* comprise proximal and distal ends.

In a preferred embodiment, the jaw mechanism 112 of the suture passing system 100 similarly comprises the floating pivot mechanism and pivot interface discussed above and shown in FIGS. 8A-8C to facilitate a lower profile when the top and bottom jaw members 114*a*, 114*b* of jaw mechanism 112 are separated and during axial articulation of the top and bottom jaw members 114*a*, 114*b*.

In the noted embodiments, the jaw mechanism 112 preferably comprises first and second pins 39*a*, 39*b*, the proximal end of the jaw mechanism 112 top jaw member 114*a* comprises first and second pin lumens, and the proximal end of the jaw mechanism 112 bottom jaw member 114*b* comprises a third pin lumen and a pin slot 31.

Preferably, the first pin lumen and the pin slot 31, and the second and third pin lumens are in axial alignment.

In a preferred embodiment, the jaw mechanism 112 top jaw member 114*a* first pin lumen and the bottom jaw member 114*b* pin slot 31 are configured to receive and position the jaw mechanism 112 first pin 39*a*, wherein, when the jaw mechanism 112 first pin 39*a* is received by and positioned in the jaw mechanism 112 top jaw member 114*a* first pin lumen and the bottom jaw member pin slot 31, the jaw mechanism 112 top jaw member 114*a* is allowed to vertically or linearly articulate with respect to the jaw mechanism 112 bottom jaw member 114*b*.

In a preferred embodiment, the jaw mechanism 112 top jaw member 114*a* second pin lumen and the bottom jaw member 114*b* third pin lumen are configured to receive and position the jaw mechanism 112 second pin 39*b*, wherein, when the jaw mechanism 112 second pin 39*b* is received by and positioned in the jaw mechanism 112 top jaw member 114*a* second pin lumen and the bottom jaw member third pin lumen, the jaw mechanism 112 top jaw member 114*a* is allowed to axially or rotatably articulate with respect to the jaw mechanism 112 bottom jaw member 114*b*.

According to the invention, any of the embodiments of the jaw mechanisms described herein can comprise the floating pivot mechanism and pivot interface discussed above and shown in FIGS. 8A-8C.

According to the invention, the suture passing system 100 can be used to capture and maintain soft tissue by positioning the jaw mechanism 112 of the suture passing device 100 proximate the soft tissue applying a first radial force on the actuator 106 to transition the top and bottom jaw members 114*a*, 114*b* of jaw mechanism 112 from an open configuration, as illustrated in FIG. 9A, to a closed configuration, as illustrated in FIG. 9B. A second radial force can also be applied to actuator 106 to deploy a tubular needle 116 having a suture attached thereto into and through the tissue, as illustrated in FIG. 9C and discussed in detail below.

In a preferred embodiment, the actuator 106 provides axial articulation of top jaw member 114*a* relative to bottom jaw member 114*b* of jaw mechanism 112. In some embodiments, the actuator 106 can be coupled to a return spring (not shown) that biases the actuator 106 in the open configuration shown in FIG. 9A.

In some embodiments of the invention, the actuator 106 of the hand grip 102 comprises a spring-loaded mechanism that is configured to provide a resistance force on the actuator 106 to provide tactile feedback for the operator to indicate that the tubular needle 116 is slidably translating into and through the jaw mechanism 112.

Figure 10A:
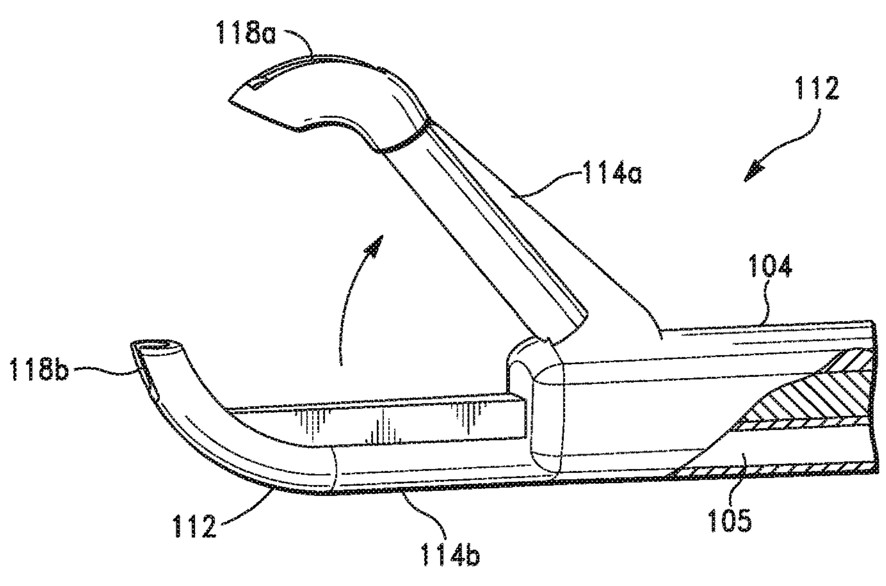
FIG. 10A is a side plan partial sectional view of an elongated member distal tip and jaw mechanism of the suture passing system shown in FIG. 9A prior to loading a suture, in accordance with the invention.

Referring now to FIG. 10A, there are shown top and bottom jaw members 114*a*, 114*b* of jaw mechanism 112 in an open configuration. As illustrated in FIG. 10A, the top jaw member 114*a* comprises a guide channel 118*a* and the bottom jaw member 114*b* comprises a guide channel 118*b*. In a preferred embodiment, the guide channels 118*a*, 118*b* are sized and configured to receive tubular needle 116 of the invention therein.

As further illustrated in FIG. 10A, in a preferred embodiment, guide channel 118*b* is in aligned communication with the elongated member 104 internal lumen 105.

Figure 10B:
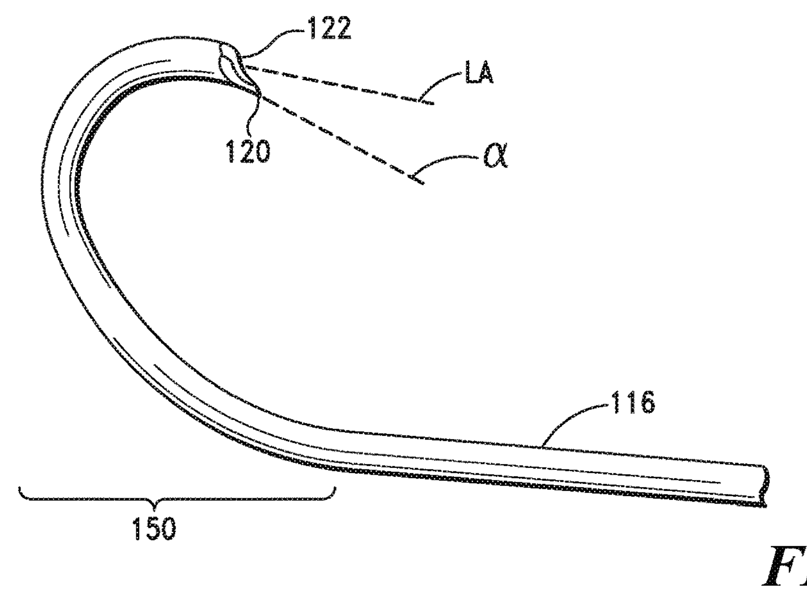
FIG. 10B is a side plan view of a preformed tubular needle, in accordance with the invention.
Figures 11A, 11B, 11C:
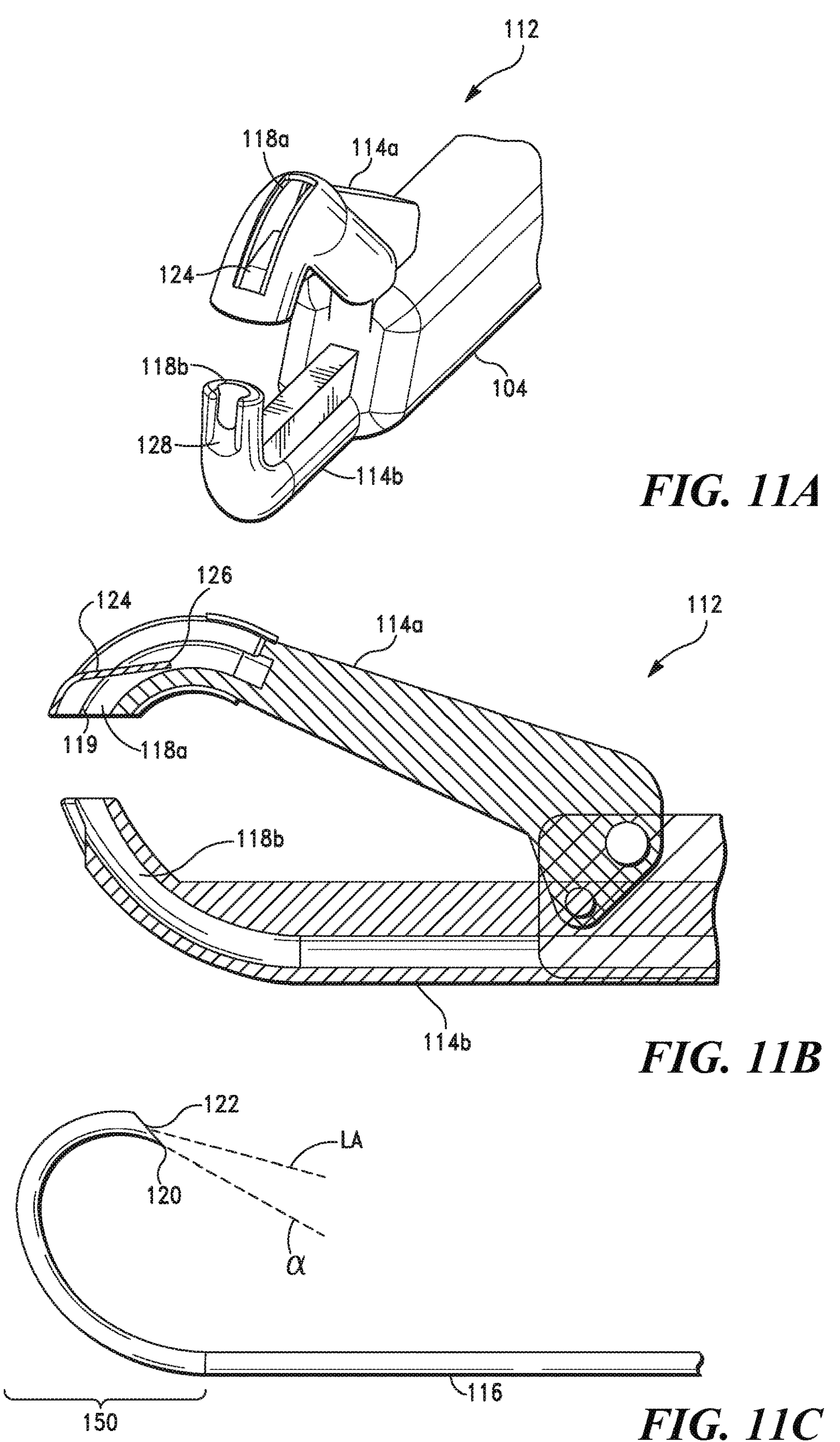
FIG. 11A is a perspective view of the elongated member distal tip and jaw mechanism of the suture passing system shown in FIG. 10A showing the pawl feature, in accordance with the invention.
FIG. 11B is a side plan sectional view of the elongated member distal tip and jaw mechanism shown in FIG. 10A showing the guide channel track for the needle, in accordance with the invention.
FIG. 11C is another partial side view of the tubular needle shown in FIG. 10B comprising two segments to match a guide channel track profile, in accordance with the invention.

Referring now to FIGS. 10B and 11C, there is shown tubular needle 116 in a first natural, unconstrained state comprising a distal end 120 and internal lumen 122. As illustrated in FIG. 10B, the tubular needle 116 comprises a formed curvilinear portion 150.

In some embodiments, the tubular needle 116 comprises multiple curvilinear sections 150 to slidably translate into and through the guide channels 118*a*, 118*b*. According to the invention, the curvilinear portion 150 of the tubular needle can comprise any suitable shape where 6.0% strain is not exceeded.

In a preferred embodiment, the tubular needle 116 comprises nickel-titanium alloy (Nitinol®) and is configured to transition (or deform) from an unconstrained or natural state to a constrained state, and from the constrained state back to the unconstrained state. As illustrated in FIG. 10B, in a preferred embodiment, the unconstrained state tubular member 116 comprises formed curvilinear portion 150.

Figure 10C:
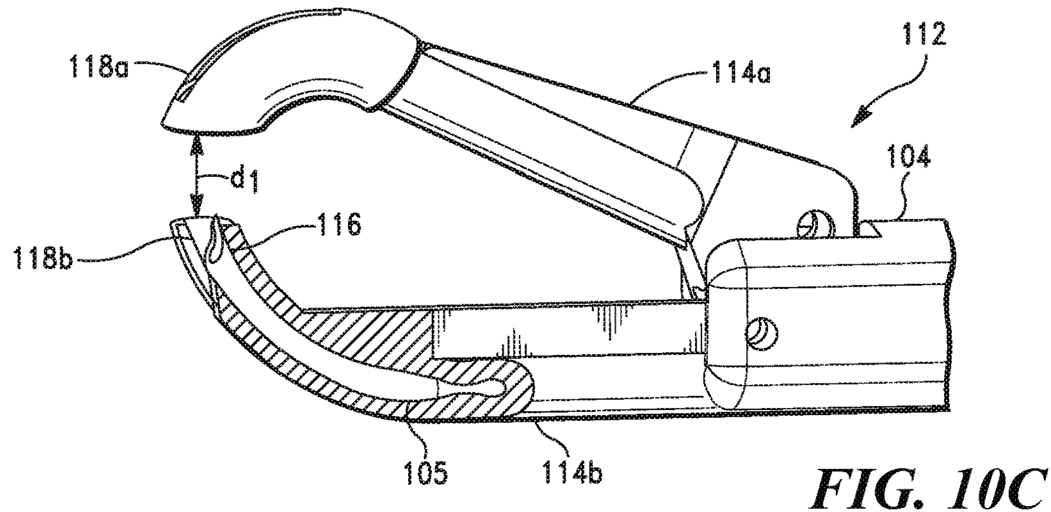
FIG. 10C is a side plan partial sectional view of a preformed tubular needle retracted and constrained in the guide channel of the bottom jaw member, and the jaw mechanism set at a determined gap distance, in accordance with the invention.

As shown in FIG. 10C, in some embodiments, the tubular needle 116 is adapted to transition or deform into a constrained state when the curvilinear portion 150 of the tubular needle 116 is advanced through the elongated tubular member 104 internal lumen 105 and into guide channel 118*b* of the jaw mechanism 112 bottom jaw member 114*b*.

In some embodiments, the curvilinear portion 150 of the tubular needle 116 is adapted to reassume a curvilinear shape upon further advancement out of guide channel 118*b* and into and through guide channel 118*a* of the jaw mechanism 112 top jaw member 114*a*.

In some embodiments, the tubular needle 116 comprises a hollow and rigid structure. In some embodiments, the tubular needle 116 comprises geometry where the area moment of inertia about the neutral bending axis is in the range of $20.0\times10^{-9}$-$300.0\times10^{-9}$ inches to the 4th power, more preferably, the tubular needle comprises a geometry where the area moment of inertia about the neutral bending axis in the range of 25.0× Oct. 9, $1975.0\times10^{-9}$ inches to the 4th power, which allows the tubular needle 116 to be driven into soft tissue with minimal deflection or skiving.

According to the invention, the tubular needle 116 distal end 120 can comprise various configurations, including, but not limited to, a beveled, curved, and serrated edge, which is configured to pierce through soft tissue.

In a preferred embodiment, the tubular needle 116 distal end 120 comprises a beveled edge having an angle "a" in the range of approximately 1°-90° with respect to the longitudinal axis "LA" of the tubular needle 116. More preferably, the angle "a" of the beveled distal end 120 is in the range of approximately 45°-90°.

In some embodiments, the needle 116 comprises a solid structure.

Referring now to FIG. 10C, there are shown top and bottom jaw members 114*a*, 114*b* of jaw mechanism 112 in a closed configuration comprising tubular needle 116 disposed in the guide channel 118*b* of bottom jaw member 114*b*. As illustrated in FIG. 10C, the top and bottom jaw members 114*a*, 114*b* of jaw mechanism 112 comprise a reciprocating curvilinear configuration that is configured to align guide channels 118*a*, 118*b* and, thereby, approximate the same curvilinear shape or configuration as the formed curvilinear portion 150 of the tubular needle 116 when the jaw mechanism 112 is in a closed configuration.

As further illustrated in FIG. 10C, when the top and bottom jaw members 114*a*, 114*b* of jaw mechanism 112 are in a closed configuration the top and bottom jaw members 114*a*, 114*b* are configured to be partially open at a set distance $d_1$ from each other.

In some embodiments, the top and bottom jaw members 114*a*, 114*b* are configured to fully close to facilitate passage through an access cannula.

In a preferred embodiment, the needle assembly 108 and the tubular needle 116 in communication therewith are engaged to the proximal end 103 of hand grip 102 and the tubular needle 116 is slidably transitioned into and through the elongated tubular member 104 internal lumen 105 in a constrained state.

Referring now to FIGS. 11A and 11B, there is illustrated pawl 124 of the top jaw member 114*a* of jaw mechanism 112. As illustrated in FIGS. 11A and 11B, the pawl 124 comprises a distal end 126 and intersects the guide channel 118*a* and, hence, the path defined by the guide channel 118*a*.

Figure 12A:
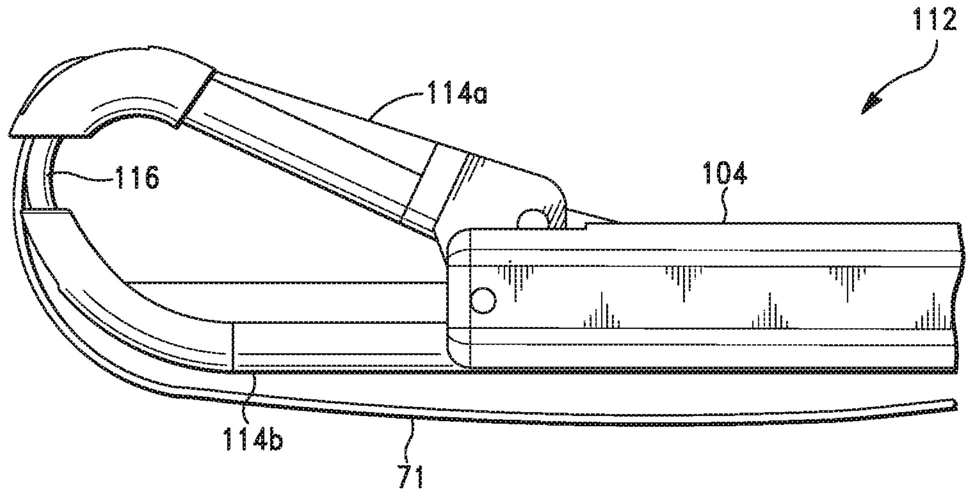
FIG. 12A is a perspective view of the suture passing system shown in FIG. 10A showing the elongated member distal tip, jaw mechanism, and tubular needle extended with suture, in accordance with the invention.
Figure 12B:
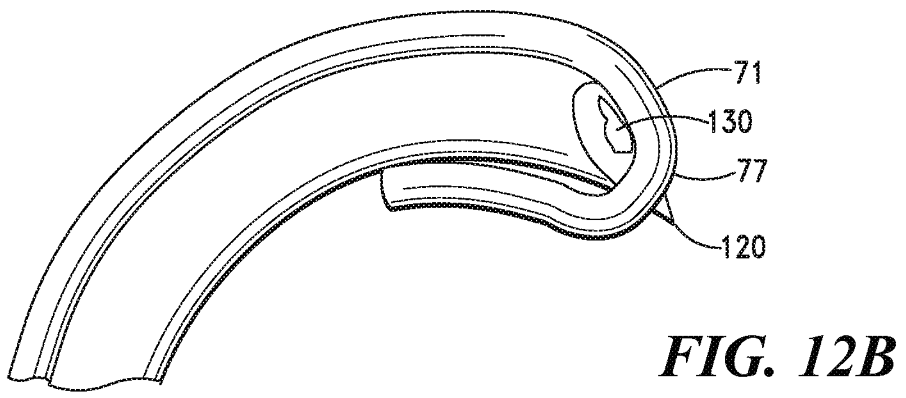
FIG. 12B is a partial perspective view of the tubular needle and cleat member of the suture passing system shown in FIG. 10A extended to engage and carry the suture through the aperture of the jaw mechanism, and pawl, in accordance with the invention.

As further illustrated in FIG. 11A, the bottom jaw member 114*b* of jaw mechanism 112 comprises a capture lip 128 that is configured to facilitate the capture of a portion of suture 71 shown in FIG. 12B.

Figure 12C:
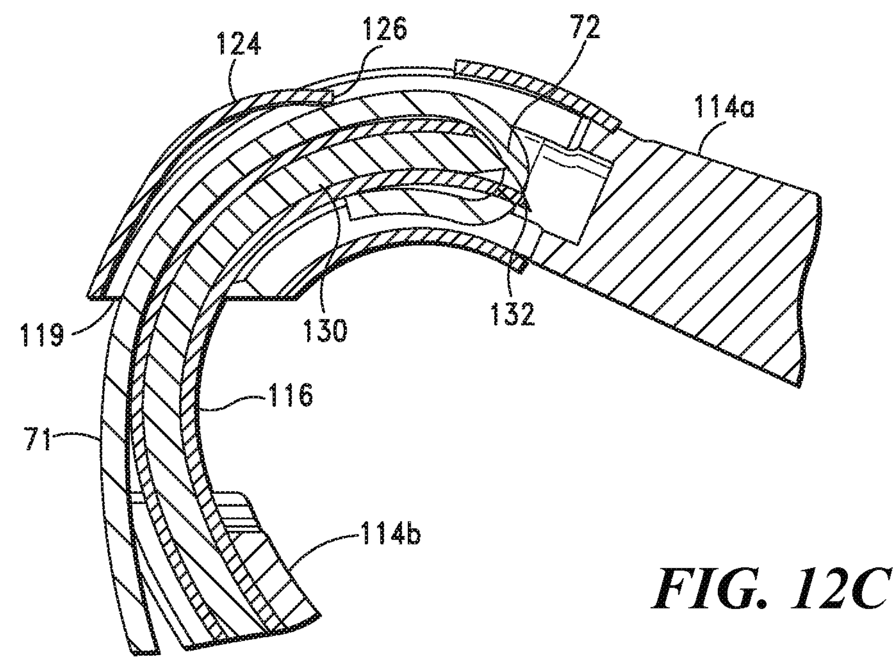
FIG. 12C is a side plan sectional view of the elongated member distal tip, jaw mechanism, tubular needle and cleat member of the suture passing system shown in FIG. 10A, and the suture loaded on the distal end of the tubular needle, in accordance with the invention.

As further set forth in U.S. Pat. No. 12,029,412, in some embodiments, the pawl 124 is used as a suture capturing mechanism. Referring now to FIG. 12C, when the tubular needle 116 guides the suture 71 into the guide channel 118*a* the pawl 124 is deflected, which allows the suture 71 to be guided beyond the distal end 126 of the pawl 124 by tubular needle 116.

According to the invention, when the tubular needle 116 is retracted from the guide channel 118*a* past the pawl 124, the distal end 126 of pawl 124 exerts a closure force on the suture 71 and captures the suture 71 between the pawl 124 distal end 126 and the inner wall 119 of guide channel 118*a*.

Referring now to FIGS. 12B and 12C, there is shown suture 71 having a distal end 77 that is loaded onto the distal end 120 of the tubular needle 116. As illustrated in FIGS. 12B and 12C, the distal end 120 of tubular needle 116 is configured to pierce at least a portion of suture 71.

As further illustrated in FIG. 12B, in a preferred embodiment, the distal tip 120 of tubular needle 116 is configured to pierce and form a bifurcation 72 in the suture 71.

As illustrated in FIGS. 12B and 12C, in some embodiments, the tubular needle 116 comprises a cleat member 130 having a piercing distal end 132 and is positioned in the tubular needle 116 internal lumen 122 and configured to pierce and engage at least a portion of the suture 71.

In a preferred embodiment, the tubular needle 116 distal end 120 and the cleat member 130 distal end 132 are adapted to pierce and engage suture 71 at two (2) predetermined locations on the suture 71 to secure the suture 71 thereto.

Figure 13A:
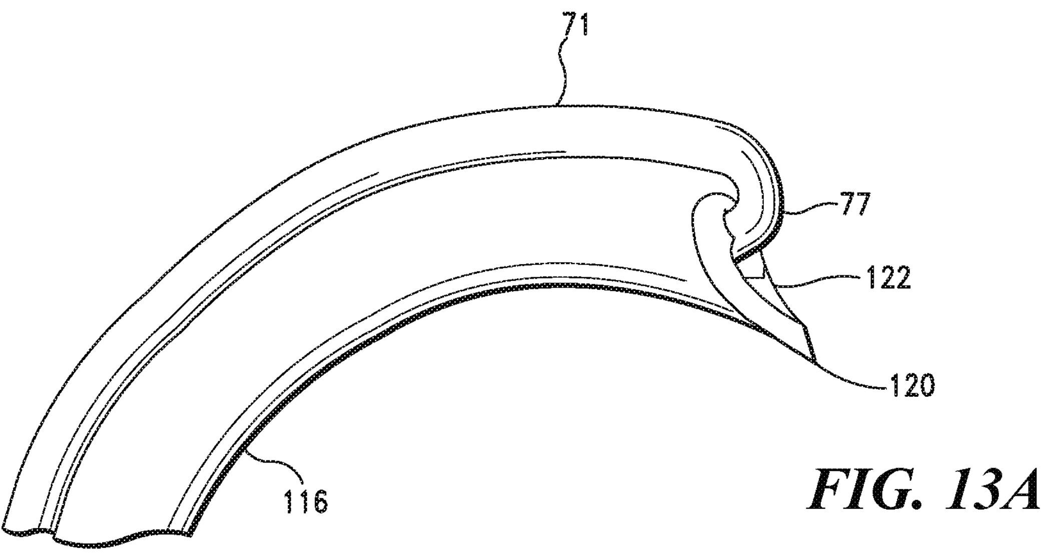
FIG. 13A is a partial perspective view of the tubular needle of the suture passing device shown in FIG. 10A with a front-loaded suture, in accordance with the invention.
Figure 13B:
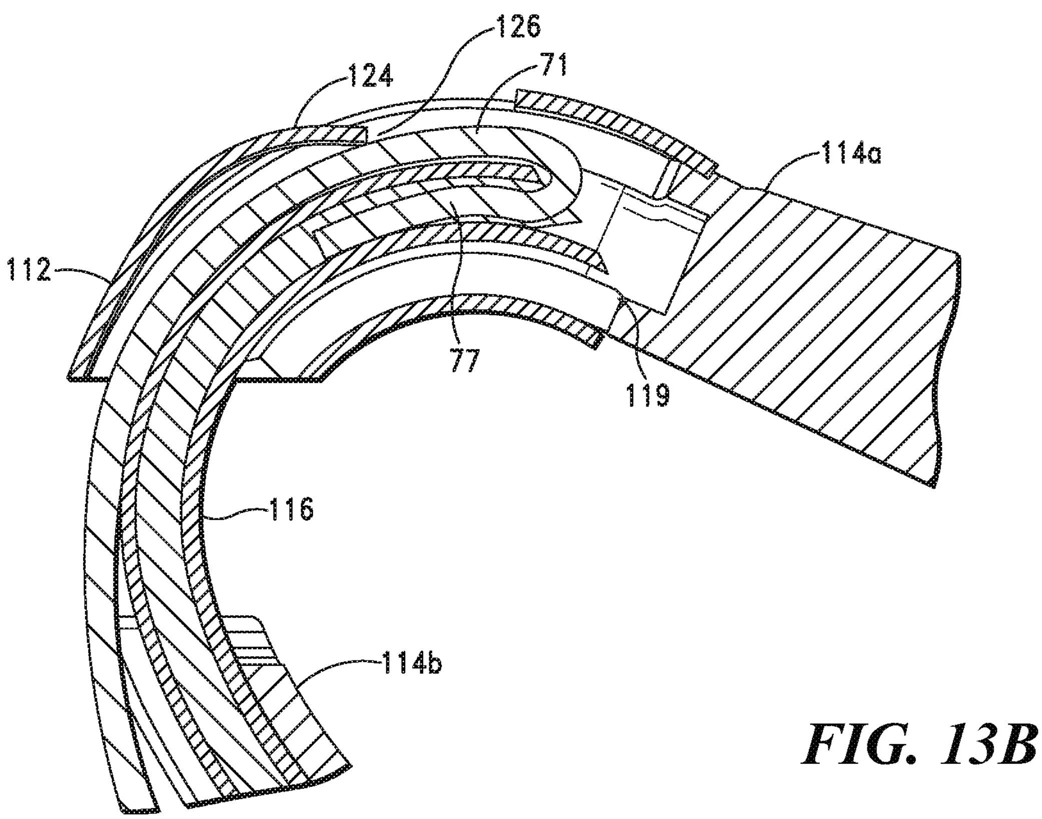
FIG. 13B is a side plan sectional view of the elongated member distal tip, jaw mechanism, and tubular needle of the suture passing system shown in FIG. 10A with a front-loaded suture, in accordance with the invention.

Referring now to FIGS. 13A and 13B, there is illustrated distal end 77 of suture 71 front loaded into the internal lumen 122 of the tubular needle 116 distal end 120. As illustrated in FIGS. 13A and 13B, the bend in the distal end 77 of the suture 71 provides a strain relief section that functions to releasably secure the distal end 77 of the suture 71 to the tubular needle 116 distal end 120 for penetration and advancement into soft tissue. According to the invention, when the tubular needle 116 is retracted from soft tissue, at least a portion of suture 71 is captured and retained by the soft tissue.

As illustrated in FIG. 13B, in some embodiments, the suture 71 distal end 77 is engaged by the distal end 126 of pawl 124, wherein the suture 71 distal end 77 is captured between the distal end 126 of pawl 124 and the inner wall 119 of the guide channel 118*a*.

Referring now to FIGS. 14-19, there is shown another embodiment of a jaw mechanism (now denoted "212") comprising top and bottom jaw members 214*a*, 214*b* and a suture retriever component (or needle shield) 250 that is secured to the jaw mechanism 212 top jaw member 214*a*.

Figure 14:
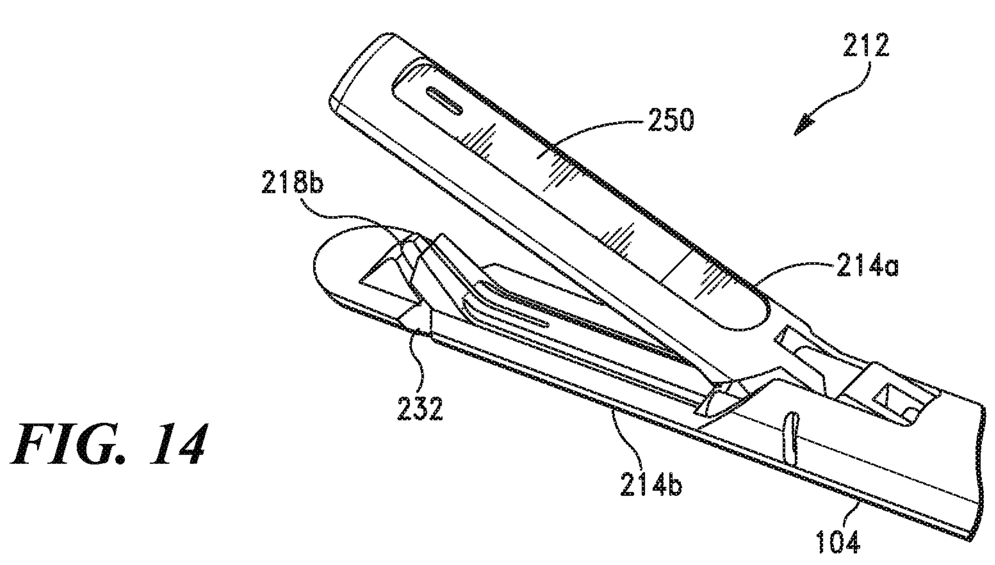
FIG. 14 is a perspective view of another embodiment of the suture passing system comprising a jaw mechanism in the open position with the tubular needle fully retracted, showing the needle shield secured to the jaw mechanism top jaw member, in accordance with the invention.
Figure 15:
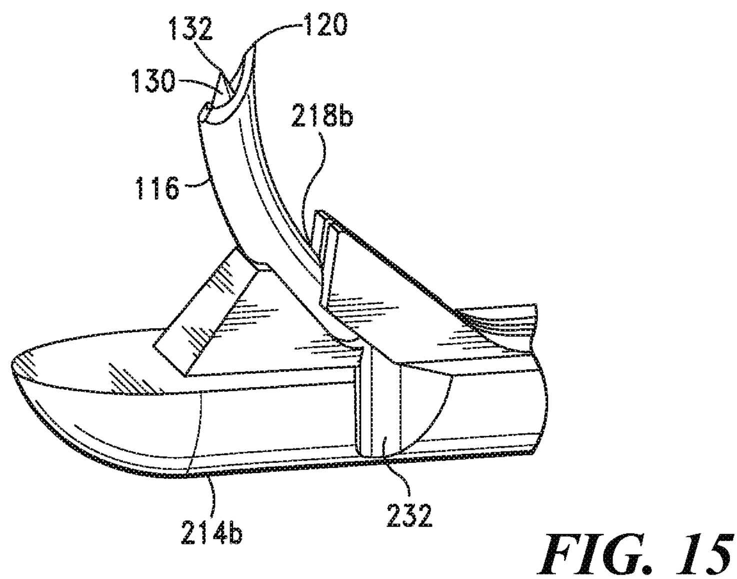
FIG. 15 is a perspective view of tubular needle of the suture passing system shown in FIG. 14 that is extending from the guide channel of the bottom jaw member and transitioning from a constrained to an unconstrained configuration, in accordance with the invention.
Figure 16:
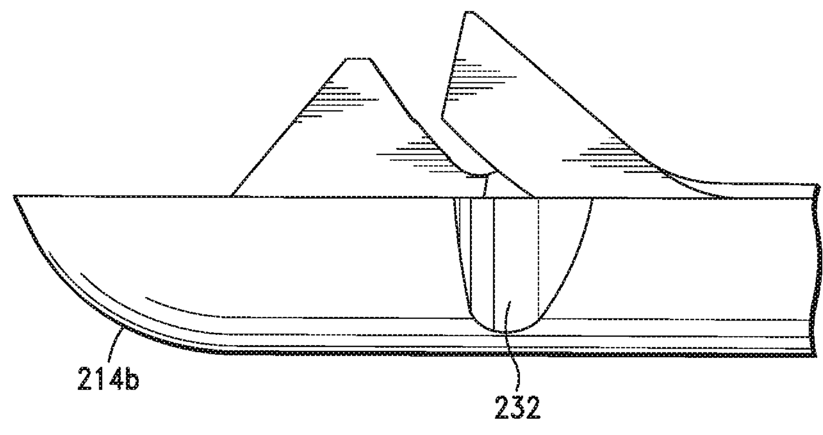
FIG. 16 is a partial side plan view of the bottom jaw member of the jaw mechanism shown in FIG. 14 showing the suture loading slot that is disposed on a lateral side of the bottom jaw member, in accordance with the invention.

As illustrated in FIGS. 14-16, the jaw mechanism 212 bottom jaw member 214*b* similarly comprises a guide channel 218*b* that is configured to receive tubular needle 116 having cleat member 130 disposed in the internal lumen 122 thereof. As further illustrated in FIGS. 14-16, in a preferred embodiment, the guide channel 218*b* comprises a curvilinear shape or geometry that is configured to approximate the same curvilinear shape or configuration as the formed curvilinear portion 150 of the tubular needle 116.

In a preferred embodiment, guide channel 218*b* is in aligned communication with the elongated member 104 internal lumen 105.

As illustrated in FIG. 16, the jaw mechanism 212 bottom jaw member 214*b* comprises a suture loading slot 232 that transects the guide channel 218*b* of the bottom jaw member 214*b*.

Figures 17, 18, 19:
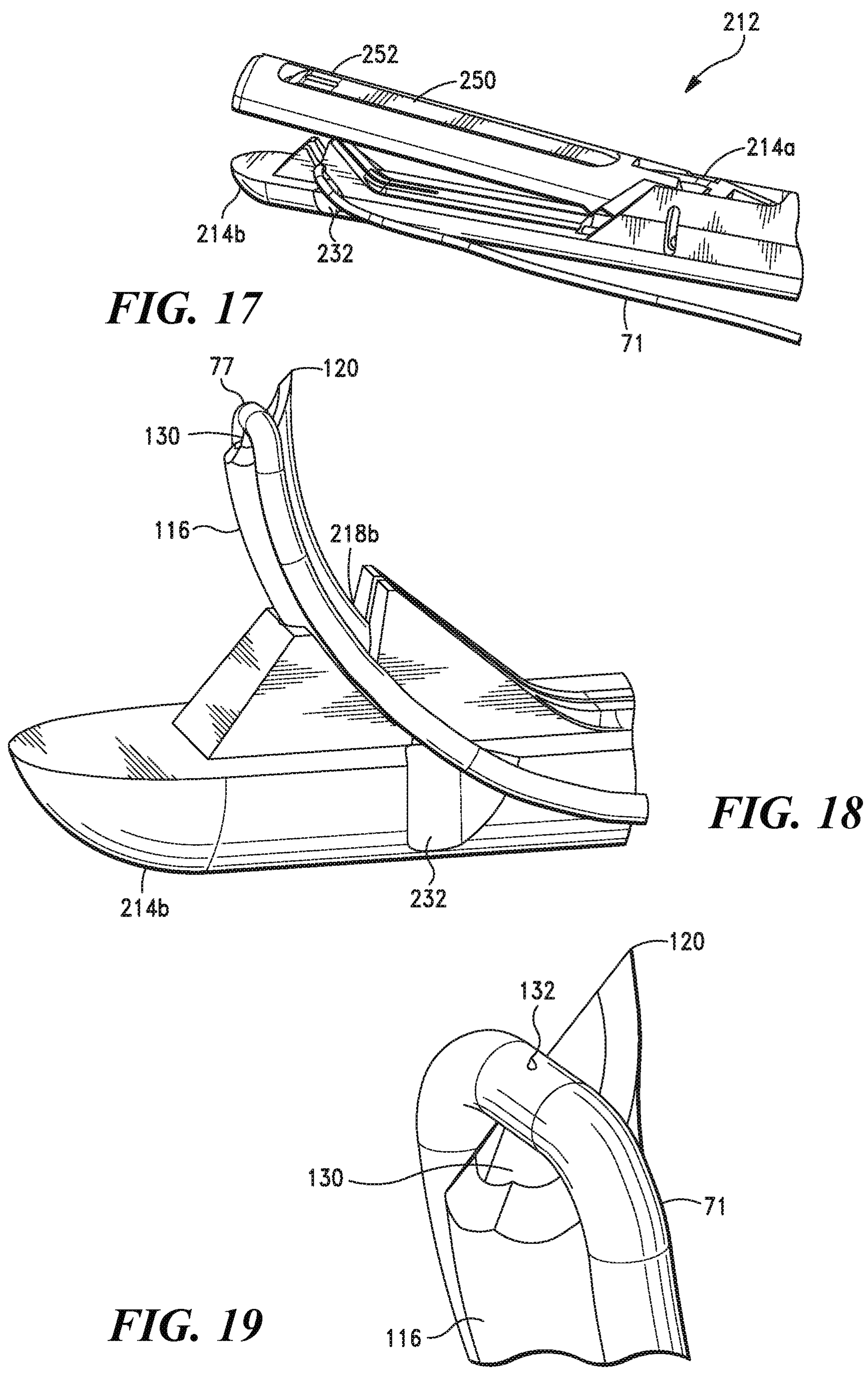
FIG. 17 is a perspective view of the jaw mechanism shown in FIG. 14 with the suture laterally loaded in the bottom jaw member, in accordance with the invention.
FIG. 18 is a perspective view of a tubular needle of the suture passing system shown in FIG. 14 extended from the guide channel of the bottom jaw member and transitioned from a constrained to an unconstrained configuration with a suture engaged thereto, in accordance with the invention.
FIG. 19 is a partial perspective view of the tubular needle shown in FIG. 18 with the cleat member engaged with the suture, in accordance with the invention.

As illustrated in FIG. 17, in a preferred embodiment, the suture 71 is loaded into the suture loading slot 232 from either lateral side, whereby the suture 71 is allowed to slidably translate therethrough and intersect a path defined by the guide channel 218*b*, wherein the suture 71 can be engaged by the tubular needle 116 as it is slidably translated through guide channel 218*b*.

As illustrated in FIGS. 18 and 19, in a preferred embodiment, when the tubular needle 116 comprising cleat member 130 disposed therein is slidably translated through guide channel 218*b*, the cleat member 130 distal end 132 pierces and engages at least a portion of suture 71. As the tubular needle 116 is slidably translated further through the guide channel 218*b* of the jaw mechanism 212 bottom jaw member 214*b*, the tubular needle 116 drives the portion of suture 71 forward and into the window 254 of the jaw 212 mechanism top jaw member 214*a*.

As further illustrated in FIG. 18, in a preferred embodiment, the curvilinear portion 150 of the tubular needle 116 is adapted to transition from a constrained state to an unconstrained state and reassume a curvilinear, unconstrained shape upon further advancement out of guide channel 218*b*.

Figure 20:
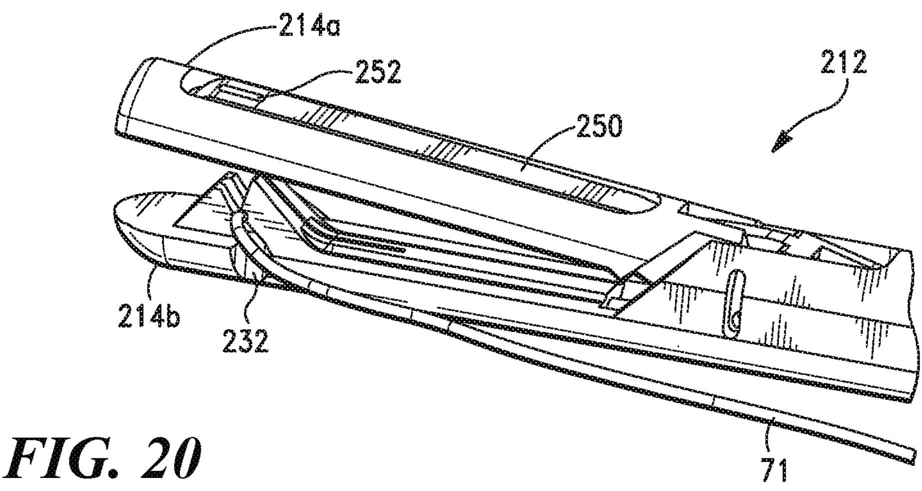
FIG. 20 is a perspective view of the jaw mechanism of the suture passing system shown in FIG. 14, with the tubular needle shield in the default state, in accordance with the invention.
Figure 21:
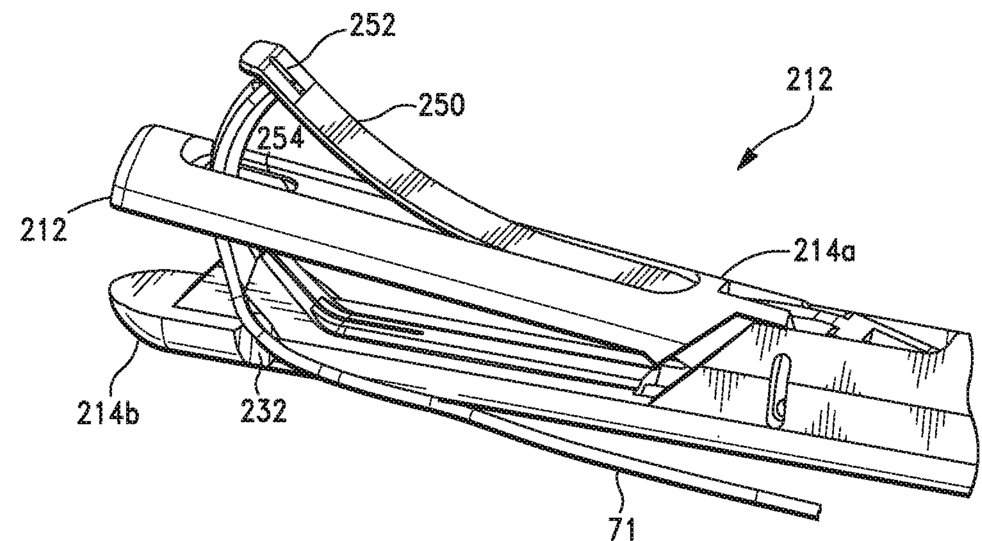
FIG. 21 is a perspective view of the jaw mechanism shown in FIG. 20 with the tubular needle shield in the deflected state, thereby, shielding the tubular needle distal end from surrounding tissue in a surgical site, in accordance with the invention.
Figure 22:
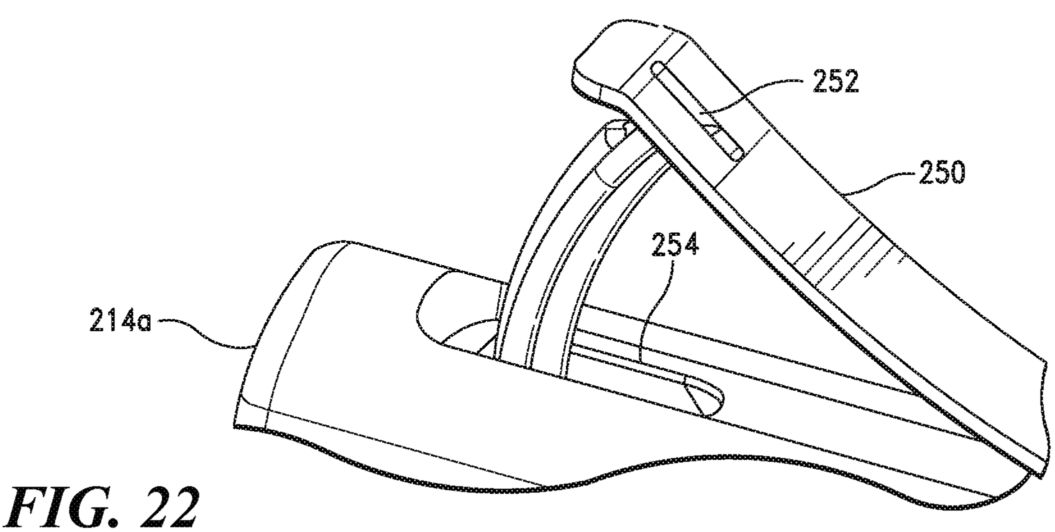
FIG. 22 is a perspective view of the jaw mechanism shown in FIG. 20 with the needle shield in the deflected state, showing a window feature in the needle shield to prevent damage to the tubular needle distal end when the needle is extended into the needle shield, in accordance with the invention.

Referring now to FIGS. 20-22, when the tubular needle 116 is slidably translated through the guide channel 218*b* and into the window 254 of the jaw mechanism 212 top jaw member 214*a*, the tubular needle 116 is guided into needle shield 250. As illustrated in FIG. 20, in a preferred embodiment, the needle shield 250 comprises a deflecting trapdoor mechanism that is configured to prevent the tubular needle 116 from penetrating soft tissue and bone beyond the top jaw member 214*a* and damaging the soft tissue and bone. In a preferred embodiment, the needle shield 250 is configured to deflect and flex when the tubular needle 116 distal end 120 is slidably translated into the needle shield 250.

In a preferred embodiment, the needle shield 250 of the jaw mechanism 212 top jaw member 214*a* enables antegrade and retrograde passing of suture 71 during an endoscopic procedure, which allows an operator to generate a wide variety of stitch patterns in soft tissue including, without limitation, modified Mason-Allen, mattress, sliding mattress, Mason-Allen, far-near-near-far, Bunnell-Mayer, three-loop pulley, locking loop, modified Kessler, simple interrupted, simple continuous, Ford interlocking, interrupted cruciate, interrupted horizontal mattress, continuous horizontal mattress, interrupted vertical mattress, quilled, interrupted or continuous Lembert, interrupted quilt, Cushing, Connel, Parker-Kerr, purse string and modified variants thereof.

In some embodiments, the needle shield 250 is configured to provide a closure force that captures the suture 71 when the tubular needle 116 is retracted and the needle shield 250 is relieved from the force applied to the needle shield 250 by slidable translation of the tubular needle 116.

As illustrated in FIGS. 20-22, in a preferred embodiment, the needle shield 250 comprises a window member 252 that is configured to protect the distal end 120 of tubular needle 116 from damage. According to the invention, the needle shield 250 can comprise other features to protect the distal end 120 of tubular needle 116, such as a coined recess or other geometry that is configured to receive the distal end 120 of tubular needle 116 without damaging the distal end 120.

According to the invention, the window member 252 can comprise any shape or size suitable to receive the distal end 120 of tubular needle 116 without damaging the distal end 120.

Figure 23:
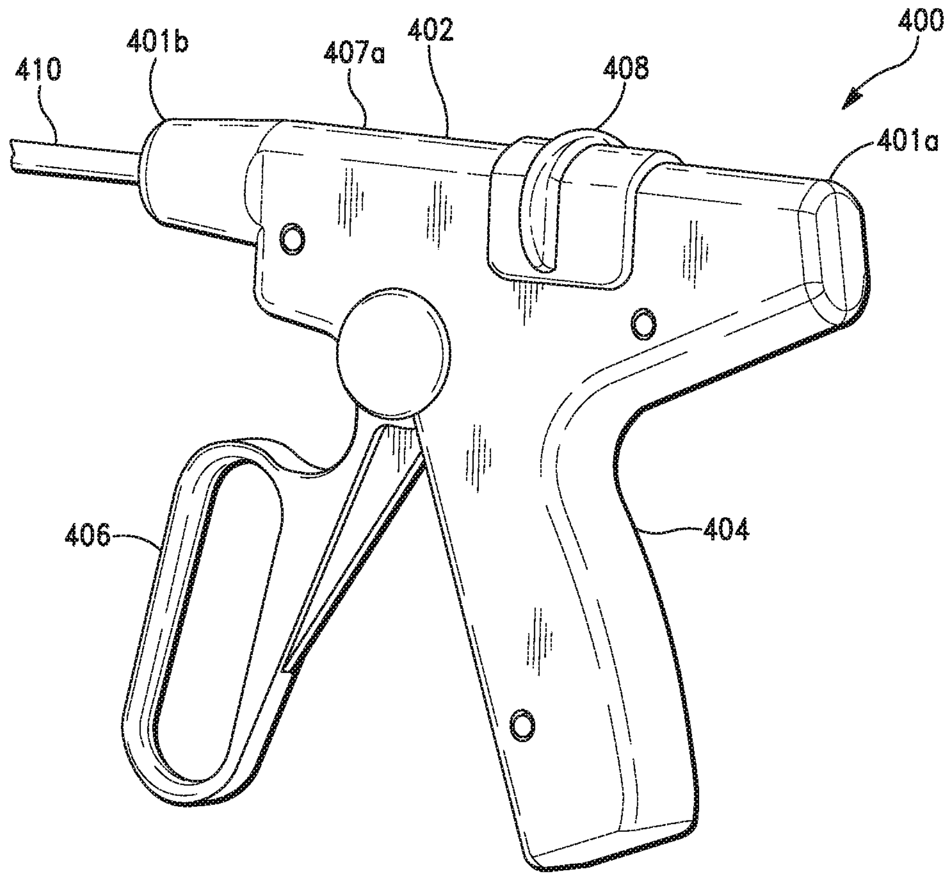
FIG. 23 is a perspective view of another embodiment of the suture passing system actuator, in accordance with the invention.
Figures 24A, 24B:
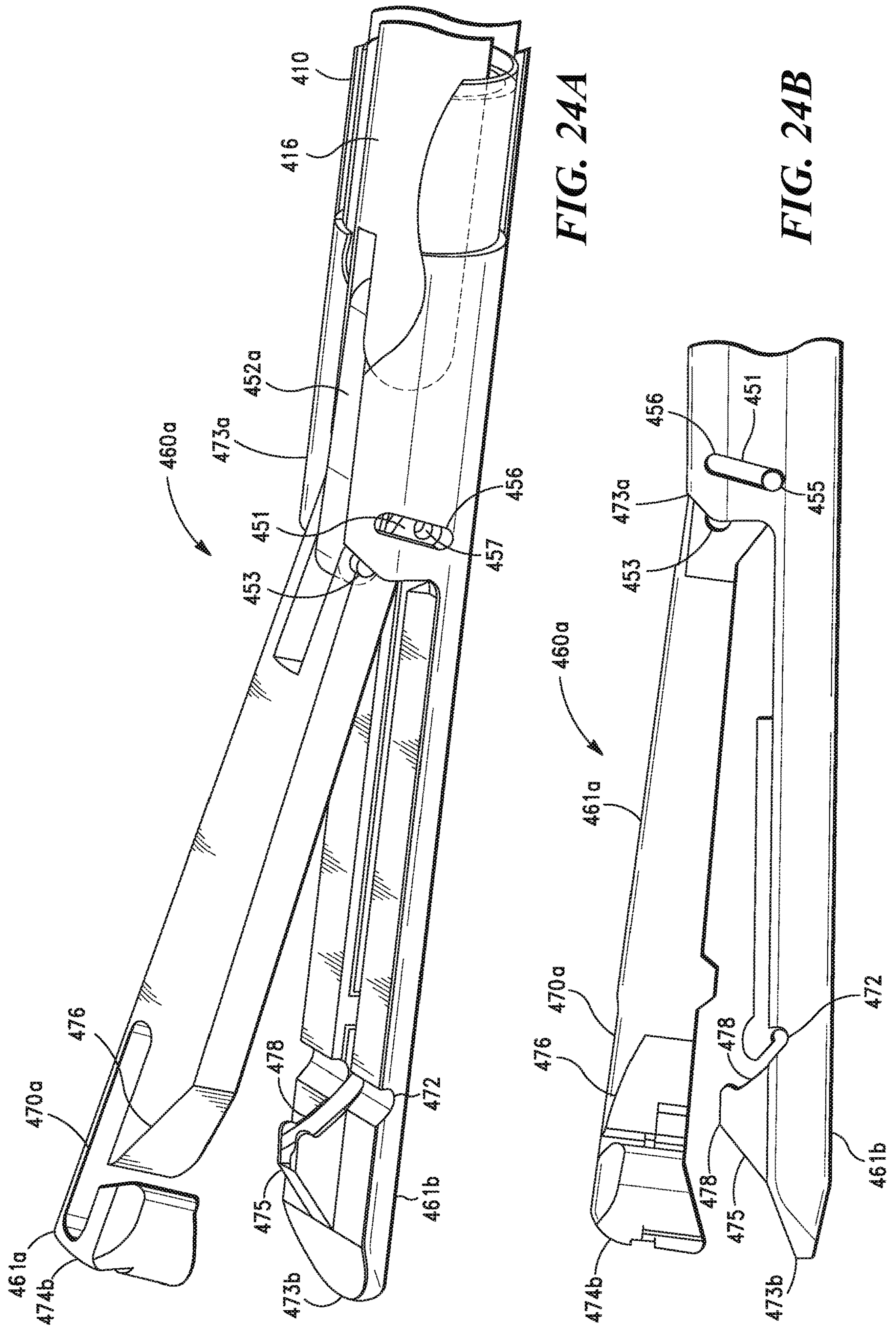
FIG. 24A is a perspective view of another embodiment of a jaw mechanism, in accordance with the invention.
FIG. 24B is a partial side plan view of the jaw mechanism shown in FIG. 24A, in accordance with the invention.
Figures 24C, 24D:
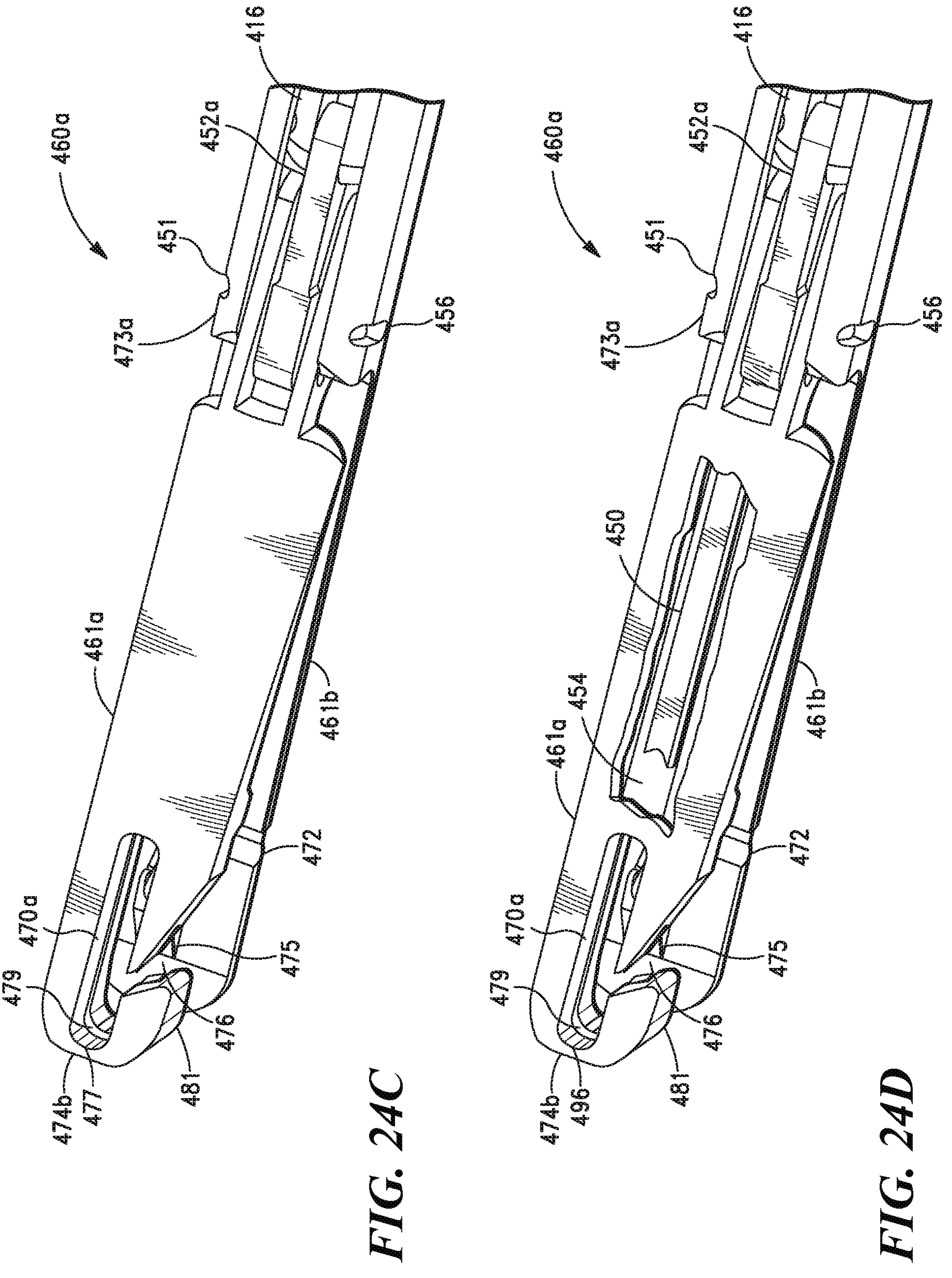
FIG. 24C is a partial top plan view of the jaw mechanism shown in FIG. 24A, in accordance with the invention.
FIG. 24D is a further partial top plan view of the jaw mechanism shown in FIG. 24A, having a cut away section showing a top jaw member ribbon track and a suture retaining ribbon positioned therein, in accordance with the invention.
Figure 24E:
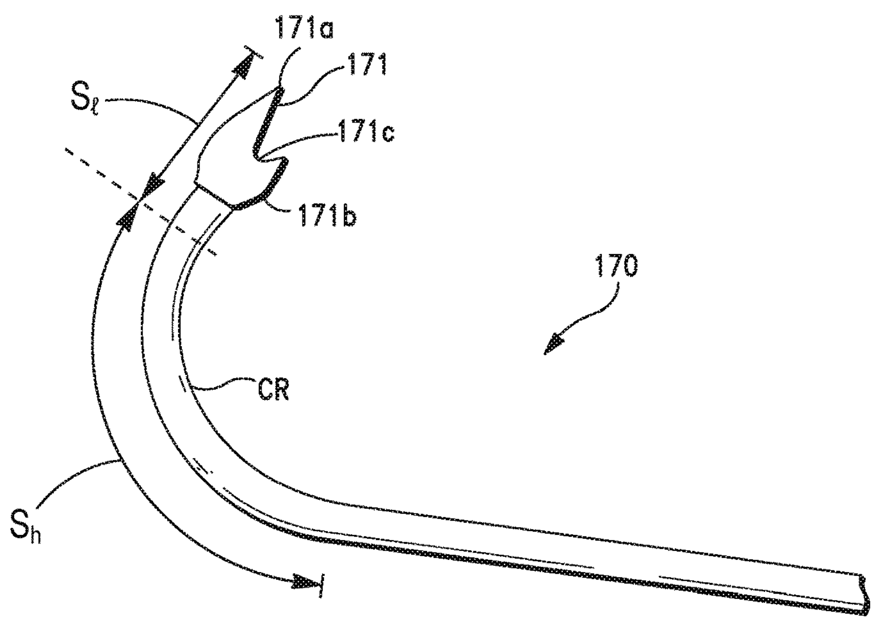
FIG. 24E is a partial perspective view of another embodiment of a system needle, in accordance with the invention.
Figure 24F:
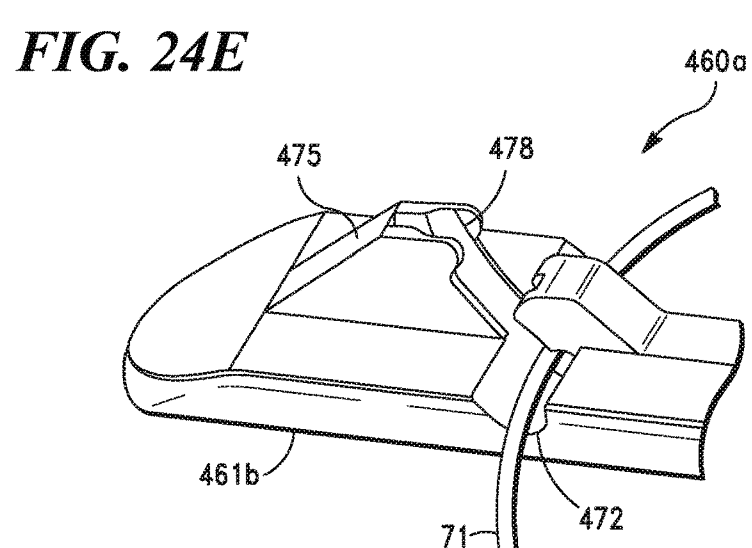
FIG. 24F is a partial perspective view of a bottom jaw member of the jaw mechanism shown in FIG. 24A, showing a suture positioned thereon, in accordance with the invention.
Figure 24G:
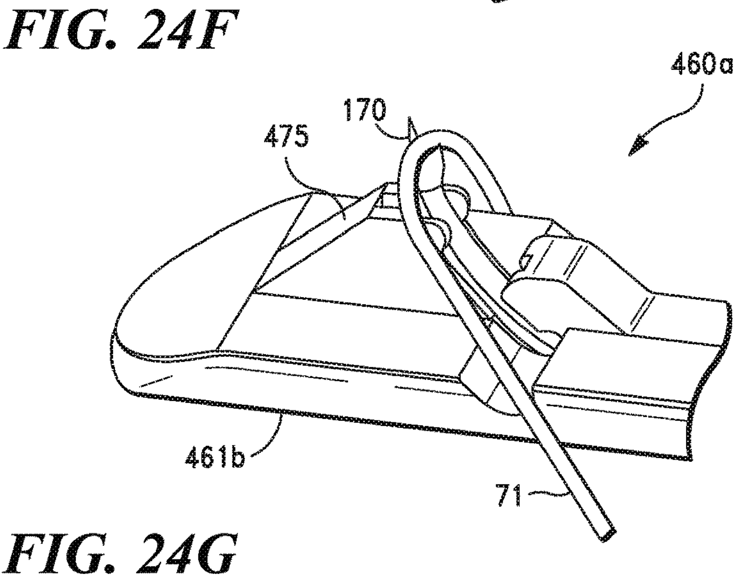
FIG. 24G is a further partial perspective view of the bottom jaw member FIG. 24F, showing the suture captured by the system needle shown in FIG. 24E, in accordance with the invention.
Figure 25:
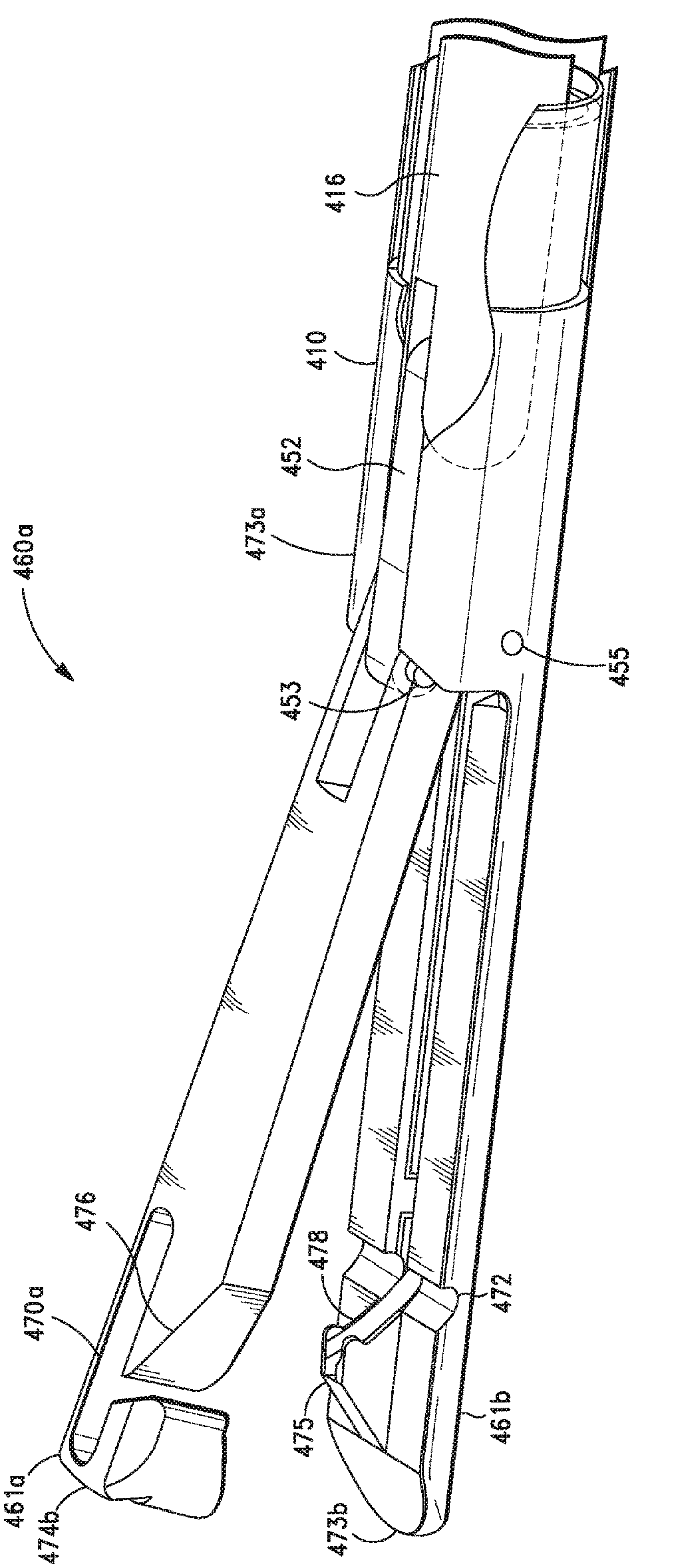
FIG. 25 is a partial perspective view of another embodiment of a jaw mechanism comprising one embodiment of a fixed pivot mechanism, in accordance with the invention.

Referring now to FIGS. 23-25, there is shown another embodiment of a suture passing system of the invention (denoted "400").

As illustrated in FIGS. 23 and 24A, the suture passing system 400 similarly comprises a body 402, comprising proximal and distal ends 401*a*, 401*b*, a handle 404, a trigger 406, and an elongated member or shaft 410 that similarly comprises a jaw mechanism (denoted "460*a*" in this embodiment), which is adapted to grasp soft tissue.

As illustrated in FIGS. 24A and 24B, the jaw mechanism 460*a* similarly comprises top and bottom jaw members 461*a*, 461*b*. As further illustrated in FIGS. 24A and 24B, the bottom jaw member 461*b* similarly comprises a guide channel 478 that is configured to receive a needle of the invention; preferably, needle 170 illustrated in FIG. 24E and discussed below, therein, and a suture loading slot 472 that similarly allows a suture 71, to be loaded therein from either lateral side of the jaw mechanism 460*a*, as illustrated in FIG. 24F, whereby the suture 71 can be engaged by the needle 170 as it slidably translates through the guide channel 478, as illustrated in FIG. 24G.

Referring now to FIG. 24E, there is shown a plan view of needle 170. As illustrated in FIG. 24E, the needle 170 comprises a suture ensnarement end 171 comprising a soft tissue piercing region 171*a* and a suture ensnarement and retaining region 171*b*, which is adapted to ensnare and releasably engage a suture, such as suture 71.

As further illustrated in FIG. 24E, the suture piercing region 171*a* and the suture retaining region 171*b* form a suture seat or notch 171*c* therebetween, which, as illustrated in FIG. 24G, is configured and adapted to seat a suture therein.

As additionally illustrated in FIG. 24E, in a preferred embodiment, the needle 170 further comprises a curvilinear region (denoted "CR") comprising a first radius.

In some embodiments, the curvilinear region CR further comprises a second radius.

In a preferred embodiment, the needle guide channel 478 (described below) induces, and the needle 170 thus comprises, multiple strain regions, i.e., regions of the needle comprising different strain values, when the needle 170 is disposed and articulates in the needle guide channel 478, which include a "high strain" region (denoted "$S_h$") proximate curvilinear region CR of the needle 170 and a "low strain" region (denoted "$S_l$") proximate the suture ensnarement end 171 of needle 170.

By the phrase "low strain region" as used herein in connection with needle 170, it is meant to mean that the needle 170 exhibits a strain value at the low strain region $S_l$ that is lower than the strain value at the high strain region $S_h$ when the needle 170 is disposed and articulates in the needle guide channel 478 of the bottom jaw member 461*b* (and bottom jaw member 462*b*, discussed below).

As illustrated in FIGS. 24B and 24C, in a preferred embodiment, the top jaw member 461*a* of the jaw mechanism 460*a* comprises a side wall opening 476 and hook 481, which facilitates suture capture in a surgical site.

As further illustrated in FIG. 24B, in a preferred embodiment, the bottom jaw member 461*b* comprises a raised distal guide region 475 proximate the distal end 473*b* of the bottom jaw member 461*b*, and the top jaw member 461*a* comprises side wall opening 476, which is sized and configured to restrict access of a suture, e.g., suture 71, into the jaw mechanism 460*a* from the distal 474*b* thereof and, hence, further facilitate suture capture from a lateral side of the jaw mechanism 460*a*.

As further illustrated in FIGS. 24A and 24B, in one embodiment, the jaw mechanism 460*a* further comprises the aforementioned floating pivot mechanism (denoted "451").

In the noted embodiment, the floating pivot mechanism 451 thus comprises a first pin 453, which is sized and configured to be positioned in a first pin lumen (not shown) in the top jaw member 461*a*, a second pin 455, which is sized and configured to be positioned in a second pin lumen 457 in the top jaw member 461*a*, a third pin lumen in link 452*a*, and a floating pin slot 456 in the bottom jaw member 461*b*.

According to the invention, the floating pivot mechanism 451 operates in a similar manner and provides the same features and advantages as the floating pivot mechanism illustrated in FIGS. 8A and 8C and discussed above.

Referring now to FIG. 25, in some embodiments, the jaw mechanism 460*a* comprises a simple pin 453 that defines a pivot point, wherein the top and bottom jaw members 461*a*, 461*b* are in pivotal communication and the top jaw member 461*a* axially articulates with respect to the bottom jaw member 461*b*.

As set forth in priority U.S. application Ser. No. 18/623,903, now U.S. Pat. No. 12,390,213, suture passing system 400 also comprises the following control systems: (i) a jaw articulation control system that is adapted to modulate articulation of jaw mechanism 460*a*, (ii) a needle articulation control system that is adapted to modulate translation and articulation of needle 170, and a suture control system that is adapted to modulate engagement, retainment and release of suture 71.

As further set forth in U.S. application Ser. No. 18/623,903, the suture passing system 400 also comprises a multi-function actuation system that is configured to control the jaw articulation control system, needle articulation control system and suture control system.

The preferred multi-function actuation system (denoted "405") is configured to provide the following synchronized functions during a single continuous rotational (or angular) articulation of a system trigger (denoted 406) from a default position, i.e., 0° rotation, to a fully actuated position: (i) articulation of the system jaw mechanism 460*a*, (ii) suture control, i.e., suture engagement, retainment and release, by the jaw mechanism 460*a*, and (iii) translation and positioning of the system needle 170. The multi-function actuation system 405 is also configured to provide the same functions in reverse order during continuous rotational articulation of the system trigger 406 from the fully actuated position to the default position, i.e., upon release of the trigger 406.

Referring now to FIGS. 26A-26Z, 28A-281, 29A-29D, 30A-30E, and 31A-31D, there are shown several embodiments of "multi-function" jaw mechanisms of the invention.

As discussed in detail below, in addition to facilitating effective grasping, approximation, ligation and fixation of a myriad of soft tissues having a wide range of thicknesses and structure variations without collateral damage to extraneous soft tissue and bone structures, the multi-function jaw mechanisms of the invention are designed, configured and adapted to facilitate multiple seminal surgical functions, including highly effective and efficient means for (i) uncomplicated and highly reliable suture loading and retrieval with minimal visual guidance, (ii) optimal suture manipulation and retrieval in soft tissue in a confined surgical site, (iii) stitch placement measurement and positions in soft tissue in a confined surgical site for accurate and precise provision of complex stitch patterns, such as modified Mason-Allen stitch patterns, and (iv) grasping, capturing and engaging sutures, soft tissue, and surgical instruments (and devices) in a confined surgical site with minimal visual guidance.

Additional advantages of the multi-function jaw mechanisms, which are also discussed below, include unique needle wear resistance means that increases the durability and longevity of a needle employed with the jaw mechanisms and a needle protection means that prevents breakage of the needle when subjected to high strain during a surgical procedure.

Figure 26A:
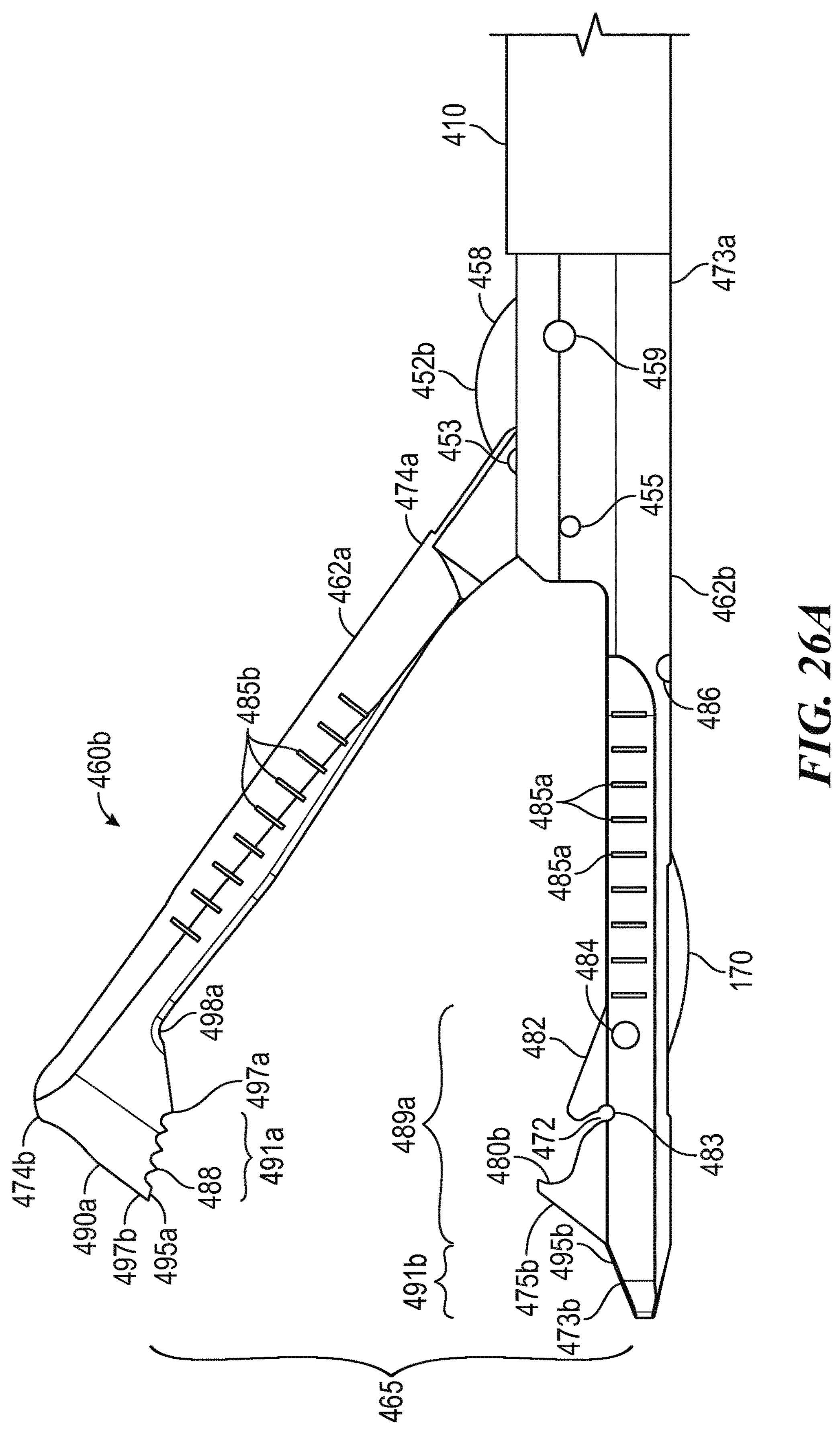
FIG. 26A is a side plan view of a multi-function jaw mechanism in a fully open jaw configuration, in accordance with the invention.
Figure 26B:
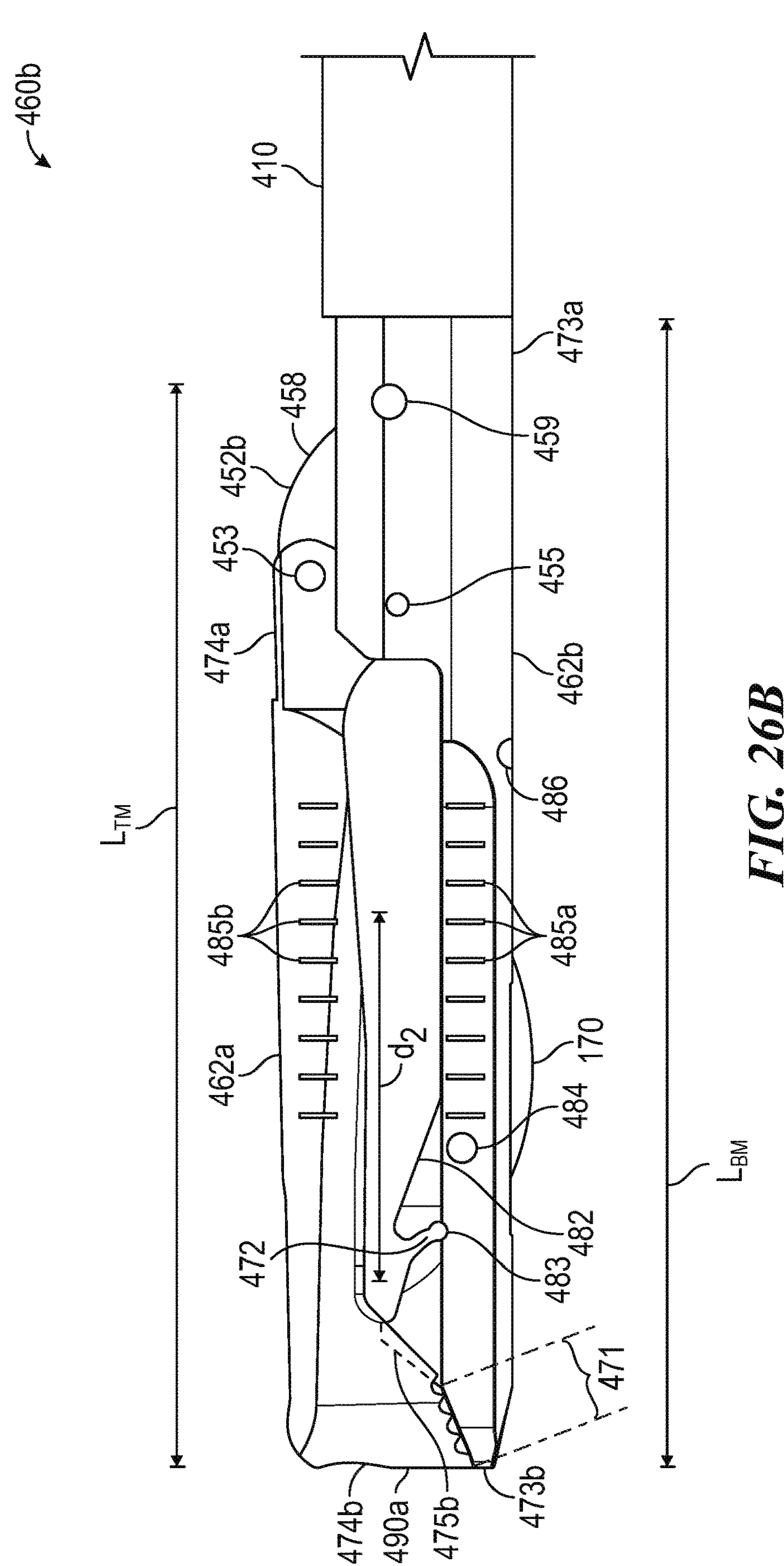
FIG. 26B is a further side plan view of the multi-function jaw mechanism shown in FIG. 26A in a fully closed jaw configuration, in accordance with the invention.

Referring first to FIGS. 26A and 26B, there is shown one embodiment of a multi-function jaw mechanism of the invention (denoted "460*b*").

As illustrated in FIGS. 26A and 26B, the multi-function jaw mechanism 460*b* (and multi-function jaw mechanisms 460*c*, 460*d*, 460*e*, 460*f* illustrated in FIGS. 28A-28I, 29A-29D, 30A-30E, and 31A-31D and discussed below) similarly comprises top and bottom jaw members, in this instance, denoted 462*a* and 462*b*, respectively.

In a preferred embodiment, the multi-function jaw mechanism 460*b* (and multi-function jaw mechanisms 460*c*, 460*d*, 460*e*, 460*f*) also comprises a fixed pivot mechanism 458 that allows the jaw mechanisms 460*b*, 460*c*, 460*d*, 460*e*, 460*f* to transition from a default fully open configuration, as described above and illustrated in FIG. 26A, which, as discussed below, facilitates receipt of sutures, soft tissue, and surgical instruments and devices in the open jaw mechanism region (denoted "465" in FIG. 26A and also referred to hereinafter as the "internal jaw region"), to a closed configuration, as illustrated in FIG. 26B, and back to the default open configuration via a jaw articulation control system of the invention.

In a preferred embodiment, the fixed pivot mechanism 458 also allows the jaw mechanisms 460*b*, 460*c*, 460*d*, 460*e*, 460*f* to transition from the fully open jaw configuration and closed jaw configuration to a partially open jaw configuration.

Figure 26C:
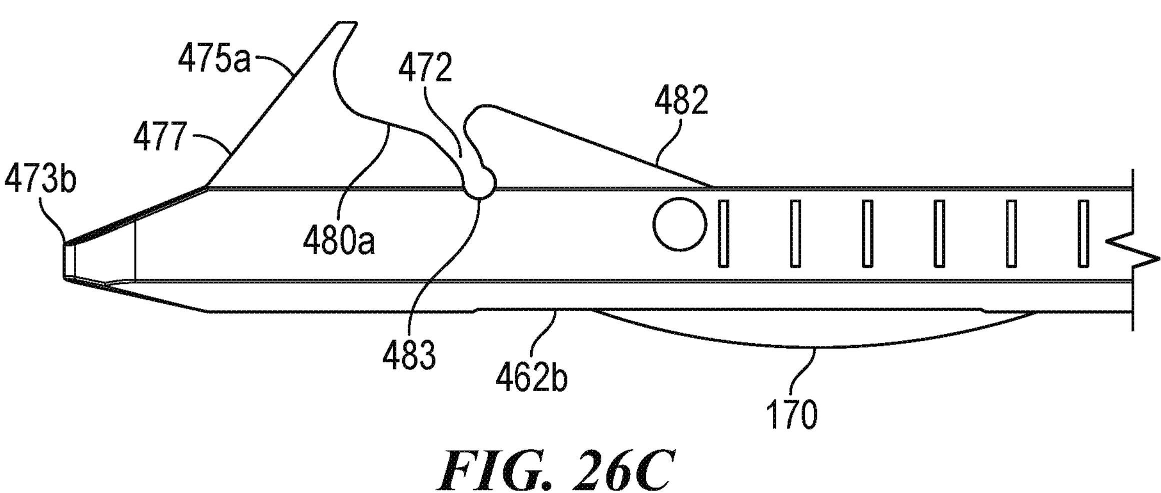
FIG. 26C is a partial side plan view of the bottom jaw member of the multi-function jaw mechanism shown in FIG. 26A, showing an embodiment of a raised distal guide region of the bottom jaw member, in accordance with the invention.
Figure 26D:
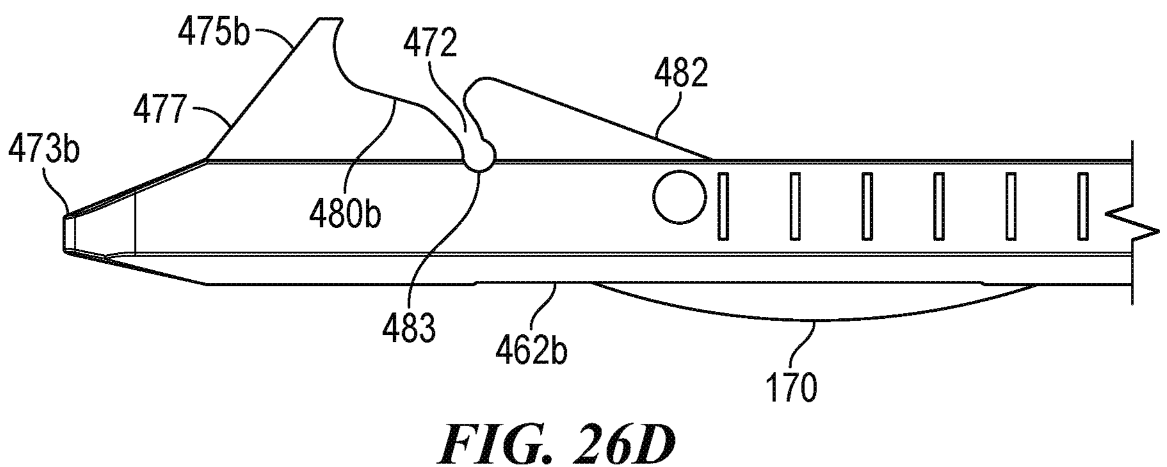
FIG. 26D is a further partial side plan view of the bottom jaw member of the multi-function jaw mechanism shown in FIG. 26A, showing another embodiment of a raised distal guide region of the bottom jaw member, in accordance with the invention.
Figure 26E:
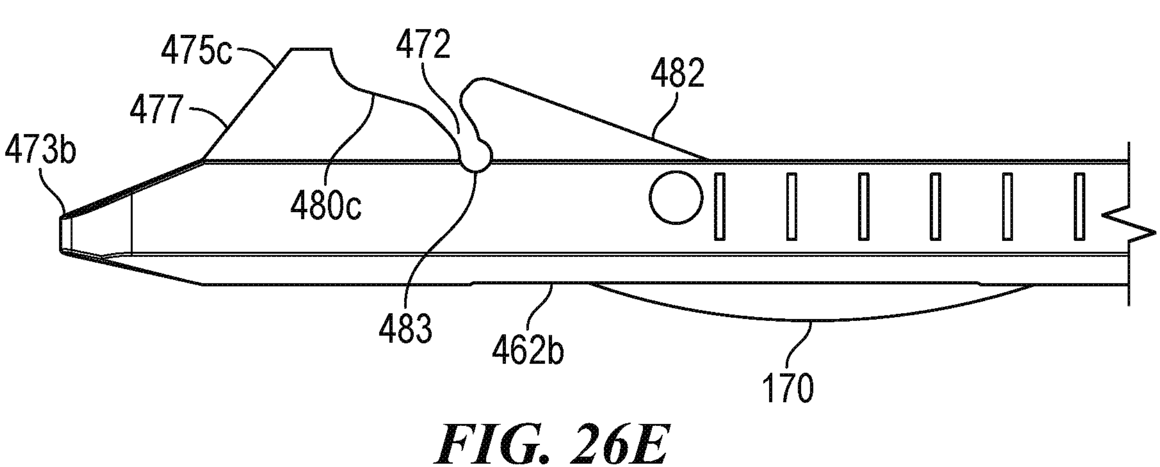
FIG. 26E is a further partial side plan view of the bottom jaw member of the multi-function jaw mechanism shown in FIG. 26A, showing another embodiment of a raised distal guide region of the bottom jaw member, in accordance with the invention.
Figure 26F:
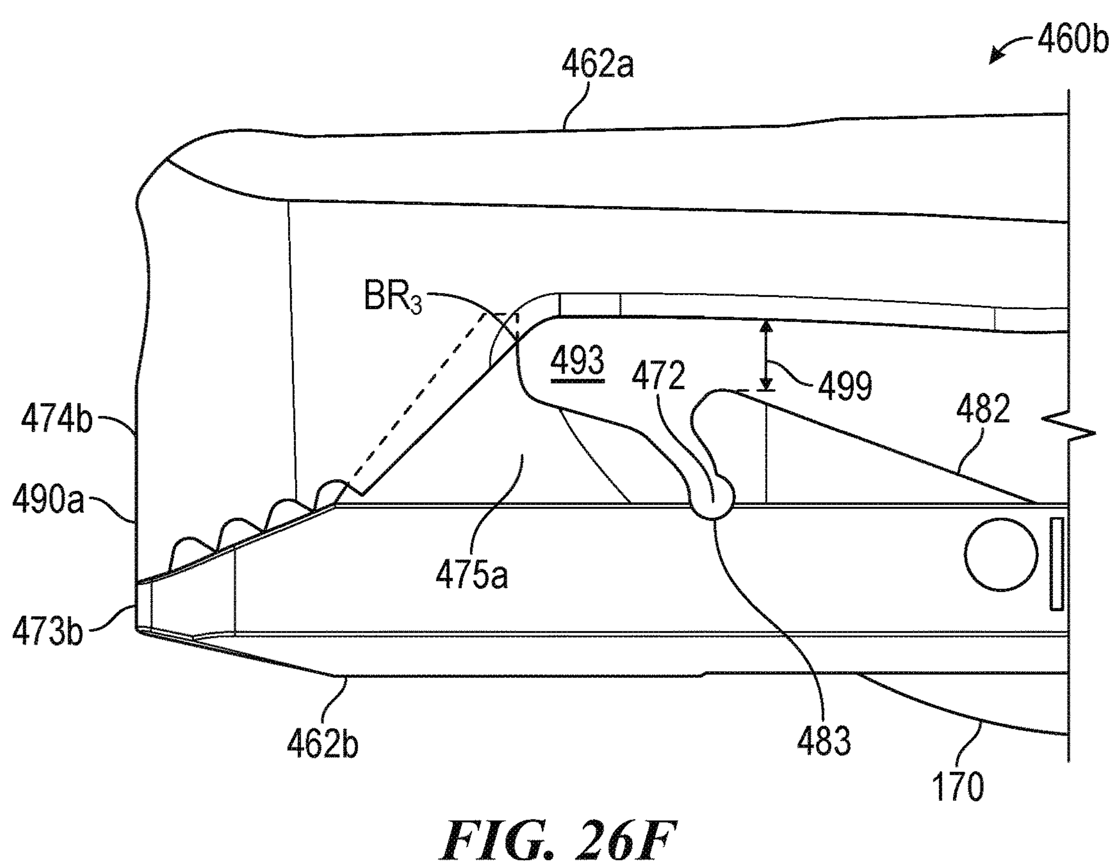
FIG. 26F is a partial side plan view of the multi-function jaw mechanism shown in FIG. 26B, showing the raised distal guide region of the bottom jaw member shown in FIG. 26C seated in the top jaw member of the multi-function jaw mechanism, in accordance with the invention.
Figure 26G:
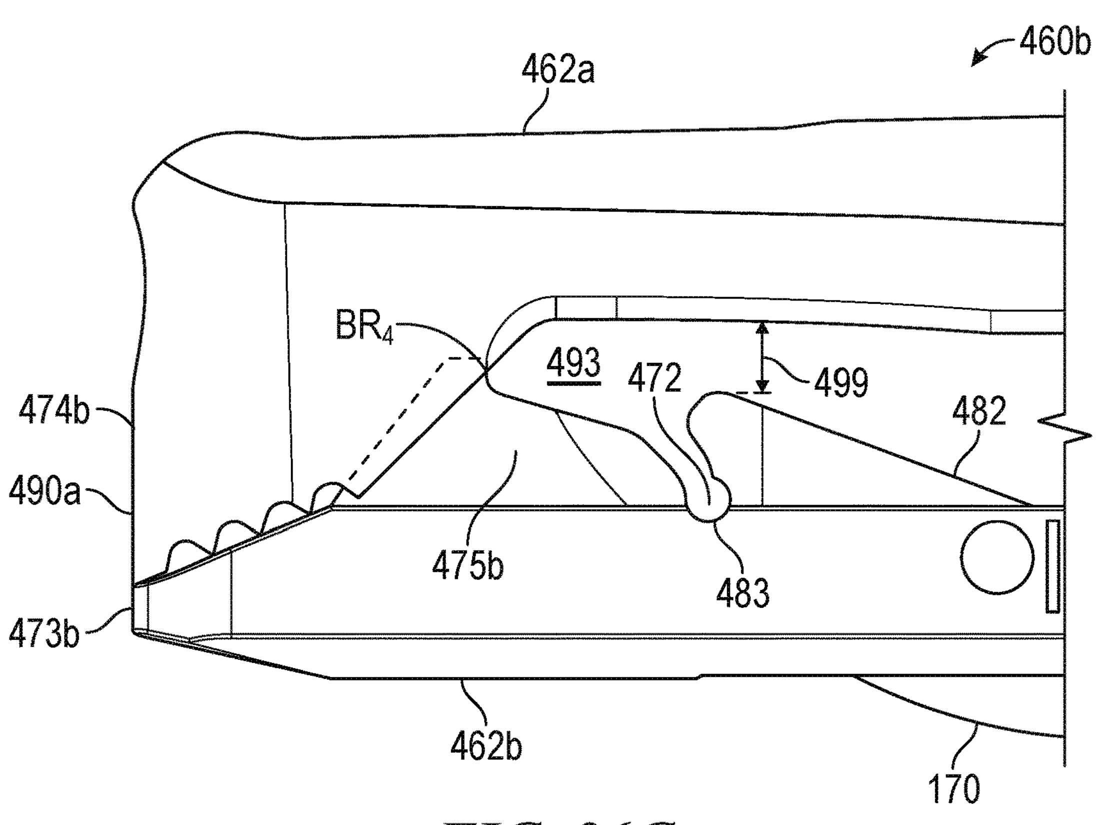
FIG. 26G is a partial side plan view of the multi-function jaw mechanism shown in FIG. 26B, showing the raised distal guide region of the bottom jaw member shown in FIG. 26D seated in the top jaw member of the multi-function jaw mechanism, in accordance with the invention.
Figure 26H:
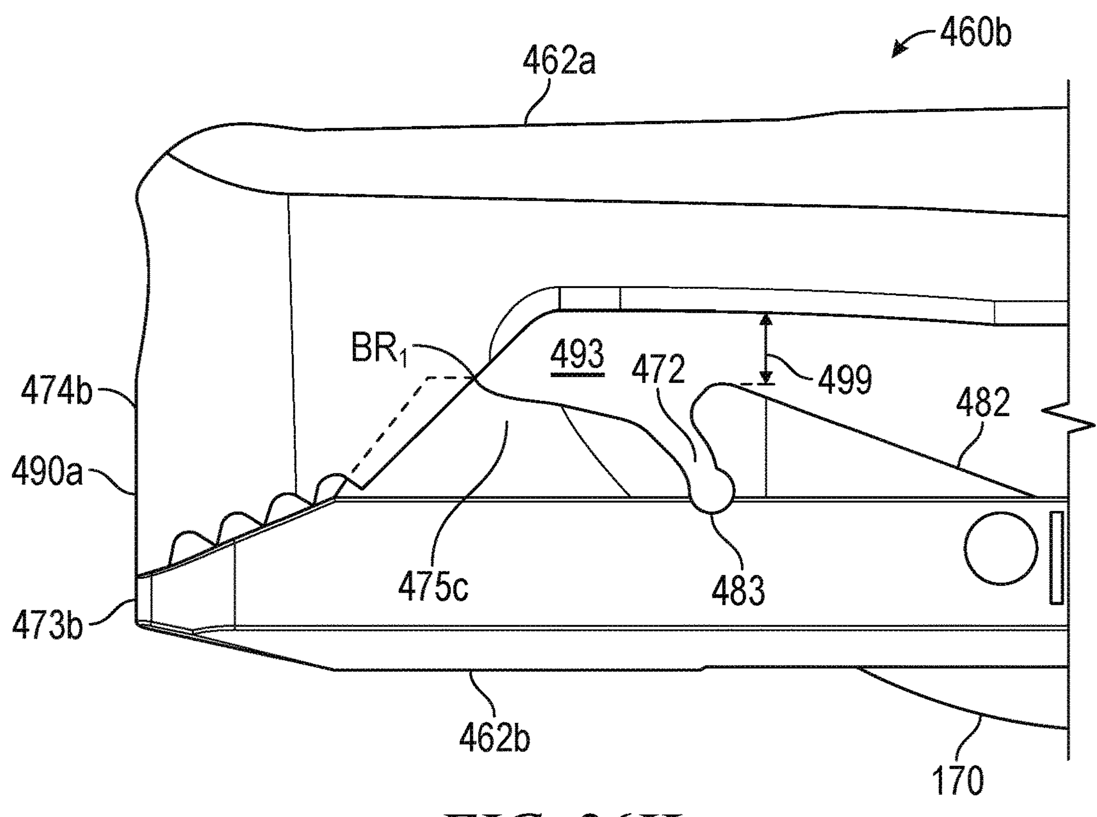
FIG. 26H is a partial side plan view of the multi-function jaw mechanism shown in FIG. 26B, showing the raised distal guide region of the bottom jaw member shown in FIG. 26E seated in the top jaw member of the multi-function jaw mechanism, in accordance with the invention.
Figure 26I:
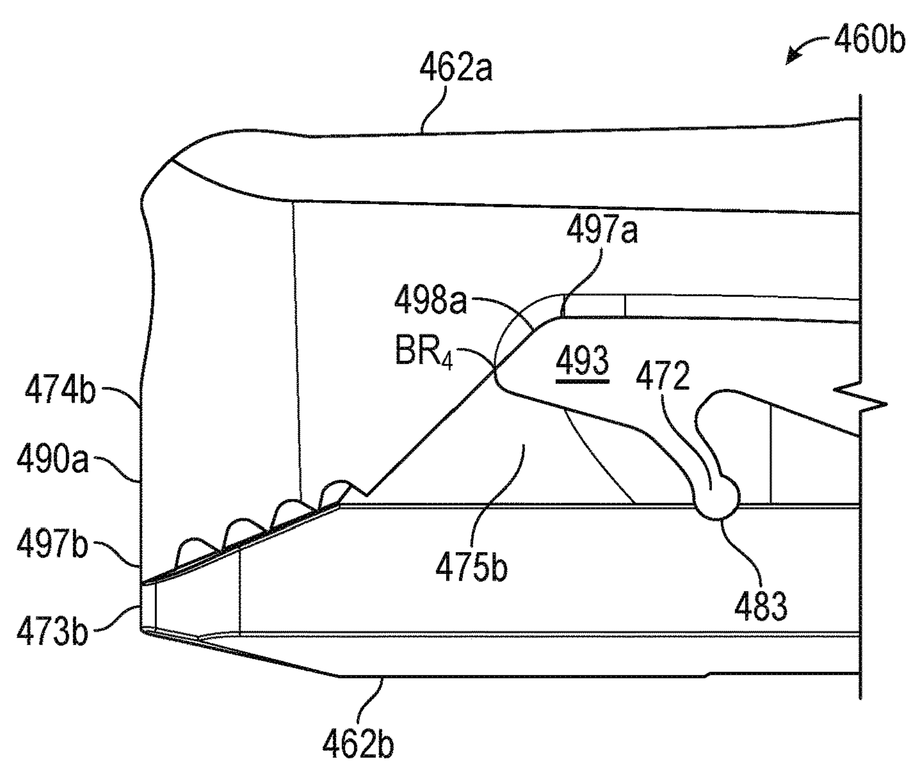
FIG. 26I is a partial side plan view of the multi-function jaw mechanism shown in FIG. 26B, showing one embodiment of a suture backstop region of the multi-function jaw mechanism, in accordance with the invention.
Figure 26J:
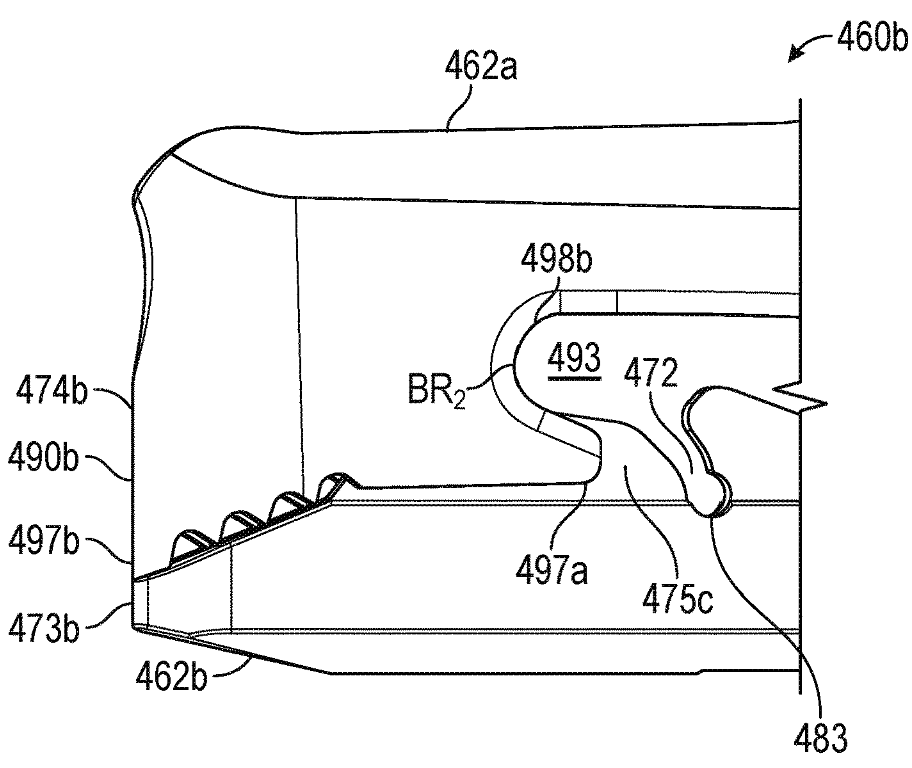
FIG. 26J is a partial side plan view of the multi-function jaw mechanism shown in FIG. 26B, showing another embodiment of a suture backstop region of the multi-function jaw mechanism, in accordance with the invention.
Figure 26K:
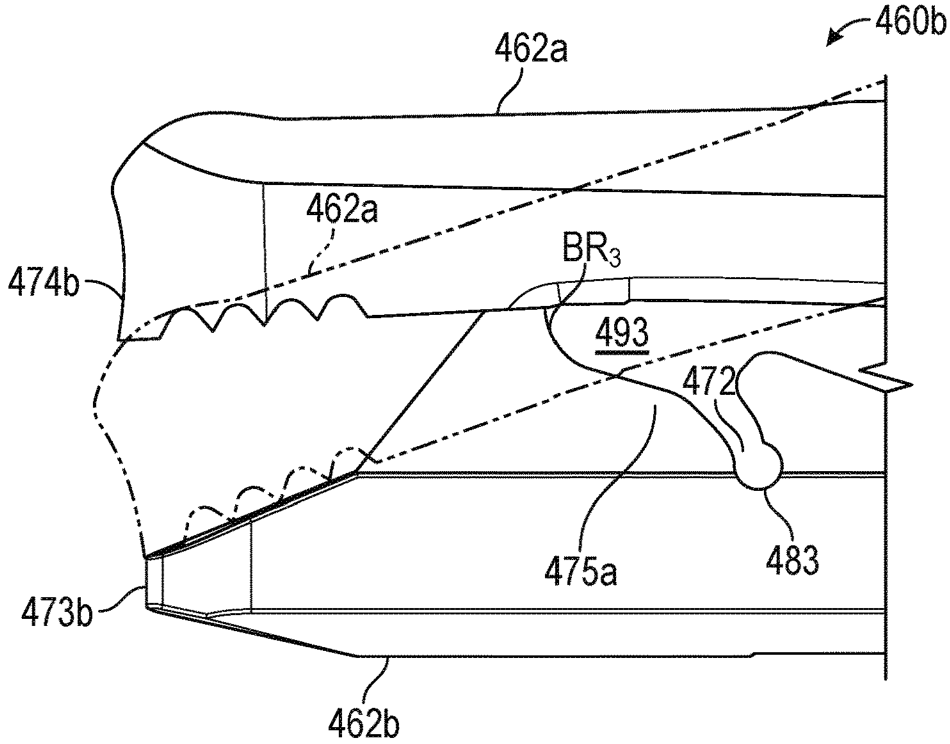
FIG. 26K is a partial side plan view of the multi-function jaw mechanism shown in FIG. 26B, showing another embodiment of a suture backstop region of the multi-function jaw mechanism, in accordance with the invention.
Figures 26L, 26M, 26N:
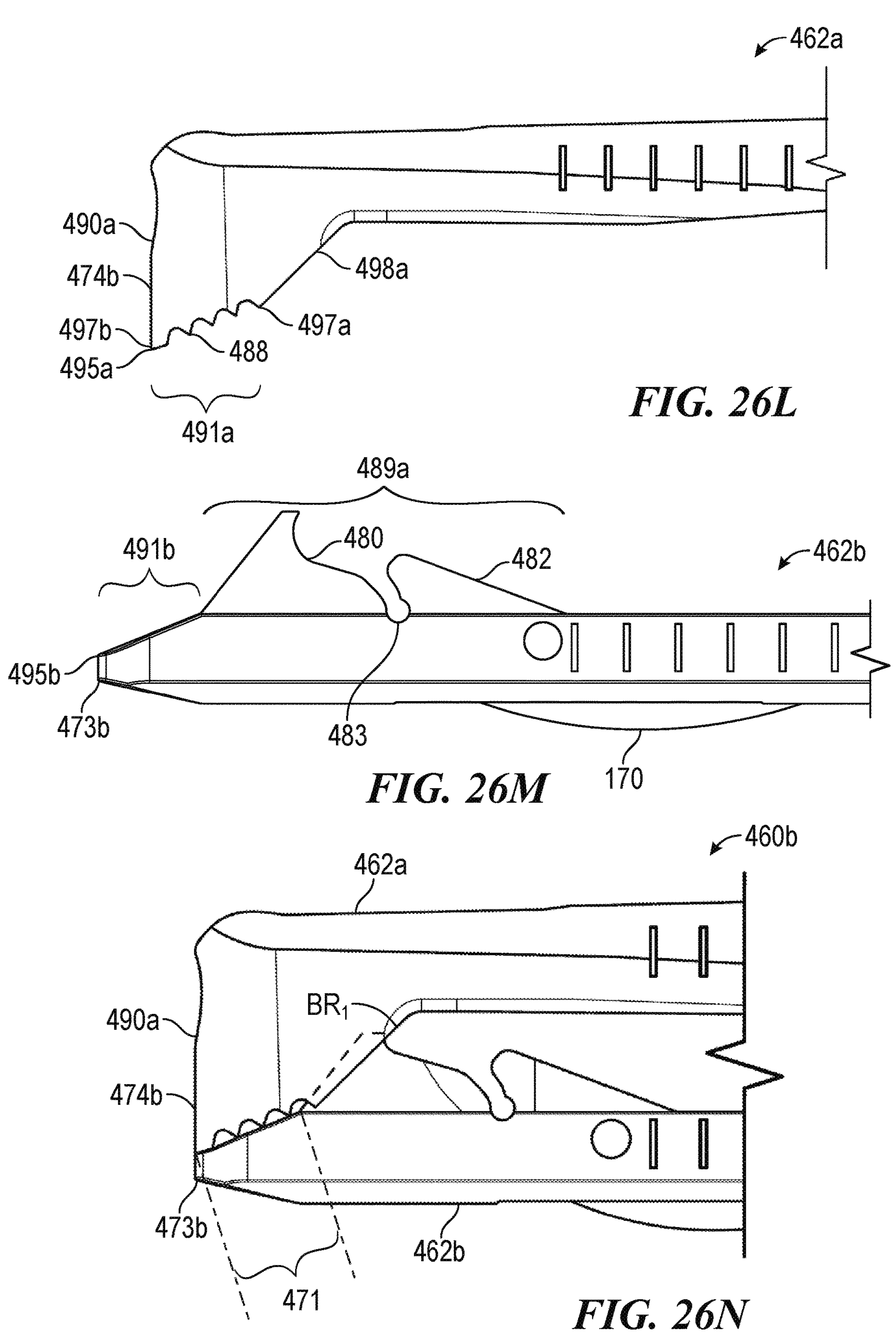
FIG. 26L is a partial side plan view of the top jaw member of the multi-function jaw mechanism shown in FIG. 26A, in accordance with the invention.
FIG. 26M is a partial side plan view of the bottom jaw member of the multi-function jaw mechanism shown in FIG. 26A, in accordance with the invention.
FIG. 26N is a partial side plan view of the multi-function jaw mechanism shown in FIG. 26B, in accordance with the invention.
Figure 26O:
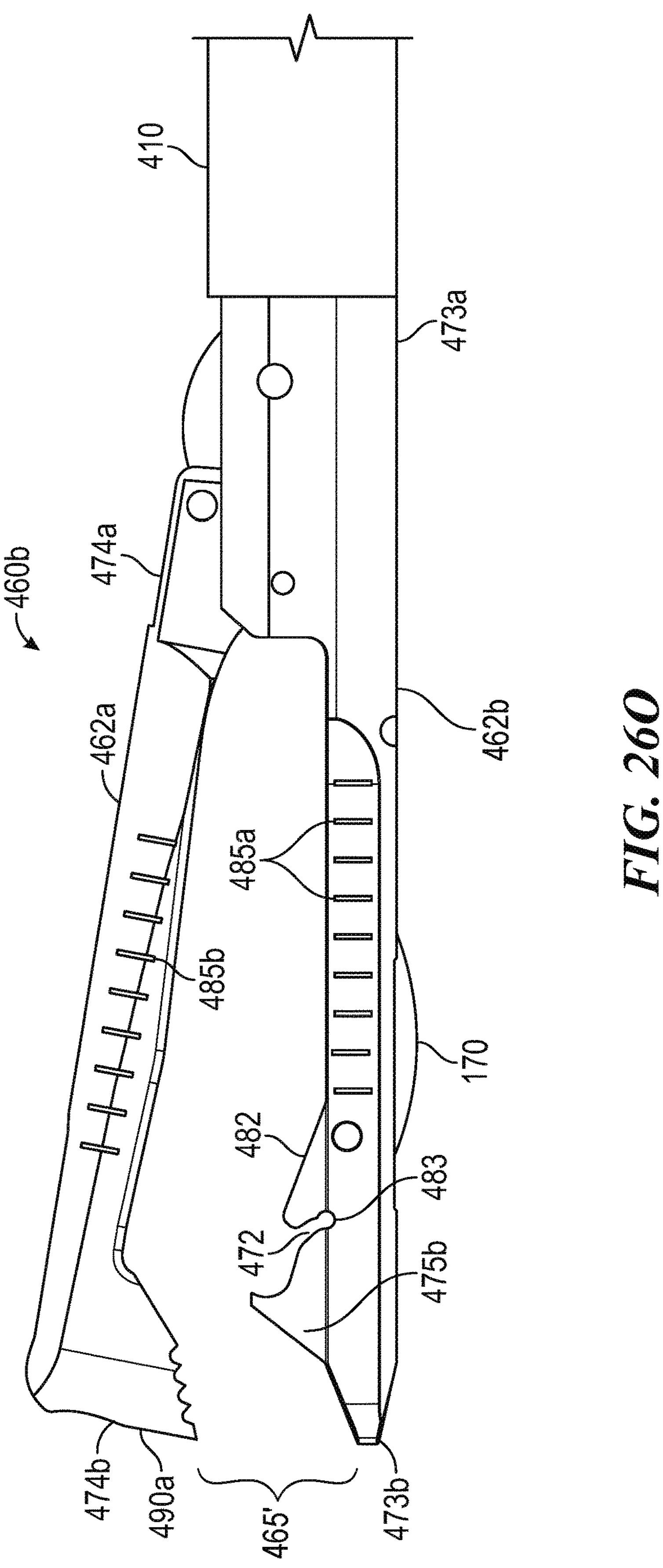
FIG. 26O is a further side plan view of the multi-function jaw mechanism shown in FIG. 26A in a partially open jaw configuration, in accordance with the invention.
Figure 26P:
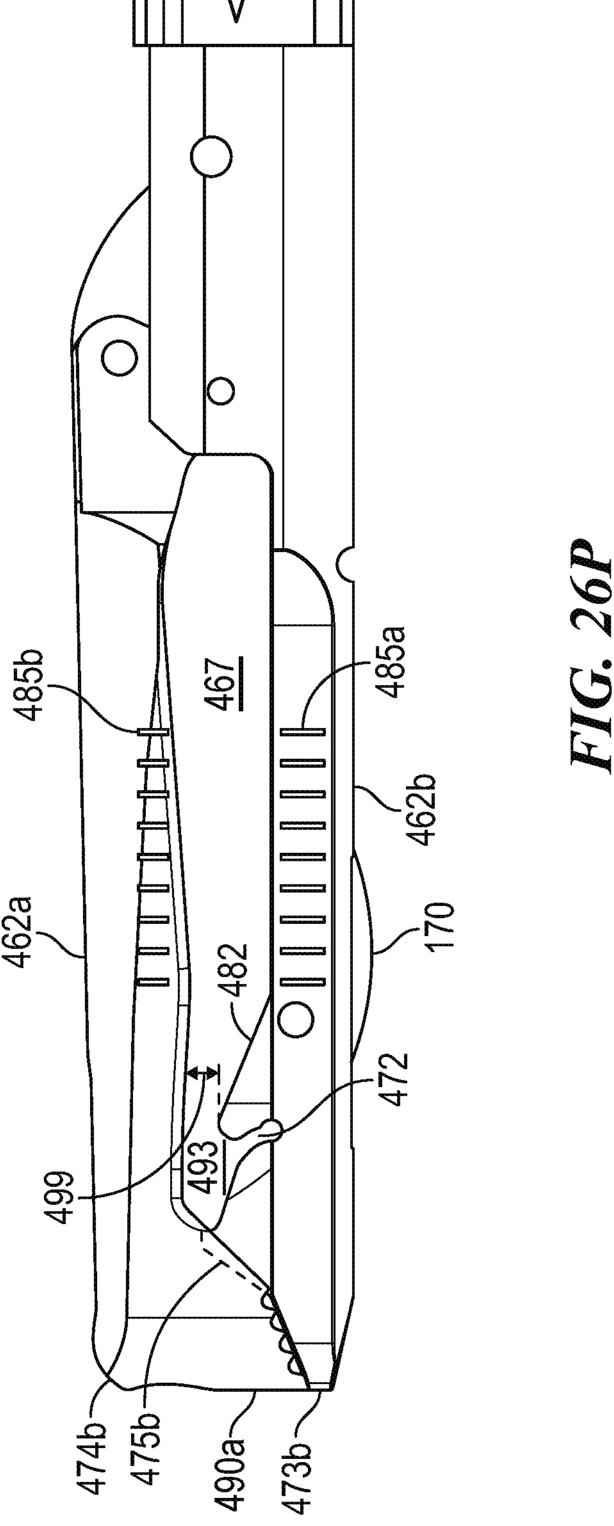
FIG. 26P is further side plan view of the multi-function jaw mechanism shown in FIG. 26B, showing the gap formed between the top jaw member and suture engagement region of the bottom jaw member, when the multi-function jaw mechanism is in a closed jaw configuration, in accordance with the invention.
Figure 26Q:
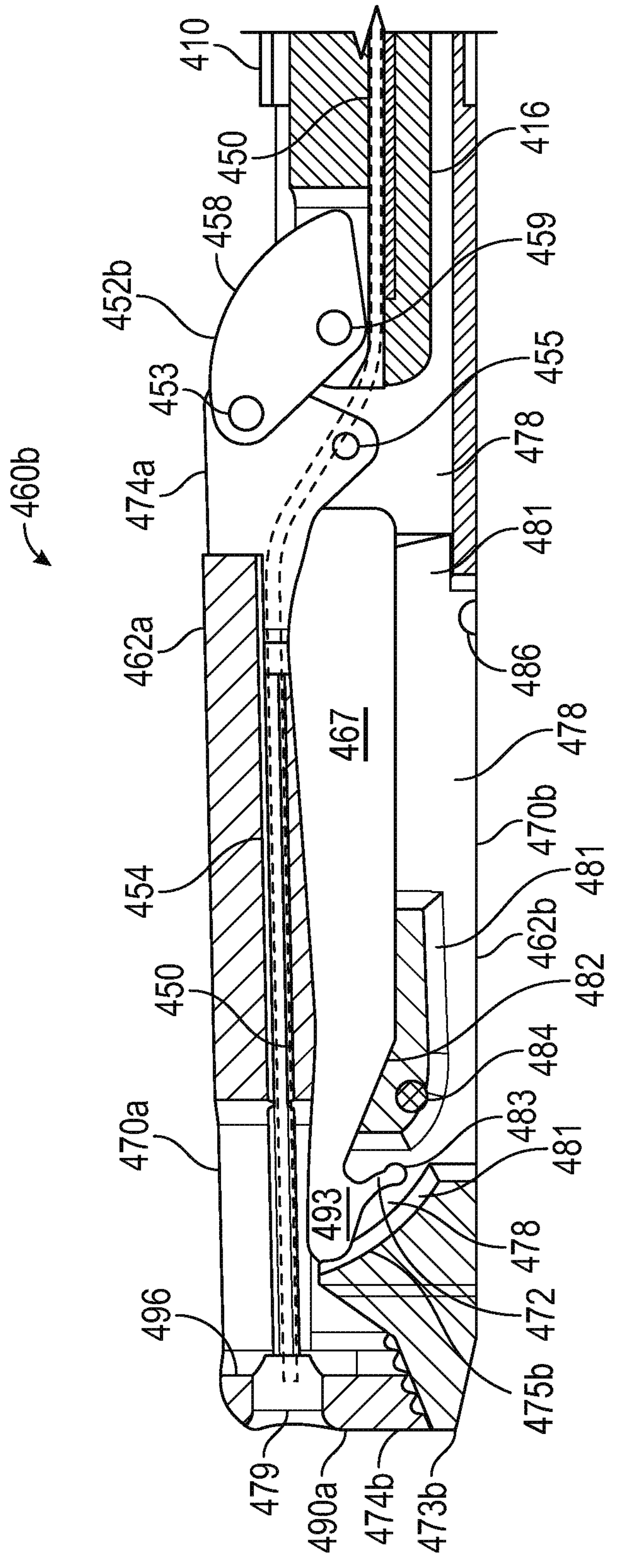
FIG. 26Q is a side plan sectional view of the multi-function jaw mechanism shown in FIG. 26B, showing the open needle guide channel and track in the lower jaw member, in accordance with the invention.
Figure 26R:
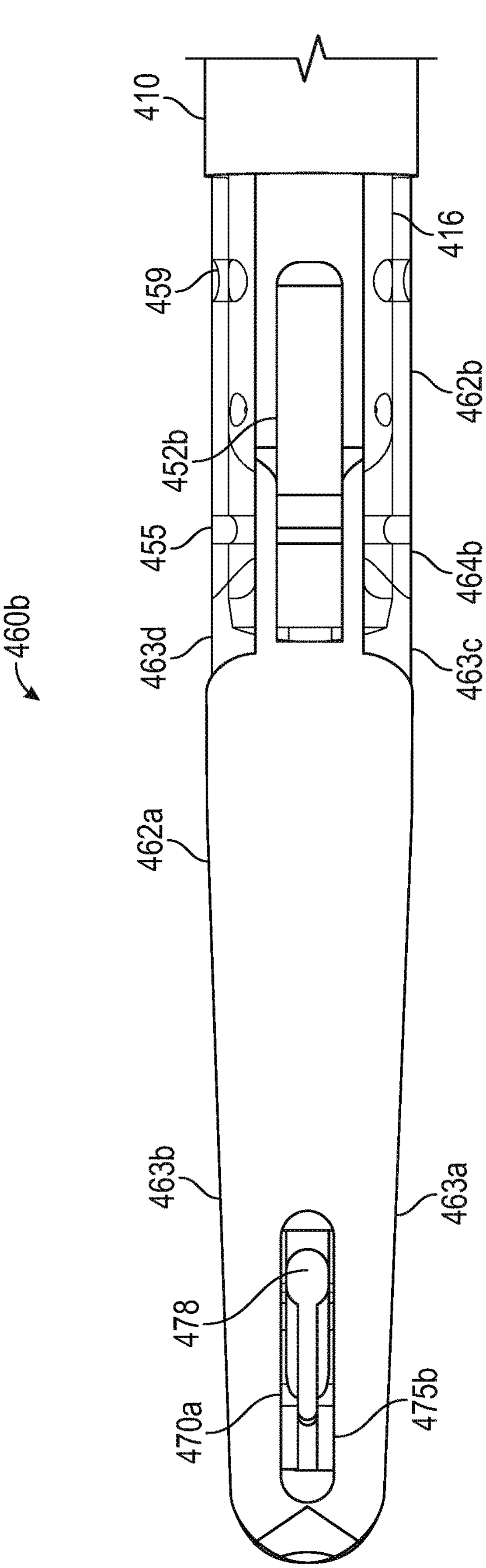
FIG. 26R is a top plan view of the multi-function jaw mechanism shown in FIG. 26A, in accordance with the invention.

In the noted embodiment, the fixed pivot mechanism 458 comprises (i) a first pin 453, which is sized and configured to be positioned in a first pin lumen in the top jaw member 462*a* and a second pin lumen in link 452*b*, (ii) a second pin 455, which is sized and configured to be positioned in a third pin lumen in the top jaw member 462*a* and a fourth pin lumen in the bottom jaw member 462*b*, and (iii) a third pin 459, which is sized and configured to be positioned in a fifth pin lumen in the bottom jaw member 462*b*, a sixth pin lumen in link 452*b*, and a seventh pin lumen in the distal end of the driver support rod 416 (shown in FIGS. 26Q and 26R).

As illustrated in FIGS. 26A and 26B, the bottom jaw member 462*b* comprises a proximal end 473*a*, a distal end

473*b*, and a suture engagement region 489*a* and a suture-tissue engagement region 491*b* disposed on the distal end 473*b* of the bottom jaw member 462*b*.

As illustrated in FIGS. 26A and 26M, the suture engagement region 489*a* comprises a raised proximal suture guide region 482, a raised distal guide region (denoted "475*a*", "475*b*" and "475*c*") and a suture loading or receiving slot 472 disposed therebetween.

As illustrated in FIGS. 26C-26E, the raised distal guide regions 475*a*, 475*b*, 475*c* comprise a distal tissue guide region 477 and a proximal suture guide region (denoted "480*a*", "480*b*" and "480*c*").

As further illustrated in FIGS. 26C-26E and discussed in detail below, each proximal suture guide region 480*a*, 480*b*, 480*c* comprises a different configuration to cooperate with the top jaw member 462*a*, as discussed below.

In a preferred embodiment, the outer edges of the raised distal guide regions 475*a*, 475*b*, 475*c* and, hence, proximal suture guide regions 480*a*, 480*b*, 480*c* thereof, and outer edges of raised proximal suture guide region 482 comprise rounded configurations to eliminate snagging of sutures thereon.

According to the invention, the outer surfaces of the raised distal guide regions 475*a*, 475*b*, 475*c* and, hence, proximal suture guide regions 480*a*, 480*b*, 480*c* thereof, and outer edges of raised proximal suture guide region 482 can further comprise curved or convex (or curvilinear) configurations to further abate snagging of sutures thereon.

Figure 26S:
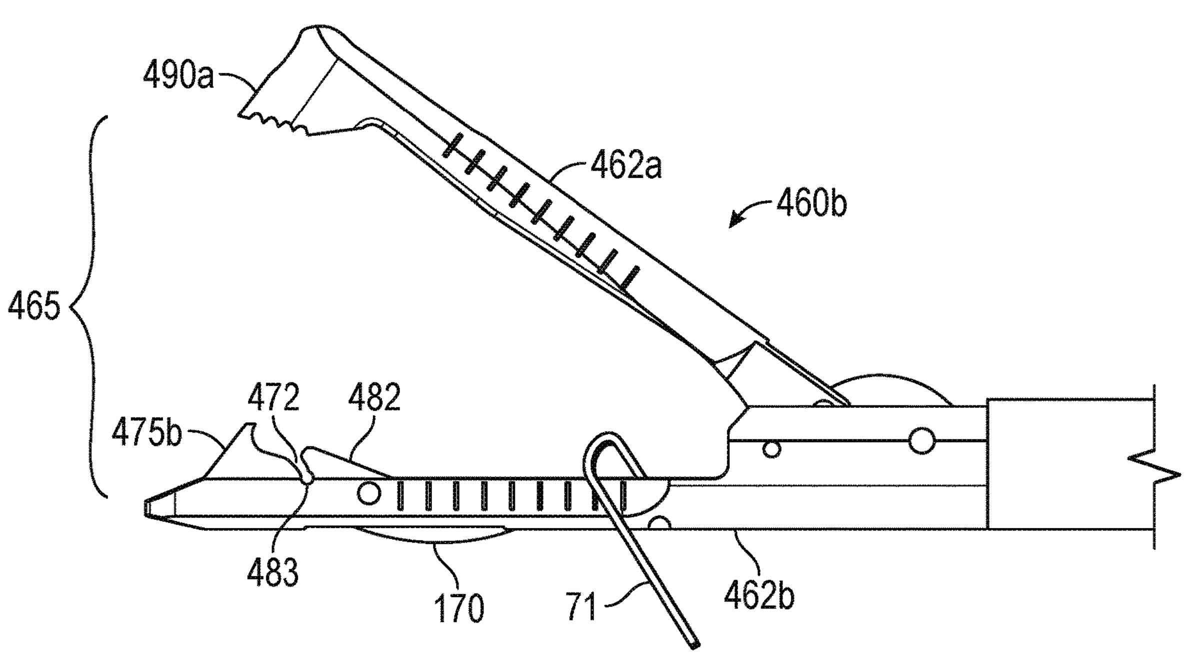
FIG. 26S is a side plan view of the multi-function jaw mechanism shown in FIG. 26A, showing the jaw mechanism in an open configuration with a suture disposed in the open internal region of the jaw mechanism, in accordance with the invention.
Figure 26T:
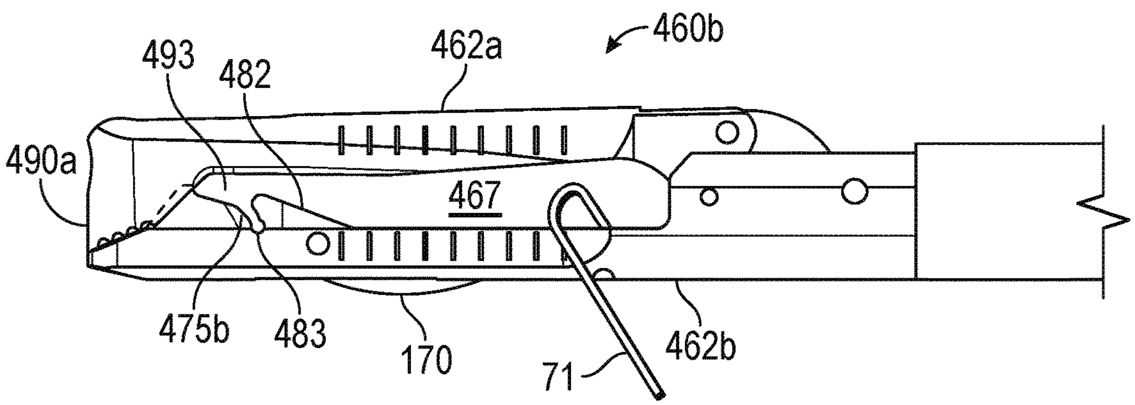
FIG. 26T is a side plan view of the multi-function jaw mechanism shown in FIG. 26A, showing the jaw mechanism in a closed configuration with the suture disposed in the open internal region of the jaw mechanism, in accordance with the invention.
Figure 26U:
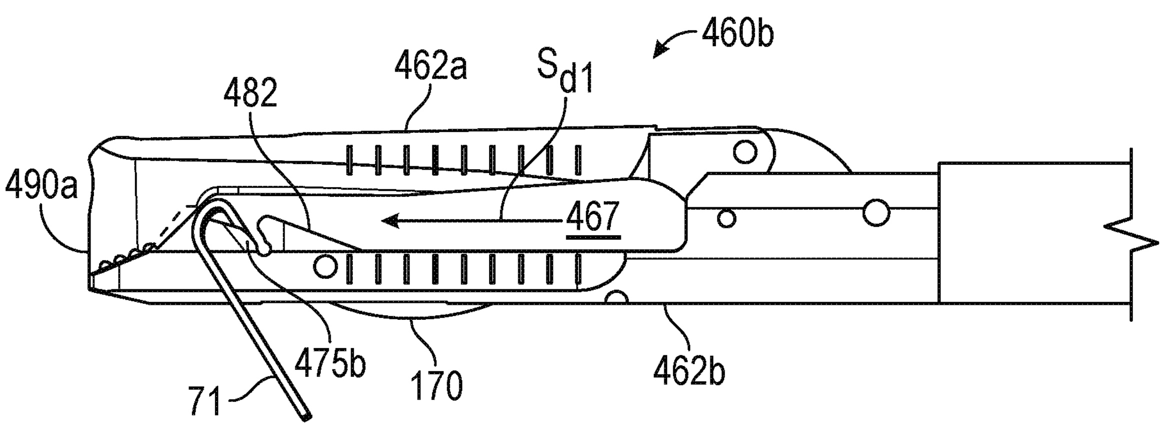
FIG. 26U is a side plan view of the multi-function jaw mechanism shown in FIG. 26A, showing the jaw mechanism in a closed configuration with the suture disposed in the suture containment region of the jaw mechanism, in accordance with the invention.
Figure 26V:
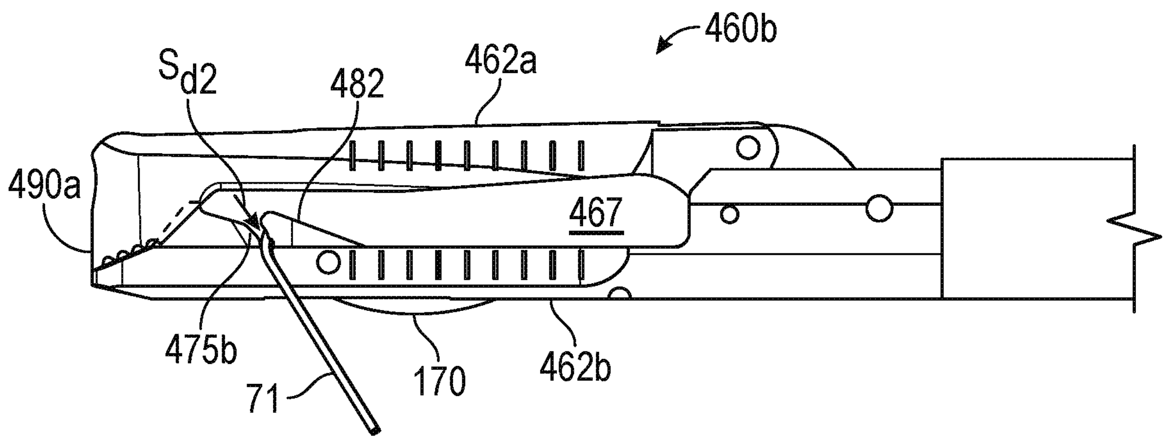
FIG. 26V is a side plan view of the multi-function jaw mechanism shown in FIG. 26A, showing the jaw mechanism in a closed configuration with the suture disposed in the suture loading slot of the lower jaw member of the jaw mechanism, in accordance with the invention.
Figure 26W:
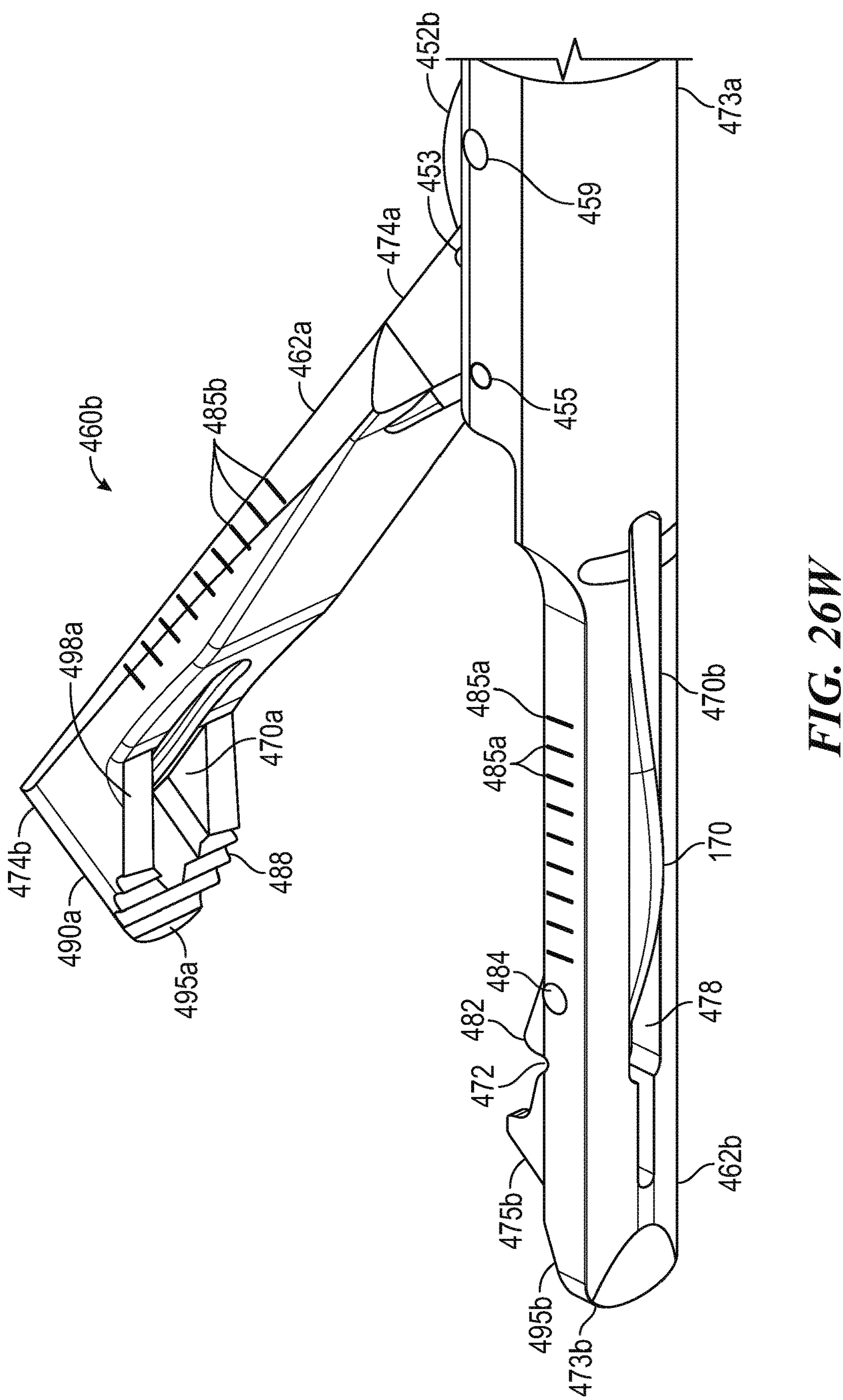
FIG. 26W is a side perspective view of the multi-function jaw mechanism shown in FIG. 26A, showing the open needle guide channel of the lower jaw member, in accordance with the invention.

As illustrated in FIG. 26V and discussed in detail below, the suture receiving slot 472 is sized and configured to slidably receive a suture therein, whereby, a suture, such as suture 71, can be readily loaded therein transversely or, as discussed below, as a loop, as illustrated in FIG. 26S.

As further illustrated in FIGS. 26S and 26T, the suture receiving slot 472 comprises a suture seat 483 that is sized and configured to receive, position and releasably secure a suture, such as suture 71, in the suture receiving slot 472. As discussed below, suture seat 483 defines a needle engagement and tissue stitch point.

As illustrated in FIG. 26Q, the bottom jaw member 462*b* further comprises a continuous needle guide channel 478 that runs from the elongated shaft 410 of the suture passer device 400, into and through the bottom jaw member window 470*b*, and transects the suture loading slot 472.

In a preferred embodiment, the needle guide channel 478 is sized and configured to receive a needle of the invention; preferably, needle 170, therein and allow translation of the needle 170 therethrough and articulation of the needle therein.

In a preferred embodiment, the needle guide channel 478 is positioned in the bottom jaw member 462*b*, whereby, a suture disposed in the suture loading slot 472 can be engaged by the needle 170 when the needle 170 slidably translates through and articulates in the needle guide channel 478.

Figure 26X:
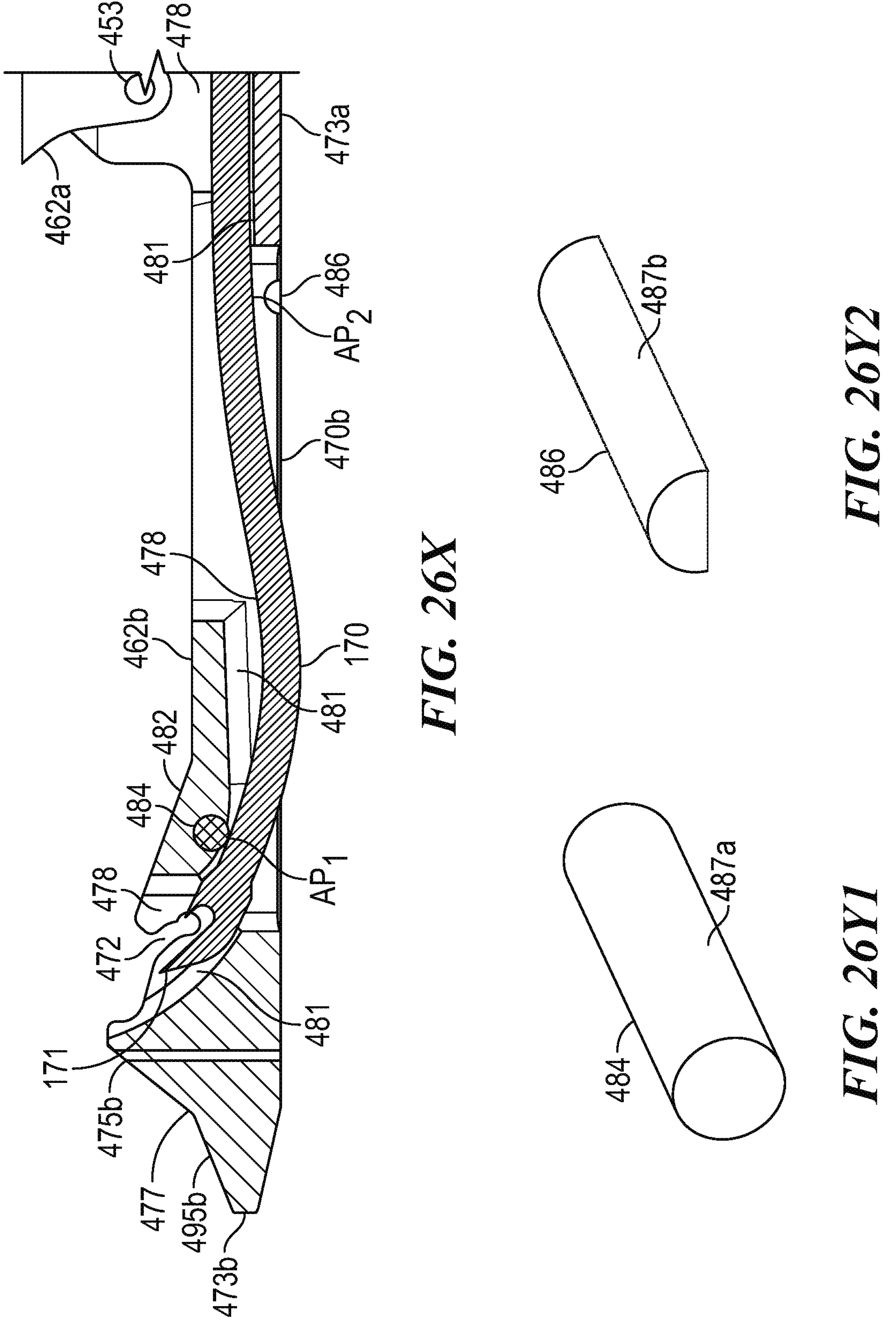
FIG. 26X is a side partial perspective view of the bottom jaw member of the multi-function jaw mechanism shown in FIG. 26A, showing the needle disposed in the open needle guide channel, in accordance with the invention.

As illustrated in FIG. 26X, in a preferred embodiment, the needle guide channel 478 comprises an open structure.

As illustrated in FIGS. 26A and 26B, the top jaw member 462*a* comprises a proximal end 474*a* and a distal end 474*b*.

As further illustrated in FIGS. 26A, 26B, 26I and 26L, in some embodiments, the top jaw member 462*a* comprises a projecting guide region (denoted "490*a*") with a first embodiment of a suture backstop region (denoted "BR" and discussed below), which is disposed on the distal end 474*b* of the top jaw member 462*a*.

Referring now to FIG. 26J in some embodiments, the top jaw member 462*a* comprises a raised or projecting guide region (denoted "490*b*") with a second embodiment of a suture backstop region (BR), which is disposed on the distal end 474*b* of the top jaw member 462*a*.

As illustrated in FIGS. 26A, 26I, 26J and 26L, the projecting guide regions 490*a*, 490*b* comprise a proximal end 497*a*, a distal end 497*b*, and a top jaw member suture-tissue engagement region (in this instance, denoted "491*a*") disposed on the distal end 497*b* of the projecting guide regions 490*a*, 490*b* and, hence, distal end 474*b* of the top jaw member 462*a*.

As further illustrated in FIGS. 26A and 26L, in a preferred embodiment, the projecting guide regions 490*a*, 490*b* of the top jaw member 462*a* further comprise a suture guide region (denoted "498*a*" in FIGS. 26A and 26L, and "498*b*" in FIG. 26J) disposed on the proximal end 497*a* of the projecting guide regions 490*a*, 490*b*.

According to the invention, the suture guide regions 498*a*, 498*b* of the projecting guide regions 490*a*, 490*b* can comprise various shapes.

As illustrated in FIGS. 26A and 26L, in some embodiments, suture guide region 498*a* comprises a substantially planar shape, and, as discussed below, in some embodiments, forms a suture backstop region (denoted "$BR_1$").

In a preferred embodiment, the suture guide region of the projecting guide regions 490*a*, 490*b* comprise a curvilinear shape, such as suture guide region 498*b* illustrated in FIG. 26J, and as discussed below, in some embodiments, similarly forms a suture backstop region (denoted "$BR_2$").

As further illustrated in FIGS. 26Q and 26R, the top jaw member 462*a* further comprises a top jaw member window 470*a* that is sized and configured to allow needle 170 (not shown) to traverse therethrough.

As illustrated in FIGS. 26F-26H, top jaw member window 470*a* is further sized and configured to receive and seat the suture engagement region 489*a* of the bottom jaw member 462*b*, whereby, as illustrated in FIGS. 26F-26K, a suture containment region 493 is provided when the multi-function jaw mechanisms of the invention, i.e., multi-function jaw mechanisms 460*b*, 460*c*, 460*d*, 460*e*, 460*f*, are in a closed configuration.

Referring back to FIGS. 26F-26H, in a preferred embodiment, when the multi-function jaw mechanism 460*b* (and multi-function jaw mechanisms 460*c*, 460*d*, 460*e*, 460*f*) is in a closed configuration and the suture engagement region 489*a* of the bottom jaw member 462*b* is seated in the top jaw member window 470*a*, a gap 499 is provided between the top jaw member 462*a* and the proximal suture guide region 482 of the suture engagement region 489*a* and, hence, bottom jaw member 462*b*, which allows a suture, such as suture 71, to be translated in a distal direction into the suture containment region 493.

In a preferred embodiment, the gap 499 comprises a distance of at least approximately 0.25 mm.

In a preferred embodiment, when the multi-function jaw mechanism 460*b* (and multi-function jaw mechanisms 460*c*, 460*d*, 460*e*, 460*f*) is in a closed configuration and the suture engagement region 489*a* of the bottom jaw member 462*b* is seated in the top jaw member window 470*a*, a suture backstop region (BR) is formed in the suture containment region 493, which abates translation of a suture, such as suture 71, in a distal direction.

In some embodiments, the projecting guide region 490*a* of the top jaw member 462*a* forms the suture backstop region ($BR_1$), such as illustrated in FIG. 26H.

In some embodiments, the projecting guide region 490*b* of the top jaw member 462*a* forms the suture backstop region ($BR_2$), such as illustrated in FIG. 26J.

In some embodiments, the suture engagement region 489*a* of the bottom jaw member 462*b* forms the suture backstop region ($BR_3$), such as illustrated in FIGS. 26F and 26K.

In some embodiments, the projecting guide region 490*a* of the top jaw member 462*a* and the suture engagement region 489*a* of the bottom jaw member 462*b* form the suture backstop region ($BR_4$), such as illustrated in FIGS. 26G and 26I.

In some embodiments, the projecting guide region 490*b* of the top jaw member 462*a* and the suture engagement region 489*a* of the bottom jaw member 462*b* form a suture backstop region.

In a preferred embodiment, the outer edges of the proximal end regions of the projecting guide regions 490*a*, 490*b* of the top jaw member 462*a* similarly comprise rounded configurations to eliminate snagging of sutures thereon.

According to the invention, the outer surfaces of the proximal end regions of the projecting guide regions 490*a*, 490*b* of the top jaw member 462*a* can similarly further comprise curved or convex (or curvilinear) configurations to further abate snagging of sutures thereon.

As discussed in detail below, the backstop regions ($BR_1$, $BR_2$, $BR_3$, $BR_4$) and suture engagement region 489*a* of the bottom jaw member 462*b* jointly facilitate several seminal functions and, hence, features of the multi-function jaw mechanism 460*b* (and multi-function jaw mechanisms 460*c*, 460*d*, 460*e*, 460*f*); particularly, uncomplicated and highly reliable suture loading and retrieval with minimal visual guidance.

Referring now to FIGS. 26S-26V, operation of the multi-function jaw mechanism 460*b* (and multi-function jaw mechanisms 460*c*, 460*d*, 460*e*, 460*f*) (referred to hereinafter collectively as "multi-function jaw mechanisms") will be described in detail below.

Referring first to FIG. 26S, in accordance with one preferred procedure for loading suture into the multi-function jaw mechanisms of the invention, a loop of suture, in this instance, suture 71, is initially guided into the open jaw mechanism region 465 defined by the top and bottom jaw members 462*a*, 462*b* of the jaw mechanism 460*b*.

After the loop of suture 71 is guided into the open jaw mechanism region 465, the multi-function jaw mechanisms are induced to transition from the default fully open configuration illustrated in FIG. 26S, to the closed configuration, as illustrated in FIG. 26T, via a jaw articulation control system of the invention, whereby the loop of suture 71 is entrapped in the closed jaw mechanism region 467.

After the multi-function jaw mechanisms are positioned in the closed configuration with the suture 71 entrapped in the closed jaw mechanism region 467, the loop of suture 71 is manually drawn in a distal direction toward the suture containment region 493, as denoted by arrow "$S_{d1}$" in FIG. 26U, until, as discussed below, the suture 71 abuts against a backstop region, i.e., $BR_1$, $BR_2$, $BR_3$ or $BR_4$, of the multi-function jaw mechanisms, wherein further distal translation of the suture 71 is abated.

After distal translation of the suture 71 is abated by a backstop region of the multi-function jaw mechanisms, the suture 71 is manually drawn in a proximal inferior direction, as denoted by arrow "$S_{d2}$" in FIG. 26V, wherein the backstop region, i.e., $BR_1$, $BR_2$, $BR_3$ or $BR_4$, and the suture engagement region 489*a* guide the suture 71 into the suture receiving slot 472 and suture seat 483 thereof, whereby, as discussed below, the suture 71 is in a position to be captured by the system needle 170 and passed into and through target soft tissue.

According to the invention, the suture 71 can be captured by the system needle 170 and directed into and through a target suture site in the soft tissue by transitioning the multi-function jaw mechanisms back to the fully open jaw configuration, positioning the jaw mechanisms at the target soft tissue site, positioning the soft tissue in the open jaw mechanism region 465 of the multi-function jaw mechanisms, capturing the soft tissue with the multi-function jaw mechanisms by transitioning the multi-function jaw mechanisms back to the closed jaw configuration, and inducing translation of the system needle 170 through and out of the multi-function jaw mechanisms and into the soft tissue.

After the suture 71 is passed into and through the soft tissue, the system needle 170 is retracted and the multi-function jaw mechanisms are transitioned back to the default fully open configuration, wherein the soft tissue is released with a portion of the suture 71 engaged thereto and a portion of the suture 71, i.e., free end, engaged to the multi-function jaw mechanisms via suture retaining ribbon (which is shown in phantom in FIG. 26Q, and denoted "450"), which is induced to slidably translate through ribbon slot 454 of the top jaw member 462*a* toward the distal end 474*b* and into the suture ensnarement region 479 thereof (which is disposed in the distal wall 496 of the window 470*a*) by a suture control system of the invention. The suture passing system is thereafter withdrawn from the soft tissue site with the free end of the suture 71 engaged to the multi-function jaw mechanisms.

Figure 27A:
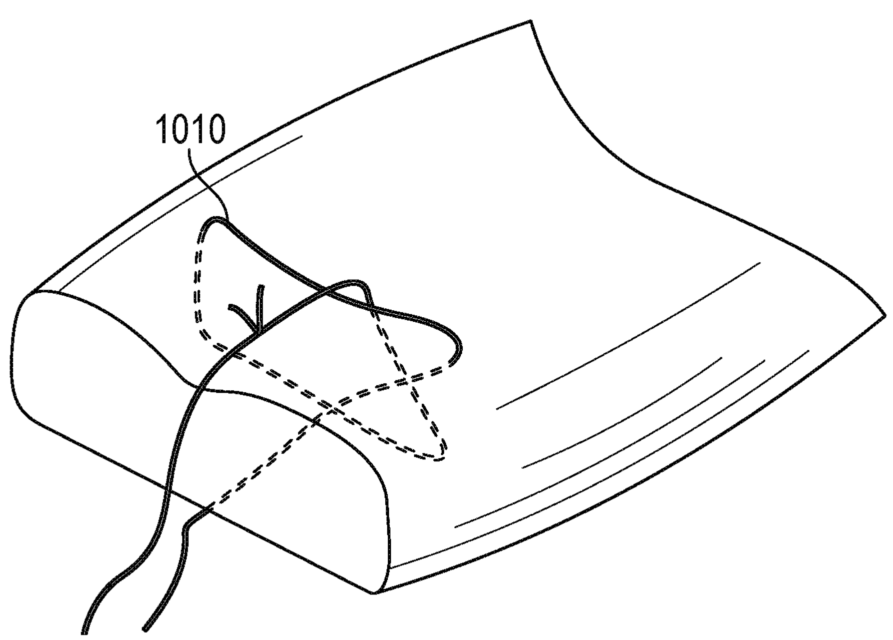
FIG. 27A is an illustration of a Mason-Allen stitch pattern.

After the suture passing device is withdrawn from the soft tissue site, the free end of the suture 71 is released from the multi-function jaw mechanisms. The suture 71 can then be reloaded into the multi-function jaw mechanisms and directed into and through a second target suture site in the soft tissue in the same manner as discussed above to facilitate the provision of various stitch patterns at the surgical site; particularly, Mason-Allen and modified Mason-Allen stitch patterns, including the Mason-Allen and modified Mason-Allen stitch patterns illustrated in FIGS. 27A and 27B, and denoted "1010" and "1020", respectively.

By virtue of the optimal suture manipulation provided by the multi-function jaw mechanisms of the invention, i.e., multi-function jaw mechanisms 460*b*, 460*c*, 460*d*, 460*e*, 460*f*, various additional stitch patterns can be precisely formed in soft tissue, including, without limitation, mattress, sliding mattress, far-near-near-far, Bunnell-Mayer, three-loop pulley, locking loop, modified Kessler, simple interrupted, simple continuous, Ford interlocking, interrupted cruciate, interrupted horizontal mattress, continuous horizontal mattress, interrupted vertical mattress, quilled, interrupted or continuous Lembert, interrupted quilt, Cushing, Connel, Parker-Kerr, purse string stitch patterns and modified variants thereof.

As indicated above, an additional surgical function and, hence, feature of the multi-function jaw mechanisms of the invention comprises means for separately and effectively grasping, capturing and engaging soft tissue (prior to and after passage of suture therethrough) and surgical instruments and devices, such as tissue graspers and suture retrievers, and tissue anchors, patches and prosthetic devices, at and within a confined surgical site with minimal visual guidance.

In a preferred embodiment of the invention, the multi-function jaw mechanisms are also adapted to engage, grasp and capture suture within a confined surgical site with minimal visual guidance.

According to the invention, the suture can comprise the same or first suture passed through soft tissue and retained by the multi-function jaw mechanisms and other suture while the first suture is retained by the multi-function jaw mechanisms, i.e., static and dynamic suture capture.

In a preferred embodiment, to facilitate the soft tissue, suture, and surgical instrument and device engagement and capture function(s), the top and bottom jaw members 462*a*, 462*b* of the multi-function jaw mechanisms comprise suture-tissue engagement regions.

As illustrated in FIGS. 26A and 26L, in some embodiments, the projecting top jaw member region 490*a* of the top jaw member 462*a* comprises one embodiment of a suture-tissue engagement region (denoted "491*a*").

As illustrated in FIG. 26J, in some embodiments, the projecting top jaw member region 490*b* of the top jaw member 462*a* comprises suture-tissue engagement region 491*a*.

As illustrated in FIGS. 26A and 26L, in some embodiments, the suture-tissue engagement region 491*a* of the top jaw member 462*a* defines a single plane.

As illustrated in FIG. 26L, in a preferred embodiment, the top jaw member suture-tissue engagement region 491*a* comprises a top jaw member suture-tissue engaging surface 495*a* and, as illustrated in FIG. 26M, the bottom jaw member suture-tissue engagement region 491*b* comprises a bottom jaw member suture-tissue engaging surface 495*b*, which, as discussed in detail below, is positioned, configured and adapted to cooperate with the top jaw member suture-tissue engaging surface 495*a* and, hence, top jaw member suture-tissue engagement region 491*a* when the multi-function jaw mechanisms of the invention are in a closed jaw configuration and transition thereto.

As illustrated in FIG. 26B, in a preferred embodiment, the top and bottom jaw member suture-tissue engagement regions 491*a*, 491*b*, and, thus, top and bottom jaw member suture-tissue engaging surfaces 495*a*, 495*b* are positioned on the top and bottom jaw members 462*a*, 462*b*, wherein the top and bottom jaw member suture-tissue engagement regions 491*a*, 491*b*, and, thus, top and bottom jaw member suture-tissue engaging surfaces 495*a*, 495*b* are aligned and the suture-tissue engagement regions 491*a*, 491*b* of the top and bottom jaw members 462*a*, 462*b* form a jaw mechanism suture-tissue engagement region (denoted "471" in FIG. 26N) when the multi-function jaw mechanism 460*b* (and, as discussed below, multi-function jaw mechanisms 460*c*, 460*d*, 460*e*, 460*f*) is in a closed configuration (also shown in phantom in FIG. 26K), and, as illustrated in FIG. 26O, during transition of the multi-function jaw mechanism 460*b* (and multi-function jaw mechanisms 460*c*, 460*d*, 460*e*, 460*f*) to the closed jaw configuration, i.e., to a partially open jaw configuration, the suture-tissue engagement regions 491*a*, 491*b* of the top and bottom jaw members 462*a*, 462*b* provide a jaw mechanism suture-tissue capture region (denoted "465" in FIG. 26O), which is configured to receive and, hence, facilitate grasping, capture and engagement of sutures, soft tissue and surgical instruments and devices therein.

In a preferred embodiment, when the multi-function jaw mechanism 460*b* (and multi-function jaw mechanisms 460*c*, 460*d*, 460*e*, 460*f* discussed below) is in a closed configuration, the jaw mechanism suture-tissue engagement region 471 extends less than 20% of the length of the top jaw member 462*a* (denoted "$L_{TM}$" in FIG. 26B) from the distal end 474*b* thereof or the length of the bottom jaw member 462*b* (denoted "$L_{BM}$") from the distal end 473*b* thereof.

In a preferred embodiment, the top jaw member suture-tissue engagement region 491*a* extends proximally from the distal end 474*b* of the top jaw member 462*a* no greater than 12.0 mm, more preferably, no greater than 8.0 mm, even more preferably, no greater than 6.0 mm.

In a preferred embodiment, the bottom jaw member suture-tissue engagement region 491*b* similarly extends proximally from the distal end 473*b* of the bottom jaw member 462*b* no greater than 12.0 mm, more preferably, no greater than 8.0 mm, even more preferably, no greater than 6.0 mm.

According to the invention, the surface of the suture-tissue engaging surface 495*a* of the top jaw member 462*a* can comprise various surface features to facilitate capture and engagement of soft tissue, sutures and surgical instruments and devices between the suture-tissue engaging surfaces 495*a*, 495*b*.

As illustrated in FIGS. 26A and 26L, in one embodiment, the top jaw member suture-tissue engaging surface 495*a* comprises a serrated surface 488.

According to the invention, the surface of the bottom jaw member suture-tissue engaging surface 495*b* can similarly comprise various surface features to similarly facilitate engagement of capture and engagement of soft tissue, sutures and surgical instruments and devices between the suture-tissue engaging surfaces 495*a*, 495*b*, such as a plurality of reciprocating serrations that are sized and configured to interlock with the serrated surface 488 of the suture-tissue engagement surface 495*a* of the top jaw member 462*a*, or simply comprise a substantially flat or planar smooth surface, as illustrated in FIG. 26M.

In a preferred embodiment, the distal ends 474*b*, 473*b* of the top and bottom jaw members 462*a*, 462*b* and, hence, the top and bottom suture-tissue engaging surfaces 495*a*, 495*b* are configured and adapted to engage, grasp and capture fine sutures and a "finite" portion thereof, and defined, finite portions of soft tissue proximate the distal ends 474*b*, 473*b* of the top and bottom jaw members 462*a*, 462*b* and hence, top and bottom suture-tissue engaging surfaces 495*a*, 495*b* within a confined surgical site when the multi-function jaw mechanism 460*b* transitions to and is in a closed jaw configuration.

As illustrated in FIG. 26B, in a preferred embodiment, when the multi-function jaw mechanism 460*b* is in a closed configuration, the top and bottom jaw member suture-tissue engagement regions 491*a*, 491*b* are in contact.

Thus, when the multi-function jaw mechanism 460*b* transitions to and is in a closed configuration, the top and bottom suture-tissue engaging surfaces 495*a*, 495*b* of the top and bottom jaw members 462*a*, 462*b* will engage, grasp and capture fine sutures and soft tissue within a confined surgical site.

Referring now to FIGS. 28A-28I, there is shown another embodiment of a multi-function jaw mechanism of the invention (denoted "460*c*").

Figure 28A:
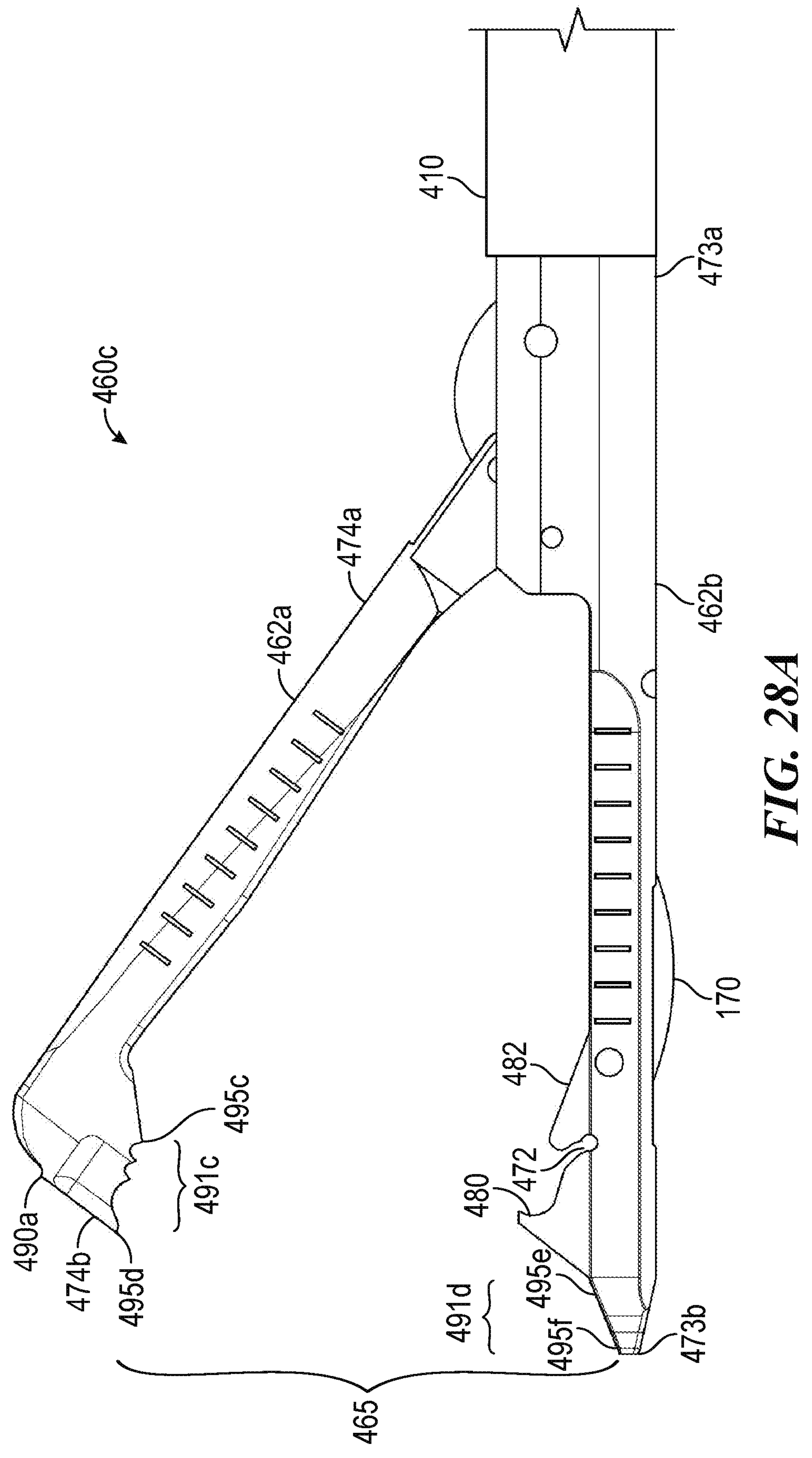
FIG. 28A is a side plan view of another embodiment of a multi-function jaw mechanism in a fully open jaw configuration, in accordance with the invention.

As illustrated in FIG. 28A, in a preferred embodiment, to facilitate the soft tissue, suture and surgical instrument and device engagement and capture function(s), the top and bottom jaw members 462*a*, 462*b* of the multi-function jaw mechanism 460*c* similarly comprise suture-tissue engagement regions positioned, configured and adapted to engage, grasp and capture (or retain) soft tissue, sutures and surgical instruments and devices.

Figure 28B:
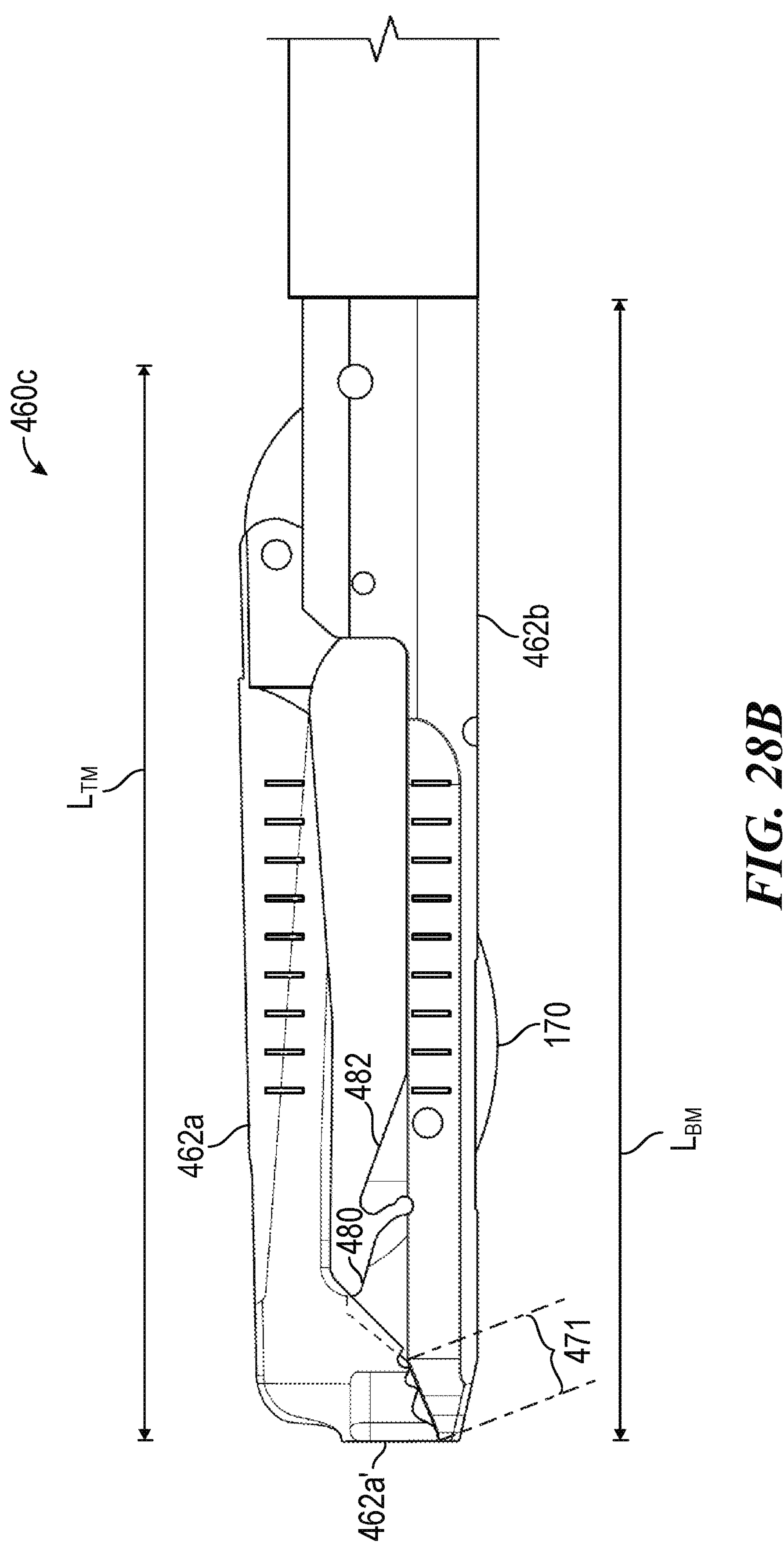
FIG. 28B is a further side plan view of the multi-function jaw mechanism shown in FIG. 28A in a fully closed jaw configuration, in accordance with the invention.
Figure 28C:
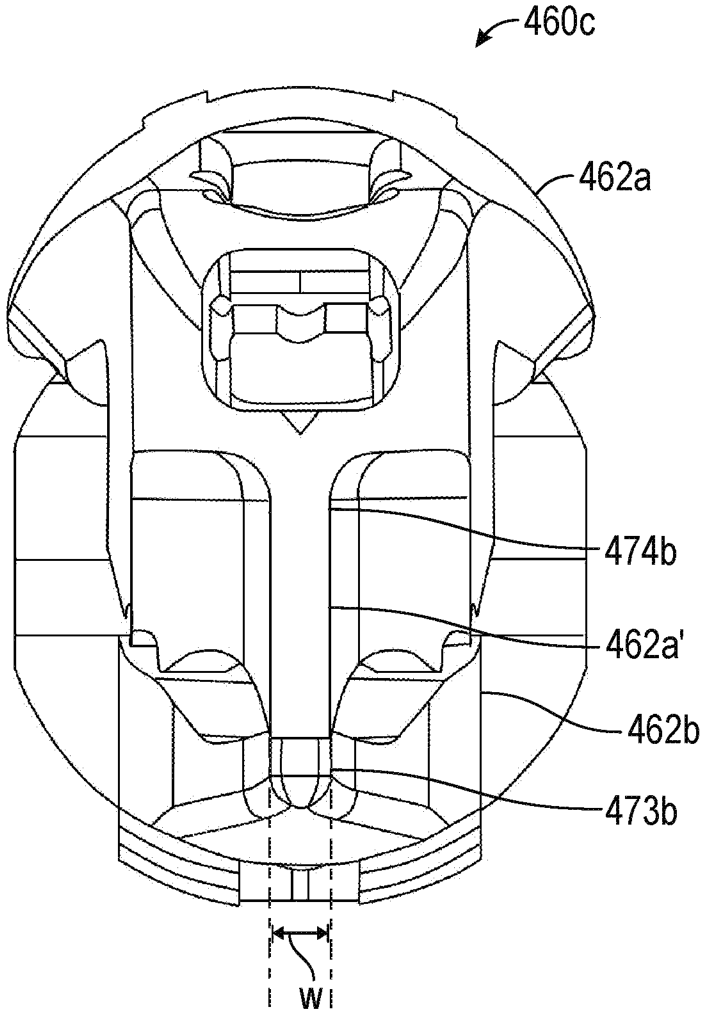
FIG. 28C is an end plan view of the multi-function jaw mechanism shown in FIG. 28A in a fully closed jaw configuration, in accordance with the invention.
Figure 28D:
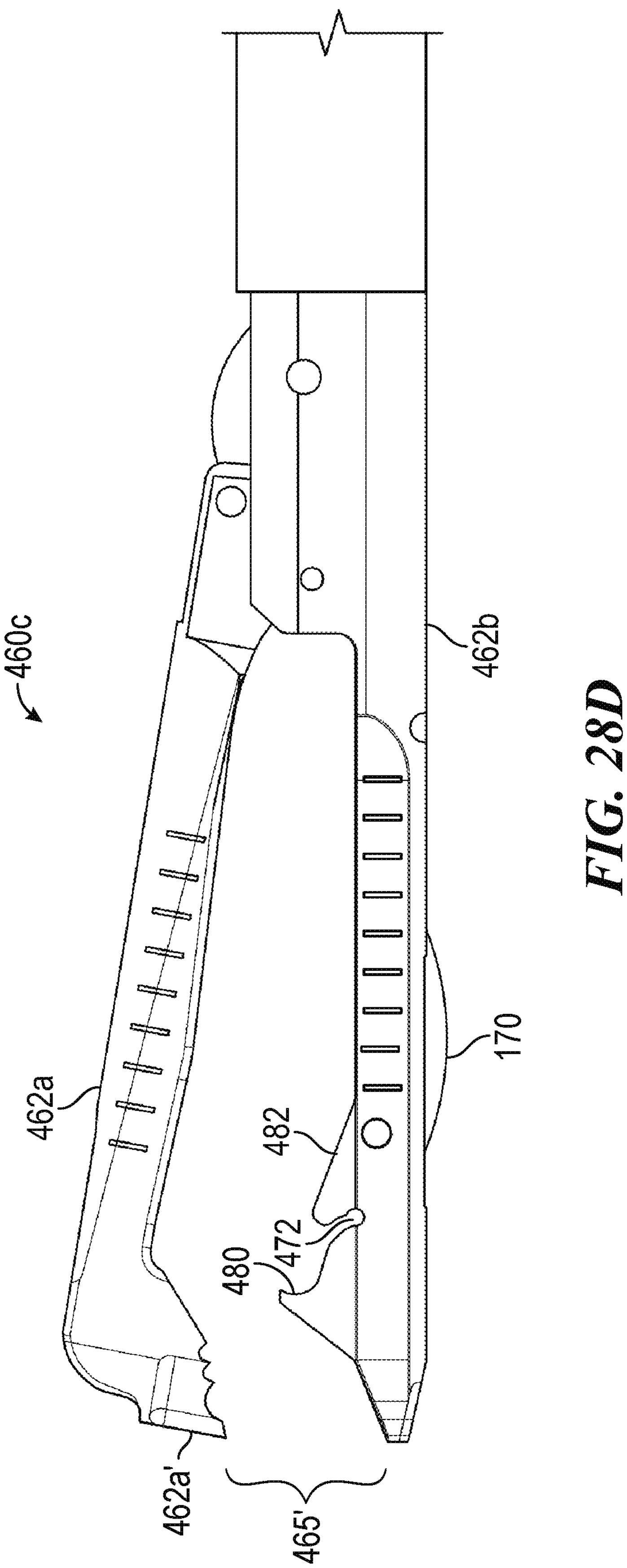
FIG. 28D is a further side plan view of the multi-function jaw mechanism shown in FIG. 28A, showing the jaw mechanism in a partially open jaw configuration, in accordance with the invention.
Figure 28E:
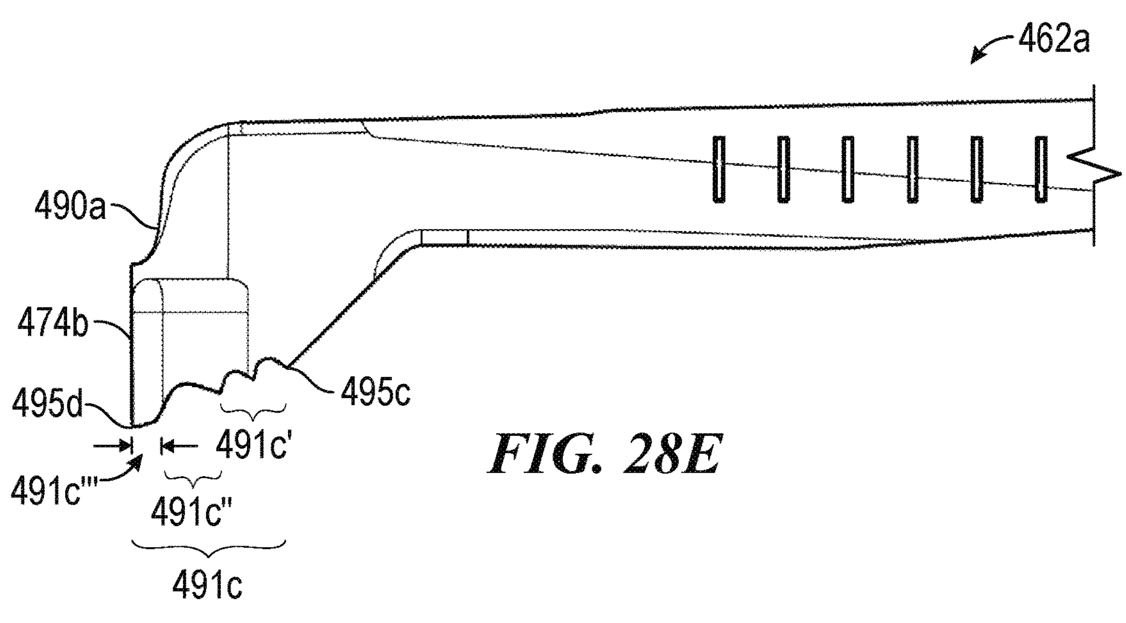
FIG. 28E is a partial side plan view of the top jaw member of the multi-function jaw mechanism shown in FIG. 28A, in accordance with the invention.

As illustrated in FIG. 28E, in a preferred embodiment, the distal end 474*b* of the top jaw member 462*a* comprises another embodiment of a suture-tissue engagement region (denoted "491*c*").

In a preferred embodiment, the top jaw member suture-tissue engagement region 491*c* comprises a dual zone suture-tissue engagement region comprising a top jaw member tissue engagement region (denoted 491*c*'), a top jaw member suture engagement region (denoted 491*c*") and a top jaw member recess (denoted 491*c*") disposed between the top jaw member tissue engagement region 491*c*' and the top jaw member suture engagement region 491*c*'''.

Figure 28F:
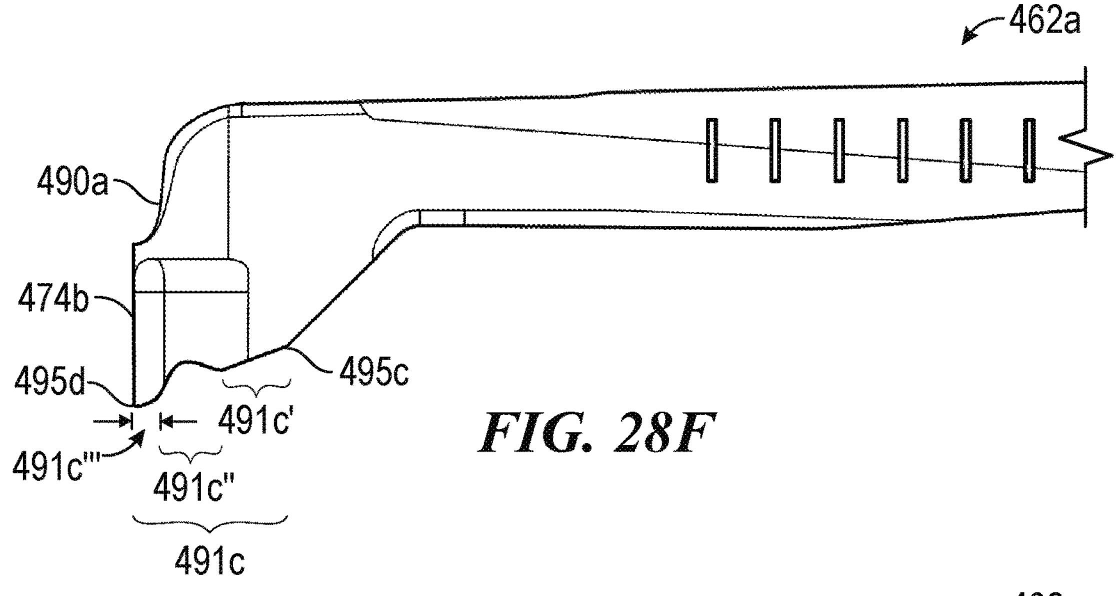
FIG. 28F is a partial side plan view of another embodiment of a top jaw member of the multi-function jaw mechanism shown in FIG. 28A, in accordance with the invention.
Figure 28G:
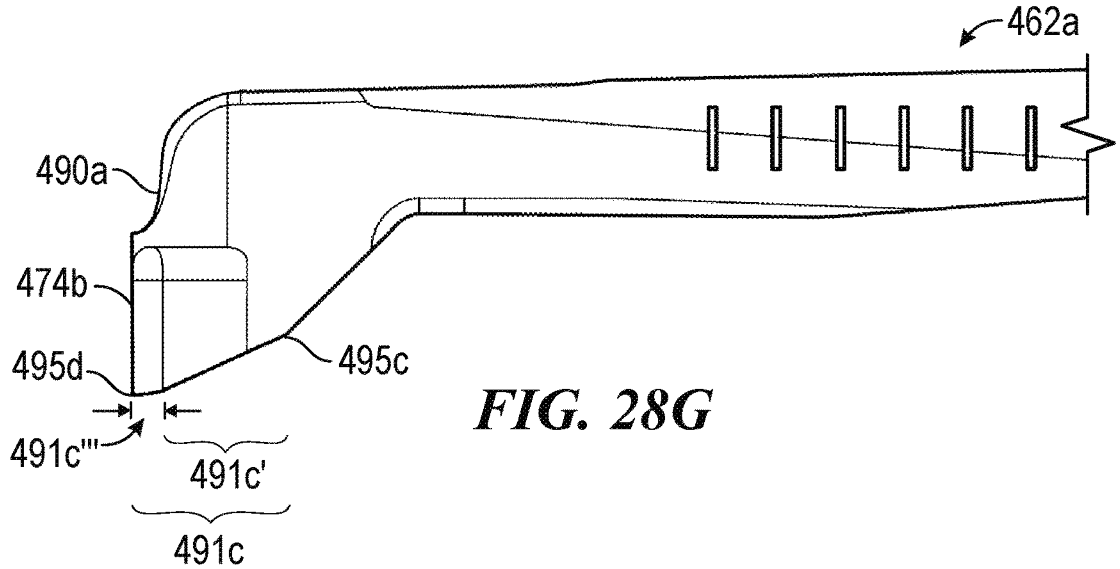
FIG. 28G is a partial side plan view of yet another embodiment of a top jaw member of the multi-function jaw mechanism shown in FIG. 28A, in accordance with the invention.

According to the invention, the top jaw member suture-tissue engagement region 491*c* can also merely comprise the top jaw member tissue engagement region 491*c*' and the top jaw member suture engagement region 491*c*''' without the top jaw member recess 491*c*", as illustrated in FIG. 28G.

In a preferred embodiment, the depth of the top jaw member recess 491*c*" is in the range of at least approximately 0.10 mm to approximately 1.5 mm, more preferably, the depth of the top jaw member recess 491*c*" is in the range of at least approximately 0.50 mm to approximately 0.75 mm.

As illustrated in FIGS. 28A and 28E, in a preferred embodiment, the top jaw member tissue engagement region 491*c*' comprises a top jaw member tissue engaging surface 495*c* that is configured and adapted to grasp at least soft tissue and, hence, sutures and surgical instruments and devices.

As further illustrated in FIGS. 28A and 28E, in a preferred embodiment, the top jaw member suture engagement region 491*c*" comprises a top jaw member suture engaging surface 495*d* that is configured and adapted to at least removably engage suture and, thus, also grasp and engage soft tissue and surgical instruments and devices.

As illustrated in FIG. 28C, in a preferred embodiment, the top jaw member suture engagement region 491*c*' comprises a substantially planar structure (denoted "462*a*") that extends distally from the top jaw member tissue engagement region 491*c*'.

According to the invention, the planar structure 462*a*' defines a longitudinal plane that is substantially parallel to the longitudinal axis of the top jaw member 462*a*.

In a preferred embodiment, the top jaw member suture engagement region 491*c*" extends proximally from the distal end 474*b* of the top jaw member 462*a* no greater than 4.0 mm, more preferably, the top jaw member suture engagement region 491*c*" extends from the distal end 474*b* of the top jaw member 462*a* no greater than 2.0 mm from the distal end 474*b* of the top jaw member 462*a*.

In a preferred embodiment, the top jaw member suture engagement region 491*c*" has a width in a lateral direction, i.e., perpendicular to the longitudinal axis of the top jaw member 462*a*, as denoted by "w" in FIG. 28C, no greater than approximately 4.0 mm, more preferably, the top jaw member suture engagement region 491*c*" has a width in a lateral direction no greater than approximately 2.0 mm.

As discussed in detail below, the planar structure 462*a*' of the top jaw member suture engagement region 491*c*" and length thereof facilitates grasping and engagement of defined, finite portions of fine sutures, e.g., 0.01 mm (USP designation 11-0).

In some embodiments, the distal end of the planar structure 462*a*' and, hence, distal end 474*b* of the top jaw member 462*a* comprises a substantially pointed configuration to further facilitate grasping and engagement of defined, finite portions of fine sutures.

Figure 28H:
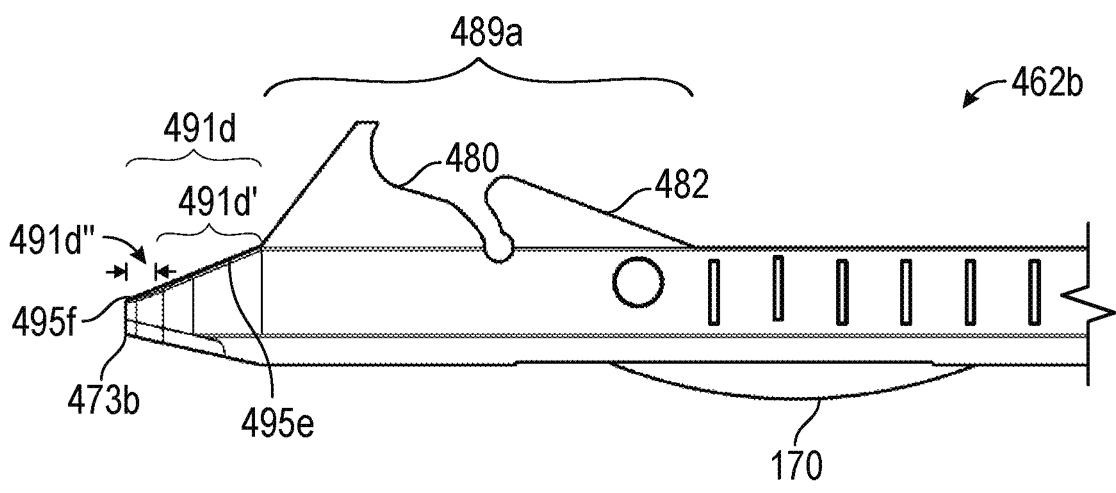
FIG. 28H is a partial side plan view of the bottom jaw member of the multi-function jaw mechanism shown in FIG. 28A, in accordance with the invention.

As illustrated in FIG. 28H, in a preferred embodiment, the distal end 473*b* of the bottom jaw member 462*b* similarly comprises one embodiment of a bottom jaw member suture-tissue engagement region (denoted "491*d*").

In a preferred embodiment, the bottom jaw member suture-tissue engagement region 491*d* similarly comprises a dual zone suture-tissue engagement region comprising a bottom jaw member tissue engagement region (denoted 491*d*') and a bottom jaw member suture engagement region (denoted 491*d*").

Referring back to FIGS. 28A and 28H, in a preferred embodiment, the bottom jaw member tissue engagement region 491*d*' comprises a bottom jaw member tissue engaging surface 495*e* that is configured and adapted to grasp at least soft tissue and, hence, sutures and surgical instruments and devices.

As further illustrated in FIGS. 28A and 28H, in a preferred embodiment, the bottom jaw member suture engagement region 491*d*" comprises a bottom jaw member suture engaging surface 495*f* that is configured and adapted to removably engage suture and, hence, soft tissue and surgical instruments and devices.

As illustrated in FIGS. 28B and 28G, in a preferred embodiment, the top and bottom jaw member suture-tissue engagement regions 491*c*, 491*d* are positioned on the top and bottom jaw members 462*a*, 462*b*, whereby the top and bottom jaw member suture-tissue engagement regions 491*c*, 491*d*, and, thus, top and bottom jaw member tissue engaging surfaces 495*c*, 495*e*, and top and bottom jaw member suture engaging surfaces 495*d*, 495*f* are aligned when the multi-function jaw mechanism 460*c* is in a closed configuration, wherein the top and bottom jaw member suture-tissue engagement regions 491*c*, 491*d* of the top and bottom jaw members 462*a*, 462*b* similarly form jaw mechanism suture-tissue engagement region 471 (see FIGS. 28B and 28I), and, as illustrated in FIG. 28D, during transition of the multi-function jaw mechanism 460*c* to the closed jaw configuration, i.e., the partially open jaw configuration, the top and bottom jaw member suture-tissue engagement regions 491*c*, 491*d* similarly provide jaw mechanism suture-tissue capture region 465', which is similarly configured to receive and, hence, facilitate grasping, capture and engagement of soft tissue, sutures and surgical instruments and devices therein.

In a preferred embodiment, when the multi-function jaw mechanism 460*c* is in a closed configuration, the jaw mechanism suture-tissue engagement region 471 similarly extends proximally less than 20% of the length $L_{TM}$ of the top jaw member 462*a* from the distal end 474*b* thereof or the length $L_{BM}$ of the bottom jaw member 462*b* from the distal end 473*b* thereof.

In a preferred embodiment, the top jaw member suture-tissue engagement region 491*c* similarly extends proximally from the distal end 474*b* of the top jaw member 462*a* no greater than 12.0 mm, more preferably, no greater than 8.0 mm, even more preferably, no greater than 6.0 mm.

In a preferred embodiment, the bottom jaw member suture-tissue engagement region 491*d* similarly extends proximally from the distal end 473*b* of the bottom jaw member 462*b* no greater than 12.0 mm, more preferably, no greater than 8.0 mm, even more preferably, no greater than 6.0 mm.

As further illustrated in FIGS. 28B and 28G, when the multi-function jaw mechanism 460*c* is in the closed jaw configuration, the distal ends 474*b*, 473*b* of the top and bottom jaw members 462*a*, 462*b* are in contact, whereby at least the top and bottom jaw member suture engaging surfaces 495*d*, 495*f* are in contact.

According to the invention, the top and bottom jaw member tissue engaging surfaces 495*c*, 495*e* can similarly comprise various surface features to facilitate capture and engagement of soft tissue and surgical instruments and devices between the top and bottom tissue engaging surfaces 495*c*, 495*e* and, hence, top and bottom jaw members 462*a*, 462*b*.

As illustrated in FIGS. 28A and 28E, in a preferred embodiment, the top jaw member tissue engaging surface 495*c* comprises a serrated surface.

According to the invention, the top jaw member tissue engaging surface 495*c* can also comprise a substantially smooth surface, as illustrated in FIGS. 28F and 28G.

In a preferred embodiment, top jaw member suture engaging surface 495*d* comprises a substantially smooth surface.

As illustrated in FIGS. 28A and 28H, in a preferred embodiment, the bottom jaw member tissue engaging surface 495*e* comprises a substantially smooth planar surface.

According to the invention, the bottom jaw member tissue engaging surface 495*e* can also comprise a serrated surface that corresponds to or cooperates with, e.g., interlocks with, the serrated surface of the top jaw member tissue engaging surface 495*c*.

According to the invention, any of the top and bottom jaw member tissue engaging surfaces 495*c*, 495*e*, and top and bottom jaw member suture engaging surfaces 495*d*, 495*f* can also comprise functionally textured surfaces.

According to the invention, the textured surfaces comprise a surface roughness (Ra) in the range of approximately 0.5 μm to approximately 25.0 μm, more preferably, an Ra in the range of approximately 1.5 μm to approximately 3.0 μm.

In a preferred embodiment, the distal ends 474*b*, 473*b* of the top and bottom jaw members 462*a*, 462*b* and hence, top and bottom jaw member tissue engaging surfaces 495*c*, 495*e* are thus configured and adapted to engage, grasp and capture at least defined, finite portions of soft tissue proximate the distal ends 474*b*, 473*b* of the top and bottom jaw members 462*a*, 462*b* within a confined surgical site when the soft tissue is advanced into the open jaw mechanism region 465 and/or jaw mechanism suture-tissue capture region 465' defined by the top and bottom jaw members 462*a*, 462*b* of the multi-function jaw mechanism 460*c* and the multi-function jaw mechanism 460*c* transitions to and is in the closed jaw configuration illustrated in FIG. 28B.

In a preferred embodiment, the distal ends 474*b*, 473*b* of the top and bottom jaw members 462*a*, 462*b* and hence, top and bottom jaw member tissue engaging surfaces 495*c*, 495*e* are also configured and adapted to engage, grasp and capture surgical instruments and devices proximate the distal ends 474*b*, 473*b* of the top and bottom jaw members 462*a*, 462*b* when the surgical instruments and devices are advanced into the open jaw mechanism region 465 and/or jaw mechanism suture-tissue capture region 465' defined by the top and bottom jaw members 462*a*, 462*b* of the multi-function jaw mechanism 460*c* and the multi-function jaw mechanism 460*c* transitions to and is in the closed jaw configuration illustrated in FIG. 28B.

As indicated above, in a preferred embodiment, the top and bottom jaw member suture engaging surfaces 495*d*, 495*f* comprise smooth planar surfaces to facilitate engaging, grasping and capturing finite portions of sutures, and soft tissue.

As also indicated above, the top and bottom jaw member suture engaging surfaces 495*d*, 495*f* can also comprise textured planar surfaces to further facilitate engaging, grasping and capturing finite portions of sutures, and soft tissue.

Figure 28I:
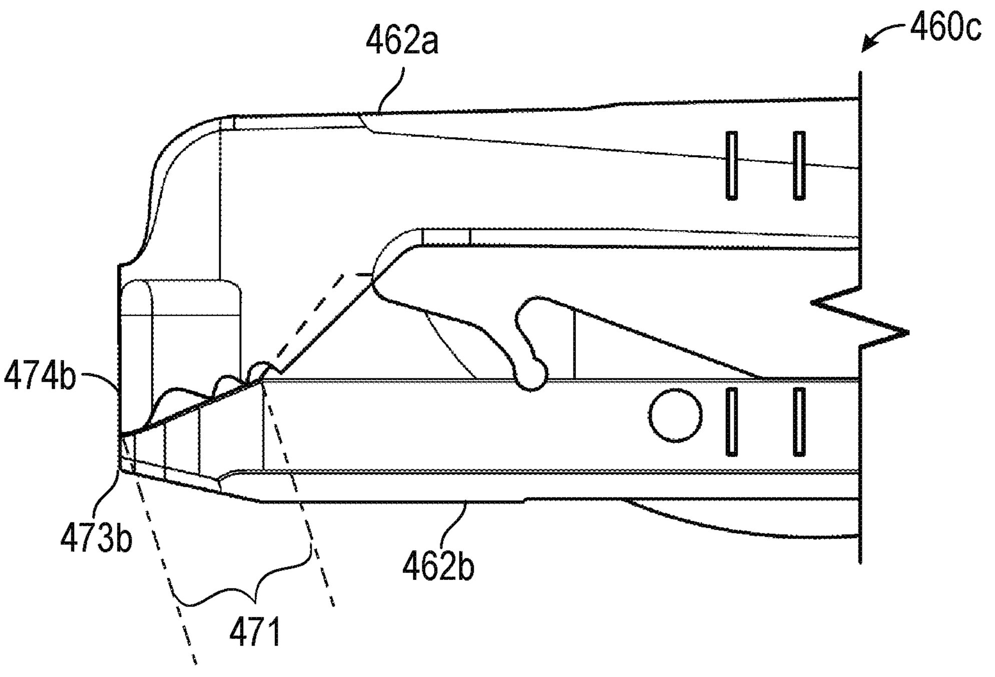
FIG. 28I is a partial side plan view of the multi-function jaw mechanism shown in FIG. 28B, in accordance with the invention.

As also indicated above and illustrated in FIGS. 28B and 28I, when the multi-function jaw mechanism 460*c* is in the closed jaw configuration, at least the top and bottom jaw member suture engaging surfaces 495*d*, 495*f* are in contact.

Thus, in a preferred embodiment, the distal ends 474*b*, 473*b* of the top and bottom jaw members 462*a*, 462*b* and hence, top and bottom jaw member suture engaging surfaces 495*d*, 495*f* are thus configured and adapted to engage, grasp and capture at least a defined, finite portion of a suture proximate the distal ends 474*b*, 473*b* of the top and bottom jaw members 462*a*, 462*b* within a confined surgical site when the suture is advanced into the open jaw mechanism region 465 and/or jaw mechanism suture-tissue capture region 465' defined by the top and bottom jaw members 462*a*, 462*b* of the multi-function jaw mechanism 460*c* and the multi-function jaw mechanism 460*c* transitions to and is in the closed jaw configuration illustrated in FIG. 28B.

Referring now to FIGS. 29A-29D, FIGS. 30A-30E, and FIGS. 31A-31D, there are shown further embodiments of the multi-function jaw mechanism 460*c* described above.

Referring first to FIGS. 29A-29D, there is shown a first alternative embodiment of multi-function jaw mechanism 460*c* (now denoted "460*d*").

Figure 29A:
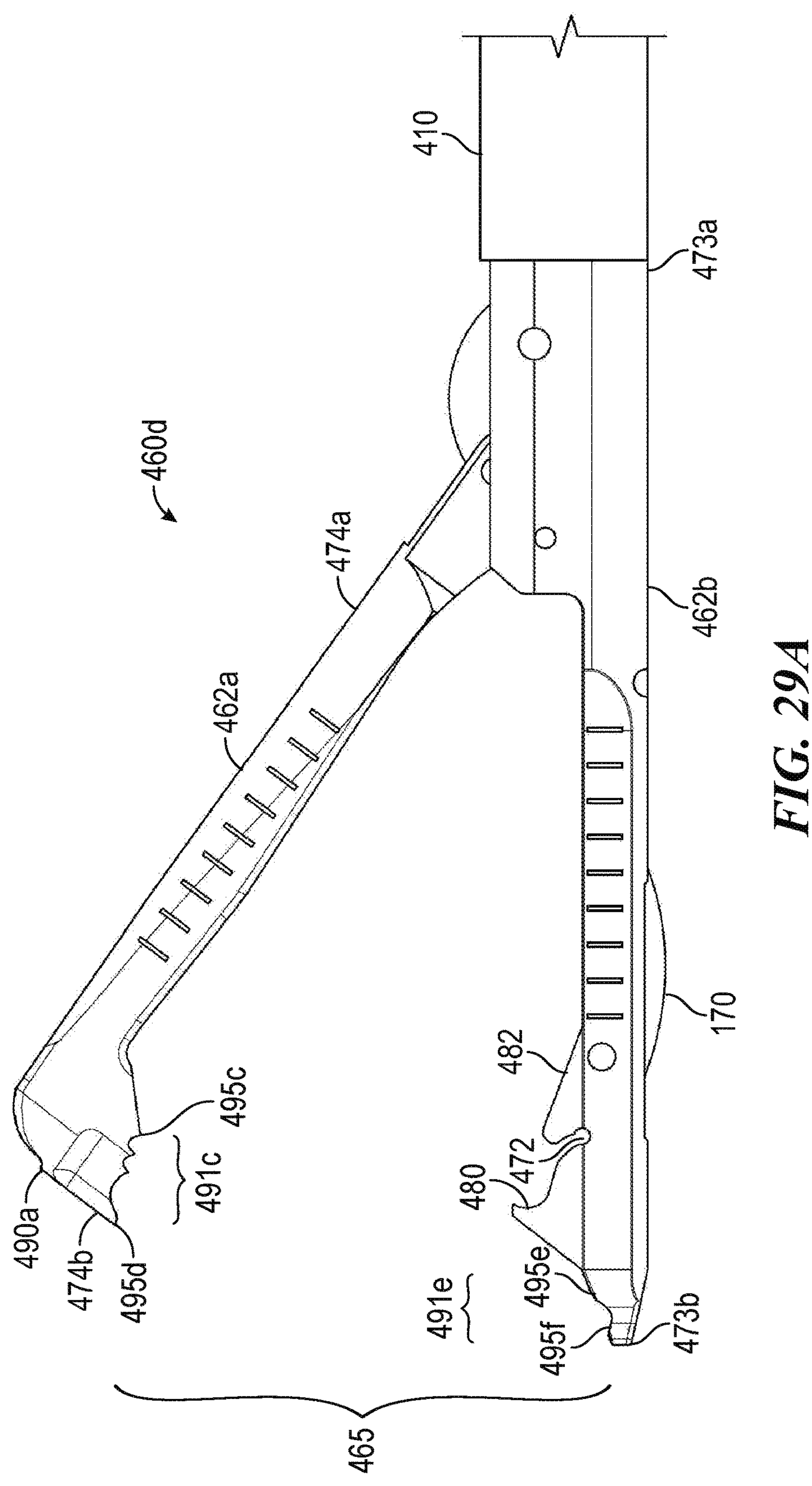
FIG. 29A is a side plan view of another embodiment of a multi-function jaw mechanism in an open jaw configuration, in accordance with the invention.
Figure 29B:
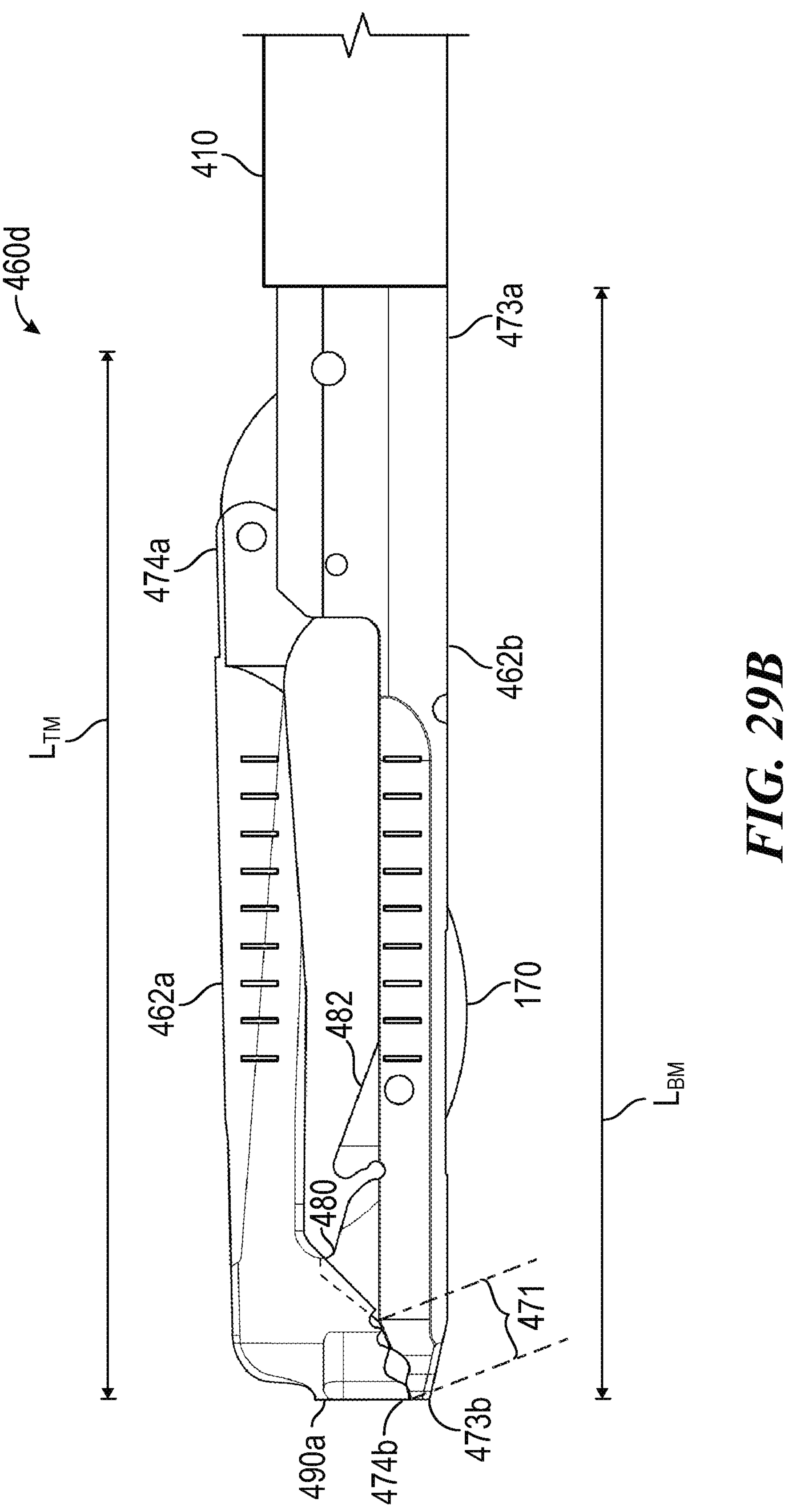
FIG. 29B is a further side plan view of the multi-function jaw mechanism shown in FIG. 29A in a fully closed jaw configuration, in accordance with the invention.
Figure 29C:
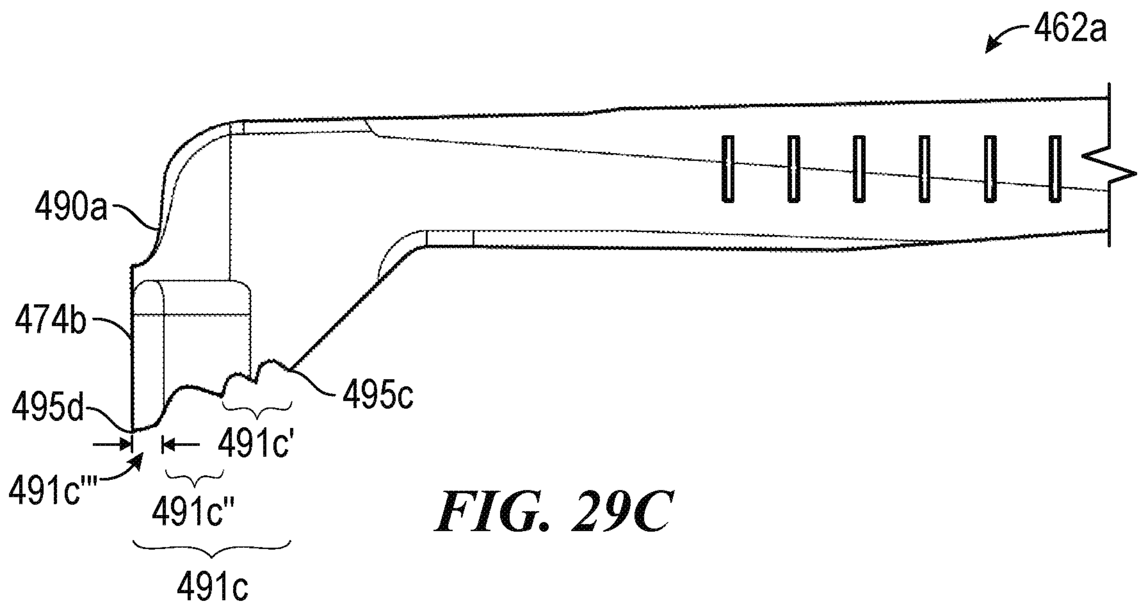
FIG. 29C is a partial side plan view of the top jaw member of the multi-function jaw mechanism shown in FIG. 29A, in accordance with the invention.

As illustrated in FIGS. 29A and 29C, the multi-function jaw mechanism similarly comprises suture-tissue engagement region 491*c* on the distal end 474*b* of the top jaw member 462*a*, i.e., top jaw member suture-tissue engagement region 491*c*.

Figure 29D:
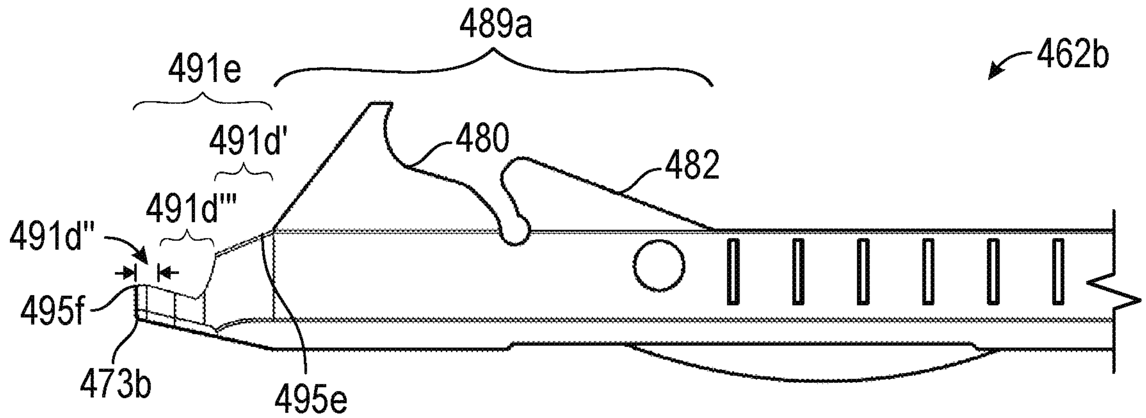
FIG. 29D is a partial side plan view of the bottom jaw member of the multi-function jaw mechanism shown in FIG. 29A, in accordance with the invention.

However, as illustrated in FIGS. 29A and 29D, the multi-function jaw mechanism comprises a further embodiment of a suture-tissue engagement region (denoted "491*e*") on the distal end 473*b* of the bottom jaw member 462*b*.

In a preferred embodiment, the bottom jaw member suture-tissue engagement region 491*e* similarly comprises the bottom jaw member tissue engagement region 491*d'* comprising bottom jaw member tissue engaging surface 495*e* illustrated in FIGS. 28A and 28H, which as indicated above, is configured and adapted to grasp at least soft tissue and, hence, sutures and surgical instruments and devices, and the bottom jaw member suture engagement region 491*d''* comprising suture engaging surface 495*f* (also illustrated in FIGS. 28A and 28H), which, as also indicated above, is configured and adapted to removably engage suture and, hence, soft tissue and surgical instruments and devices.

However, as illustrated in FIGS. 29A, 29B and 29D, in a preferred embodiment, the bottom jaw member suture-tissue engagement region 491*e* further comprises a bottom jaw member recess 491*d''*, which is disposed between the bottom jaw member suture engaging surface 495*f* and bottom jaw member tissue engaging surface 495*e*.

In a preferred embodiment, the depth of the bottom jaw member recess 491*d'''* is in the range of at least approximately 0.20 mm to approximately 1.50 mm, more preferably, the depth of the bottom jaw member recess 491*d''* is at least approximately 0.25 mm to approximately 0.75 mm.

According to the invention, the bottom jaw member recess 491*d''* is configured to securely capture suture (and tissue) when the multi-function jaw mechanism 460*d* is in a closed jaw configuration, as illustrated in FIG. 29B.

Referring now to FIGS. 30A-30E, there is shown a second alternative embodiment of multi-function jaw mechanism 460*c* (now denoted "460*e*").

Figure 30A:
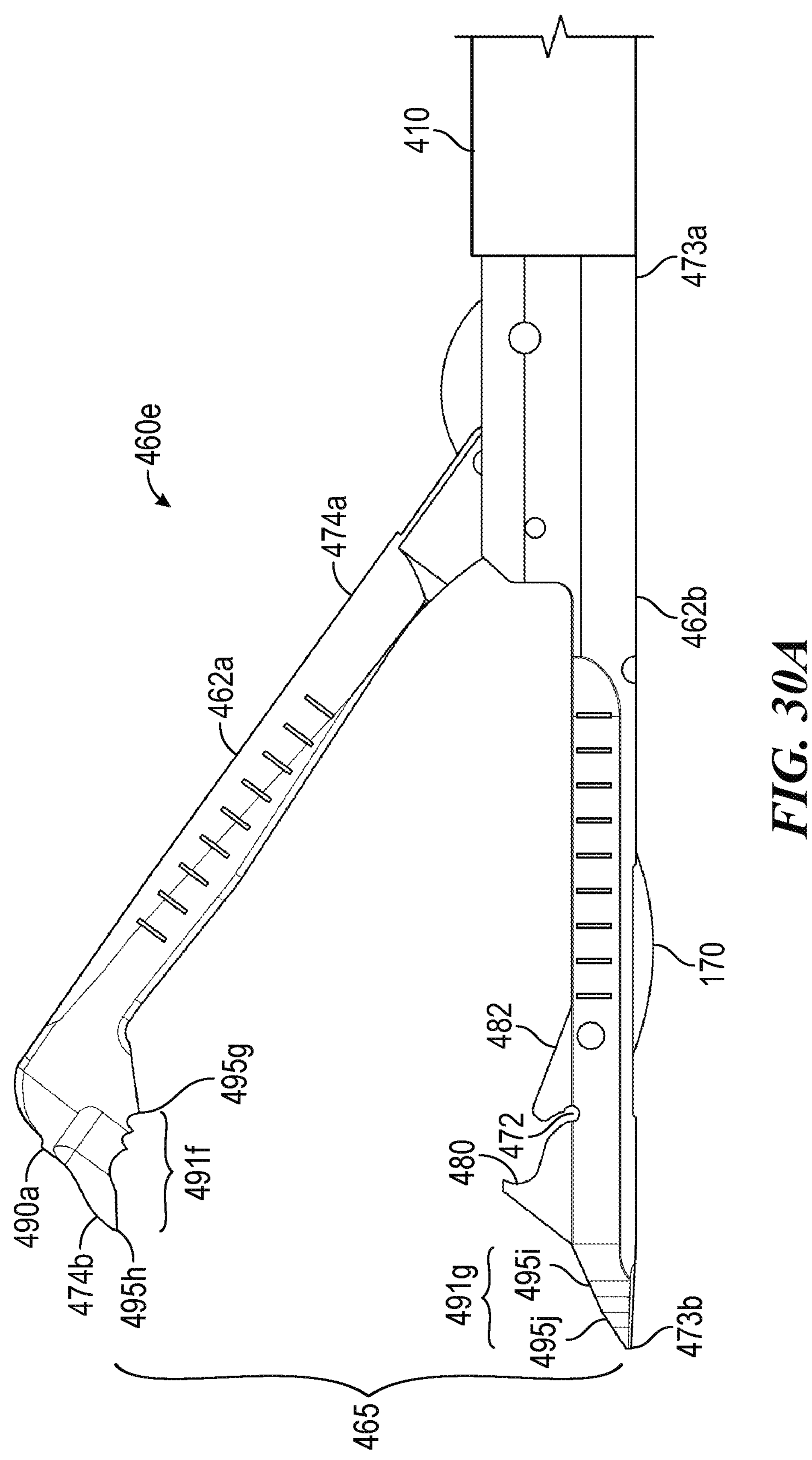
FIG. 30A is a side plan view of another embodiment of a multi-function jaw mechanism in a fully open jaw configuration, in accordance with the invention.
Figure 30B:
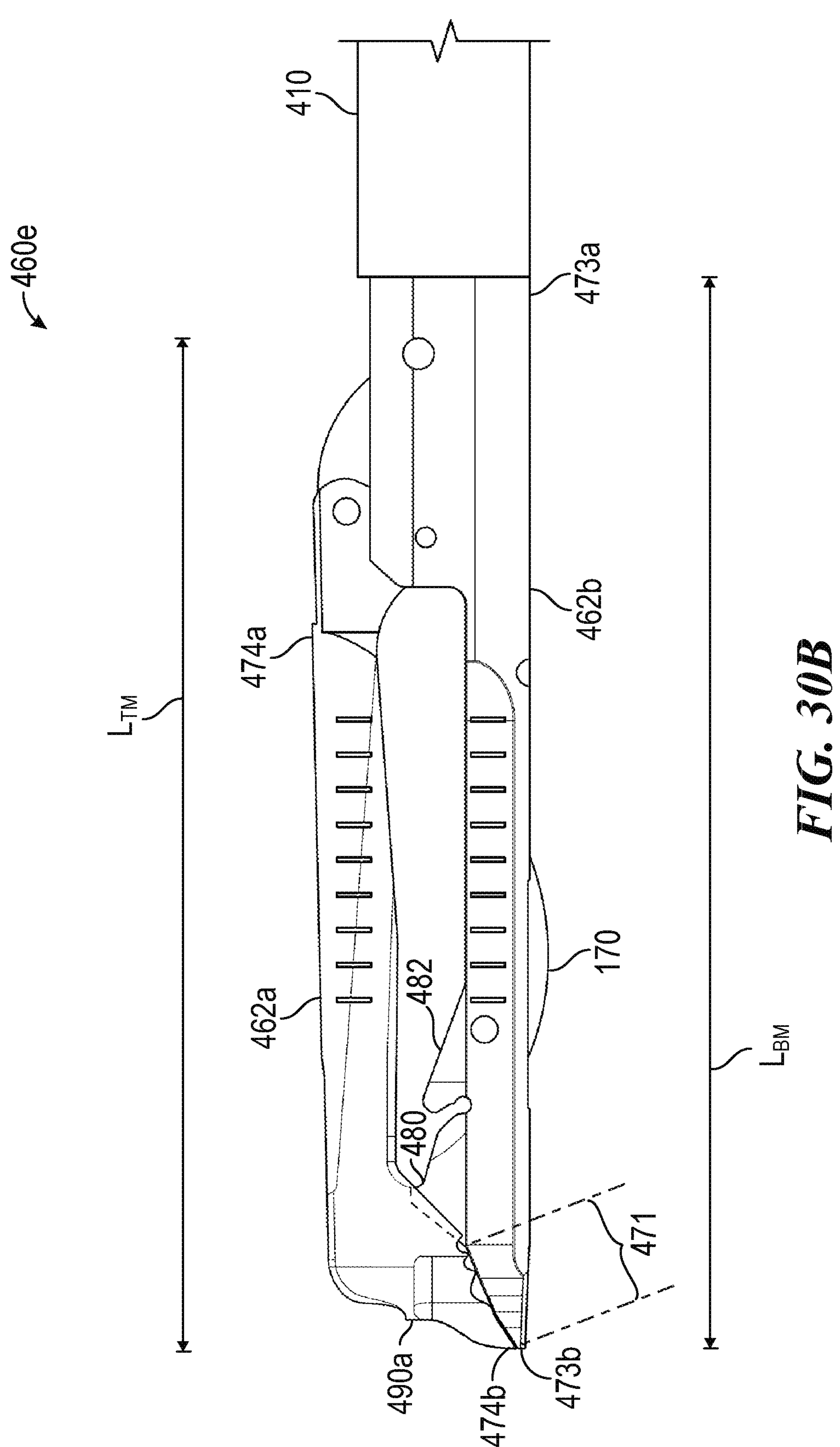
FIG. 30B is a further side plan view of the multi-function jaw mechanism shown in FIG. 30A in a fully closed jaw configuration, in accordance with the invention.
Figure 30C:
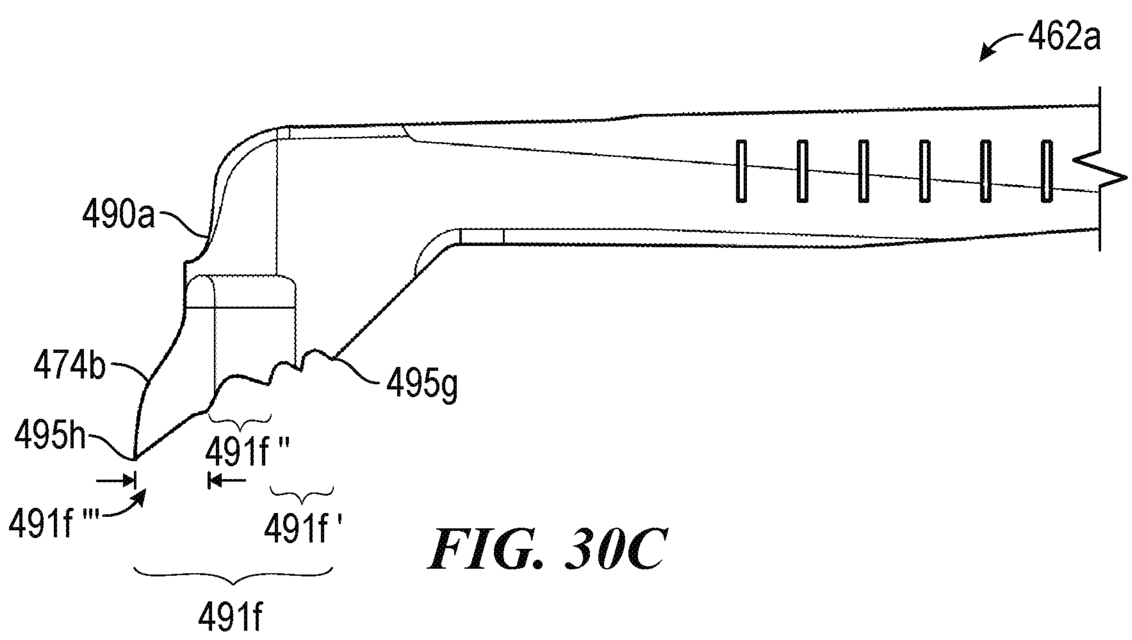
FIG. 30C is a partial side plan view of the top jaw member of the multi-function jaw mechanism shown in FIG. 30A, in accordance with the invention.

As illustrated in FIGS. 30A and 30C, the multi-function jaw mechanism 460*e* comprises a further embodiment of a suture-tissue engagement region on the distal end 474*b* of the top jaw member 462*a* (denoted "491*f*").

As also illustrated in FIGS. 30A and 30C, in a preferred embodiment, the top jaw member suture-tissue engagement region 491*f* similarly comprises a dual zone suture-tissue engagement region comprising a top jaw member tissue engagement region (denoted 491*f'*) and a top jaw member suture engagement region (denoted 491*f''*).

As further illustrated in FIGS. 30A and 30C, in a preferred embodiment, the top jaw member suture-tissue engagement region 491*f* similarly comprises a top jaw member recess (in this embodiment, denoted "491*f*"").

In a preferred embodiment, the depth of the top jaw member recess 491*f*" is similarly in the range of at least approximately 0.10 mm to approximately 1.5 mm, more preferably, the depth of the top jaw member recess 491*f*" is in the range of at least approximately 0.25 mm to approximately 0.75 mm.

As further illustrated in FIGS. 30A and 30C, in a preferred embodiment, the top jaw member suture engagement region 491*f*'" projects outward from the top jaw member suture-tissue engagement region 491*f*, wherein the top jaw member suture engagement region 491*f*" and top jaw member tissue engagement region 491*f*' define two (2) separate planes, i.e. a top suture-tissue engagement region plane and a top jaw member suture engagement region plane.

In a preferred embodiment, the top jaw member suture engagement region 491*f*" similarly extends proximally from the distal end 474*b* of the top jaw member 462*a* no greater than approximately 4.0 mm, more preferably, the top jaw member suture engagement region 491*f*'" similarly extends proximally from the distal end 474*b* of the top jaw member 462*a* no greater than approximately 2.0 mm.

In a preferred embodiment, the top jaw member suture engagement region 491*f*" similarly has a width in a lateral direction, as denoted by "w" in FIG. 28C, no greater than approximately 4.0 mm, more preferably, the top jaw member suture engagement region 491*f*" has a width in a lateral direction no greater than approximately 2.0 mm.

In a preferred embodiment, the top jaw member suture engagement region 491*f*'" also projects outward relative to (and, hence, from) the top jaw member tissue engagement region 491*f*' no greater than approximately 4.0 mm, more preferably, no greater than approximately 2.0 mm, even more preferably, no greater than approximately 1.0 mm.

In a preferred embodiment, the top jaw member tissue engagement region 491*f*' comprises a tissue engaging surface 495*g* that is similarly configured and adapted to grasp at least soft tissue and, hence, sutures and surgical instruments and devices.

In a preferred embodiment, the top jaw member suture engagement region 491*f*" comprises a suture engaging surface 495*h* that is similarly configured and adapted to at least removably engage suture and, thus, also grasp and engage soft tissue and surgical instruments and devices.

Figure 30D:
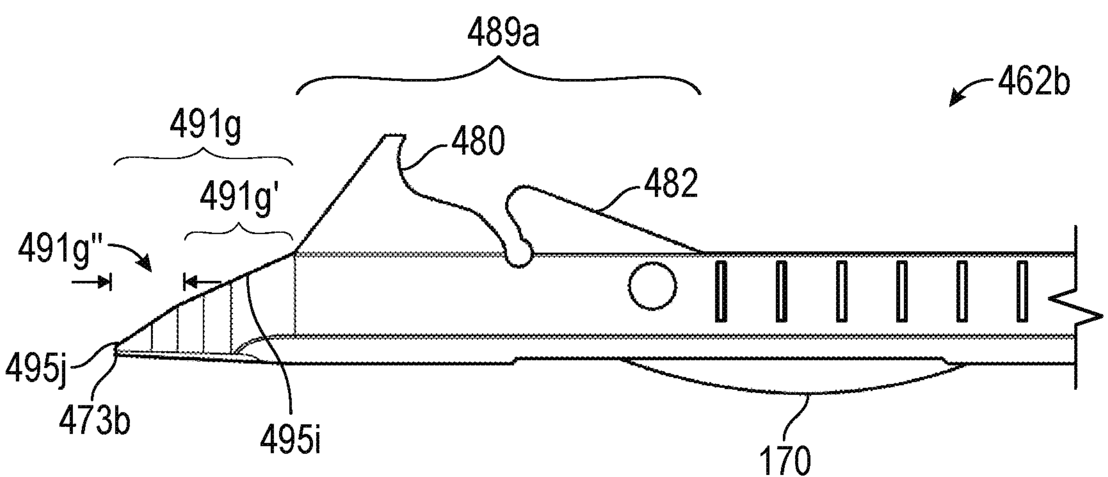
FIG. 30D is a partial side plan view of the bottom jaw member of the multi-function jaw mechanism shown in FIG. 30A, in accordance with the invention.

As illustrated in FIGS. 30A and 30D, in a preferred embodiment, the multi-function jaw mechanism 460*e* also comprises a further embodiment of a suture-tissue engagement region on the distal end 473*b* of the bottom jaw member 462*b* (denoted "491*g*").

In a preferred embodiment, the bottom jaw member suture-tissue engagement region 491*g* also comprises a dual zone suture-tissue engagement region comprising a bottom jaw member tissue engagement region (denoted 491*g*') and a bottom jaw member suture engagement region (denoted 491*g*").

As further illustrated in FIGS. 30A and 30D, in a preferred embodiment, the bottom jaw member suture engagement region 491*g*" and bottom jaw member tissue engagement region 491*g*' similarly define two (2) separate planes, i.e., a bottom jaw member tissue engagement region plane and a bottom jaw member suture engagement region plane.

Figure 30E:
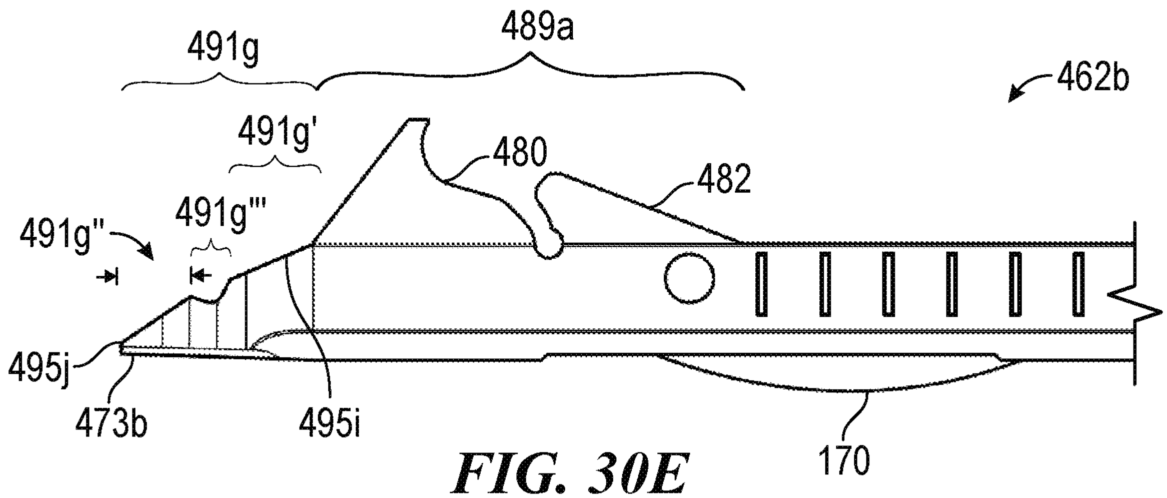
FIG. 30E is a partial side plan view of another embodiment of a bottom jaw member of the multi-function jaw mechanism shown in FIG. 30A, in accordance with the invention.

As illustrated in FIG. 30E, in some embodiments, the bottom jaw member suture-tissue engagement region 491*g* similarly comprises a bottom jaw member recess (in this embodiment, denoted 491*g*"), which is disposed between the bottom jaw member tissue engagement region 491*g*' and a bottom jaw member suture engagement region 491*g*".

In a preferred embodiment, the depth of the bottom jaw member recess 491*g*" is similarly in the range of at least approximately 0.10 mm to approximately 1.5 mm, more preferably, the depth of the bottom jaw member recess 491*g*'" is at least approximately 0.25 mm to approximately 0.75 mm.

In a preferred embodiment, the bottom jaw member tissue engagement region 491*g*' comprises a bottom jaw member tissue engaging surface 495*i* that is similarly configured and adapted to grasp at least soft tissue and, hence, sutures and surgical instruments and devices.

In a preferred embodiment, the bottom jaw member suture engagement region 491*g*" comprises a bottom jaw member suture engaging surface 495*j* that is similarly configured and adapted to removably engage suture and, hence, soft tissue and surgical instruments and devices.

As illustrated in FIG. 30B, in a preferred embodiment, the suture-tissue engagement regions 491*f*, 491*g* are similarly positioned on the top and bottom jaw members 462*a*, 462*b*, wherein the suture-tissue engagement regions 491*f*, 491*g*, and, thus, tissue engaging surfaces 495*g*, 495*i*, and suture engaging surfaces 495*h*, 495*j* are aligned when the multi-function jaw mechanism 460*e* is in a closed configuration, whereby the top and bottom jaw member suture-tissue engagement regions 491*f*, 491*g* of the top and bottom jaw members 462*a*, 462*b* are similarly aligned and form jaw mechanism suture-tissue engagement region 471 (see FIG. 30B), and during transition of the multi-function jaw mechanism 460*e* to the closed jaw configuration, i.e., the partially open jaw configuration, the suture-tissue engagement regions 491*f*, 491*g* of the top and bottom jaw members 462*a*, 462*b* similarly provide jaw mechanism suture-tissue capture region 465', as shown in FIG. 28D, which is similarly configured to receive and, hence, facilitate grasping, capture and engagement of soft tissue, sutures and surgical instruments and devices therein.

In a preferred embodiment, when the multi-function jaw mechanism 460*e* is in a closed configuration, the jaw mechanism suture-tissue engagement region 471 similarly extends proximally less than 20% of the length $L_{TM}$ of the top jaw member 462*a* from the distal end 474*b* thereof or the length $L_{BM}$ of the bottom jaw member 462*b* from the distal end 473*b* thereof.

In a preferred embodiment, the top jaw member suture-tissue engagement region 491*f* similarly extends proximally from the distal end 474*b* of the top jaw member 462*a* no greater than 12.0 mm, more preferably, no greater than 8.0 mm, even more preferably, no greater than 6.0 mm.

In a preferred embodiment, the bottom jaw member suture-tissue engagement region 491*g* similarly extends proximally from the distal end 473*b* of the bottom jaw member 462*b* no greater than 12.0 mm, more preferably, no greater than 8.0 mm, even more preferably, no greater than 6.0 mm.

As further illustrated in FIG. 30B, when the multi-function jaw mechanism 460*e* is in the closed jaw configuration, at least the top and bottom suture engaging surfaces 495*h*, 495*j* are in contact.

According to the invention, the top and bottom jaw member tissue engaging surfaces 495*g*, 495*i* can similarly comprise various surface features to facilitate capture and engagement of soft tissue and surgical instruments and devices between the top and bottom jaw member tissue engaging surfaces 495*g*, 495*i*, and, hence, the top and bottom jaw members 462*a*, 462*b*.

As illustrated in FIGS. 30A and 30C, in a preferred embodiment, the top jaw member tissue engaging surface 495*g* comprises a serrated surface.

As illustrated in FIGS. 30A and 30D, in a preferred embodiment, the "mating" bottom jaw member tissue engaging surface 495*i* comprises a substantially smooth planar surface.

According to the invention, the top jaw member tissue engaging surface 495*g* can also comprise a substantially smooth planar surface, as illustrated in FIG. 28F.

In a preferred embodiment, the top and bottom jaw member suture engaging surfaces 495*h*, 495*j* comprise substantially smooth surfaces.

According to the invention, the bottom tissue engaging surface 495*i* can also comprise a serrated surface that corresponds to or cooperates with, e.g., interlocks with, the serrated surface of the top jaw member tissue engaging surface 495*g*.

In a preferred embodiment, the distal ends 474*b*, 473*b* of the top and bottom jaw members 462*a*, 462*b* and hence, top and bottom tissue engaging surfaces 495*g*, 495*i* are thus similarly configured and adapted to engage, grasp and capture at least defined, finite portions of soft tissue proximate the distal ends 474*b*, 473*b* of the top and bottom jaw members 462*a*, 462*b* within a confined surgical site when the soft tissue is advanced into the open jaw mechanism region 465 and/or jaw mechanism suture-tissue capture region 465' defined by the top and bottom jaw members 462*a*, 462*b* of the multi-function jaw mechanism 460*e* and the multi-function jaw mechanism 460*e* transitions to and is in the closed jaw configuration illustrated in FIG. 30B.

In a preferred embodiment, the distal ends 474*b*, 473*b* of the top and bottom jaw members 462*a*, 462*b* and hence, top and bottom tissue engaging surfaces 495*g*, 495*i* are similarly also configured and adapted to engage, grasp and capture surgical instruments and devices proximate the distal ends 474*b*, 473*b* of the top and bottom jaw members 462*a*, 462*b* when the surgical instruments and devices are advanced into the open jaw mechanism region 465 and/or jaw mechanism suture-tissue capture region 465' defined by the top and bottom jaw members 462*a*, 462*b* of the multi-function jaw mechanism 460*e* and the multi-function jaw mechanism 460*e* transitions to and is in the closed jaw configuration illustrated in FIG. 30B.

As indicated above, in a preferred embodiment, the top and bottom jaw member suture engaging surfaces 495*h*, 495*j* comprise smooth planar surfaces to facilitate engaging, grasping and capturing finite portions of sutures, and soft tissue.

According to the invention, the top and bottom jaw member suture engaging surfaces 495*h*, 495*j* can also comprise the functionally textured surfaces described above to further facilitate engaging, grasping and capturing finite portions of sutures, and soft tissue.

As also indicated above and illustrated in FIG. 30B, when the multi-function jaw mechanism 460*e* is in the closed jaw configuration, at least the top and bottom suture engaging surfaces 495*h*, 495*j* are in contact.

Thus, in a preferred embodiment, when the multi-function jaw mechanism 460*e* transitions to and is in a closed jaw configuration, as illustrated in FIG. 30B, the suture engaging surfaces 495*h*, 495*j* of the top and bottom jaw members 462*a*, 462*b* will similarly engage, grasp and capture at least a defined, finite portion of a suture within a confined surgical site when the suture is advanced into the open jaw mechanism region 465 and/or jaw mechanism suture-tissue capture region 465' defined by the top and bottom jaw members 462*a*, 462*b* of the multi-function jaw mechanism 460*e*.

Referring now to FIGS. 31A-31D, there is shown a third alternative embodiment of multi-function jaw mechanism 460*c* (now denoted "460*f*").

Figure 31A:
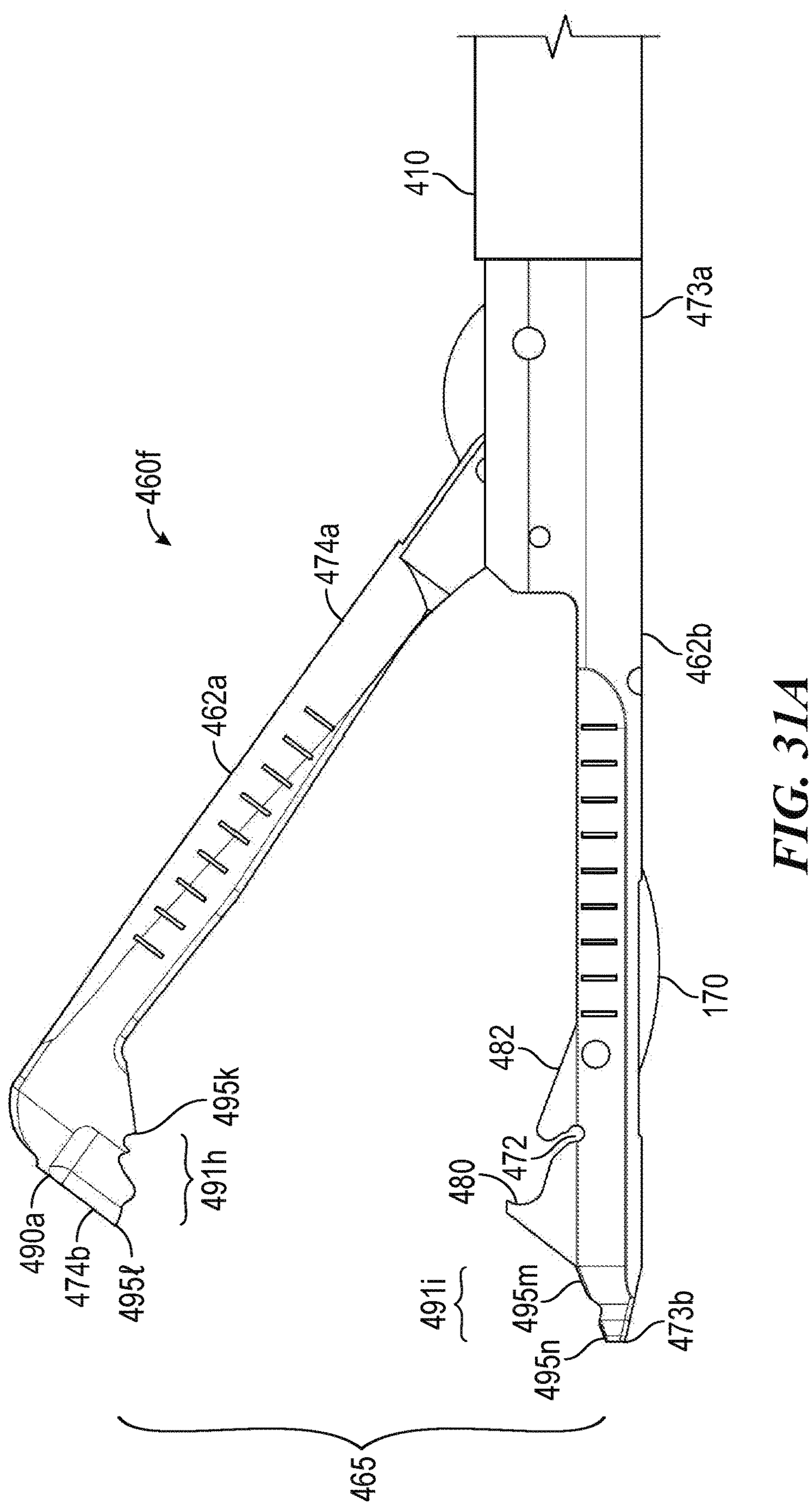
FIG. 31A is a side plan view of another embodiment of a multi-function jaw mechanism in a fully open jaw configuration, in accordance with the invention.
Figure 31B:
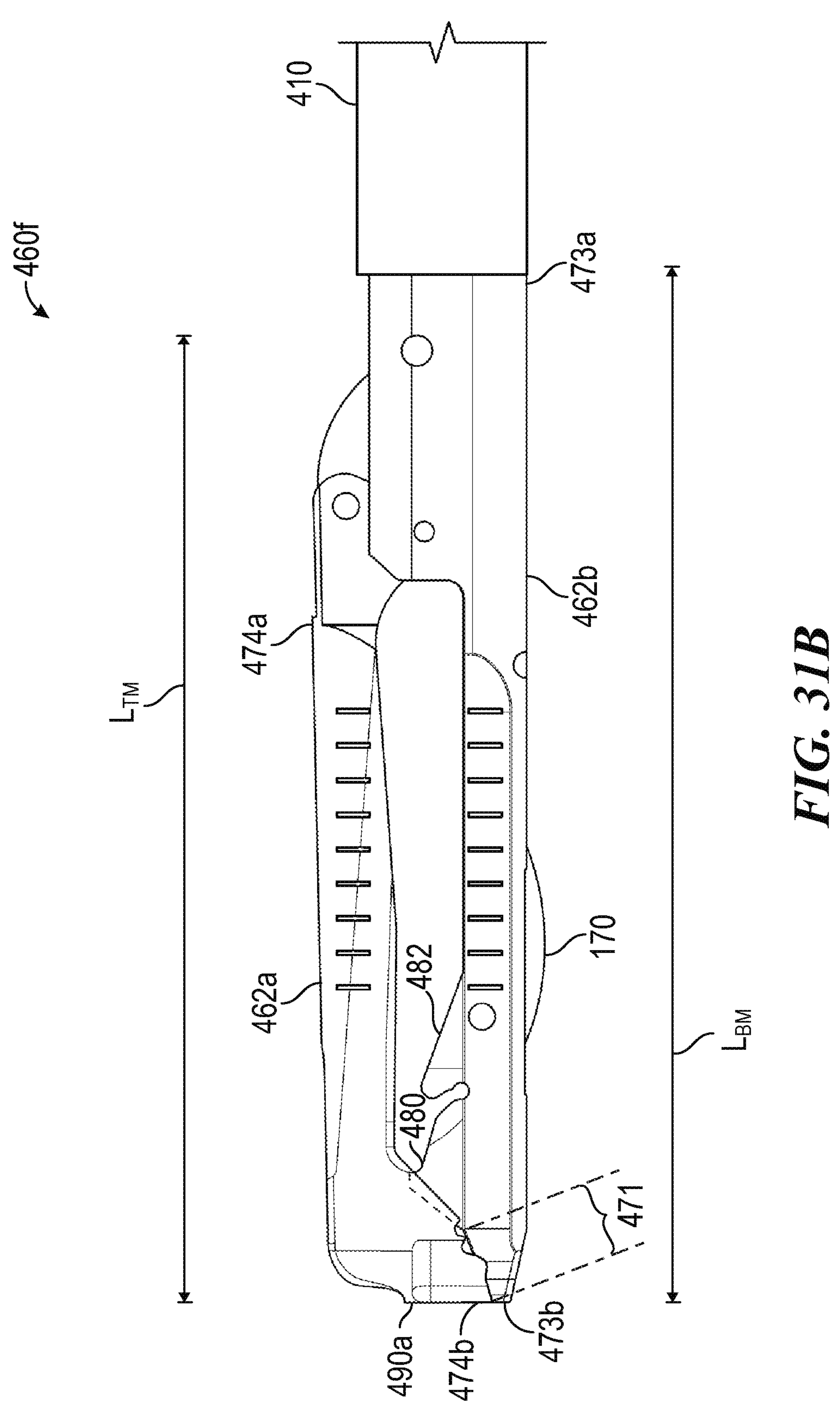
FIG. 31B is a further side plan view of the multi-function jaw mechanism shown in FIG. 31A in a fully closed jaw configuration, in accordance with the invention.
Figure 31C:
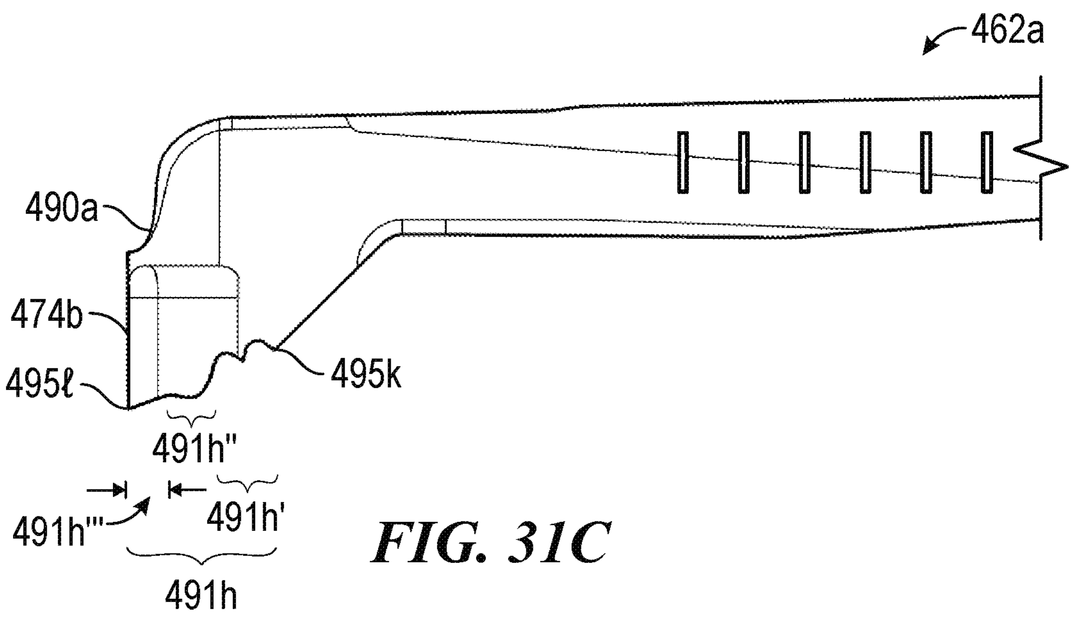
FIG. 31C is a partial side plan view of the top jaw member of the multi-function jaw mechanism shown in FIG. 31A, in accordance with the invention.

As illustrated in FIGS. 31A and 31C, the multi-function jaw mechanism 460*f* comprises a further embodiment of a suture-tissue engagement region on the distal end 474*b* of the top jaw member 462*a* (denoted "491*h*").

As also illustrated in FIGS. 31A and 31C, in a preferred embodiment, the top jaw member suture-tissue engagement region 491*h* similarly comprises a dual zone suture-tissue engagement region comprising a top jaw member tissue engagement region (denoted 491*h*') and a top jaw member suture engagement region (denoted 491*h*").

As further illustrated in FIGS. 31A and 31C, in a preferred embodiment, the top jaw member suture-tissue engagement region 491*h* comprises a top jaw member projection (denoted "491*h*") disposed between the top jaw member tissue engagement region 491*h*' and the top jaw member suture engagement region 491*h*''', which, as discussed below, is sized and configured to be received in the bottom jaw member jaw member projection slot (or seat) (denoted "491*i*").

In a preferred embodiment, the top jaw member suture engagement region 491*h*" similarly extends proximally from the distal end 474*b* of the top jaw member 462*a* no greater than approximately 4.0 mm, more preferably, the top jaw member suture engagement region 491*h*''' similarly extends proximally from the distal end 474*b* of the top jaw member 462*a* no greater than approximately 2.0 mm.

In a preferred embodiment, the top jaw member suture engagement region 491*h*" similarly has a width in a lateral direction, as denoted by "w" in FIG. 28C, no greater than approximately 4.0 mm, more preferably, the top jaw member suture engagement region 491*h*" has a width in a lateral direction no greater than approximately 2.0 mm.

In a preferred embodiment, the top jaw member tissue engagement region 491*h*' comprises a tissue engaging surface 495*k* that is similarly configured and adapted to grasp at least soft tissue and, hence, sutures and surgical instruments and devices.

In a preferred embodiment, the top jaw member suture engagement region 491*h*" comprises a suture engaging surface 495€ that is similarly configured and adapted to at least removably engage suture and, thus, also grasp and engage soft tissue and surgical instruments and devices.

Figure 31D:
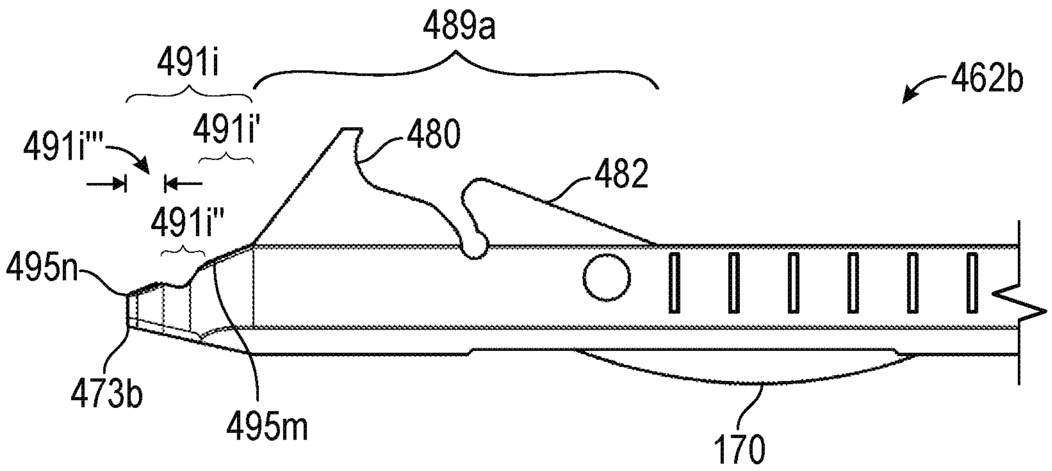
FIG. 31D is a partial side plan view of the bottom jaw member of the multi-function jaw mechanism shown in FIG. 31A, in accordance with the invention.

As illustrated in FIGS. 31A and 31D, in a preferred embodiment, the multi-function jaw mechanism 460*f* also comprises a further embodiment of a suture-tissue engagement region on the distal end 473*b* of the bottom jaw member 462*b* (denoted "491*i*").

In a preferred embodiment, the bottom jaw member suture-tissue engagement region 491*i* also comprises a dual zone suture-tissue engagement region comprising a bottom jaw member tissue engagement region (denoted "491*i*") and a bottom jaw member suture engagement region (denoted "491*i*" " ").

As further illustrated in FIGS. 31A and 31D, in a preferred embodiment, the bottom jaw member suture engagement region 491*i*''' and bottom jaw member tissue engagement region 491*i*' similarly define two (2) separate planes, i.e., a bottom jaw member tissue engagement region plane and a bottom jaw member suture engagement region plane.

According to the invention, the bottom jaw member suture engagement region 491*i*" and bottom jaw member tissue engagement region 491*i*' can also define and, hence, comprise a single plane.

As illustrated in FIG. 31D, in a preferred embodiment, the bottom jaw member suture-tissue engagement region 491*i* also comprises the aforementioned bottom jaw member jaw member projection slot (or seat) 491*i*", which is disposed between the bottom jaw member tissue engagement region 491*i*' and bottom jaw member suture engagement region 491*i*".

In a preferred embodiment, the bottom jaw member jaw member projection slot (or seat) 491*i*" is sized and configured to receive the top jaw member projection 491 h" therein.

In a preferred embodiment, the bottom jaw member tissue engagement region 491*i*' comprises a bottom jaw member tissue engaging surface 495*m* that is similarly configured and adapted to grasp at least soft tissue and, hence, sutures and surgical instruments and devices.

In a preferred embodiment, the bottom jaw member suture engagement region 491*i*'" comprises a bottom jaw member suture engaging surface 495*n* that is similarly configured and adapted to removably engage suture and, hence, soft tissue and surgical instruments and devices.

As illustrated in FIG. 31B, in a preferred embodiment, the suture-tissue engagement regions 491*h*, 491*i* are similarly positioned on the top and bottom jaw members 462*a*, 462*b*, wherein the suture-tissue engagement regions 491*h*, 491*i*, and, thus, tissue engaging surfaces 495*k*, 495*m*, and suture engaging surfaces 495€, 495*n* are aligned when the multi-function jaw mechanism 460*f* is in a closed configuration, whereby the top and bottom jaw member suture-tissue engagement regions 491*h*, 491*i* of the top and bottom jaw members 462*a*, 462*b* are similarly aligned and form jaw mechanism suture-tissue engagement region 471 (see FIG. 31B), and during transition of the multi-function jaw mechanism 460*f* to the closed jaw configuration, i.e., the partially open jaw configuration, the top and bottom suture-tissue engagement regions 491*h*, 491*i* similarly provide jaw mechanism suture-tissue capture region 465', as shown in FIG. 28D, which is similarly configured to receive and, hence, facilitate grasping, capture and engagement of soft tissue, sutures and surgical instruments and devices therein.

In a preferred embodiment, when the multi-function jaw mechanism 460*f* is in a closed configuration, the jaw mechanism suture-tissue engagement region 471 similarly extends proximally less than 20% of the length $L_{TM}$ of the top jaw member 462*a* from the distal end 474*b* thereof or the length $L_{BM}$ of the bottom jaw member 462*b* from the distal end 473*b* thereof.

In a preferred embodiment, the top jaw member suture-tissue engagement region 491*h* similarly extends proximally from the distal end 474*b* of the top jaw member 462*a* no greater than 12.0 mm, more preferably, no greater than 8.0 mm, even more preferably, no greater than 6.0 mm.

In a preferred embodiment, the bottom jaw member suture-tissue engagement region 491*i* similarly extends proximally from the distal end 473*b* of the bottom jaw member 462*b* no greater than 12.0 mm, more preferably, no greater than 8.0 mm, even more preferably, no greater than 6.0 mm.

As further illustrated in FIG. 31B, when the multi-function jaw mechanism 460*f* is in the closed jaw configuration, at least the top and bottom suture engaging regions 491*h*", 491*i*"" and, hence, top and bottom jaw member suture engaging surfaces 495€, 495*n* are in contact.

As illustrated in FIG. 31C, in a preferred embodiment, the top jaw member suture engaging surface 495€ comprises a substantially smooth planar surface.

As illustrated in FIG. 31D, in a preferred embodiment, the "mating" bottom jaw member suture engaging surface 495*n* also comprises a substantially smooth planar surface.

According to the invention, the top and bottom jaw member suture engaging surfaces 495€, 495*n* can similarly comprise various surface features to facilitate capture and engagement of sutures (and soft tissue and surgical instruments and devices) between the top and bottom jaw member suture-tissue engagement regions 491*h*, 491*i*, and, hence, the top and bottom jaw members 462*a*, 462*b*.

In a preferred embodiment, the distal ends 474*b*, 473*b* of the top and bottom jaw members 462*a*, 462*b* and hence, top and bottom jaw member suture engaging surfaces 495€, 495*n* are thus similarly configured and adapted to engage, grasp and capture sutures and finite portions of soft tissue proximate the distal ends 474*b*, 473*b* of the top and bottom jaw members 462*a*, 462*b* within a confined surgical site when the sutures and soft tissue are advanced into the open jaw mechanism region 465 and/or jaw mechanism suture-tissue capture region 465' defined by the top and bottom jaw members 462*a*, 462*b* of the multi-function jaw mechanism 460*f* and the multi-function jaw mechanism 460*f* transitions to and is in the closed jaw configuration illustrated in FIG. 31B.

As illustrated in FIG. 31C, in a preferred embodiment, the top jaw member tissue engaging surface 495*k* comprises a serrated surface.

As illustrated in FIG. 31D, in a preferred embodiment, the "mating" bottom jaw member tissue engaging surface 495*m* comprises a substantially smooth planar surface.

According to the invention, the bottom tissue engaging surface 495*m* can also comprise a serrated surface that corresponds to or cooperates with, e.g., interlocks with, the serrated surface of the top jaw member tissue engaging surface 495*k*.

According to the invention, the top jaw member tissue engaging surface 495*k* can also comprise a substantially smooth planar surface, as illustrated in FIG. 28F.

Thus, in some embodiments, the top and bottom jaw member tissue engaging surfaces 495*k*, 495*m* comprise substantially smooth planar surfaces.

According to the invention, the top and bottom jaw member tissue engaging surfaces 495*k*, 495*m* can similarly comprise various surface features to facilitate capture and engagement of soft tissue and surgical instruments and devices between the top and bottom jaw member suture-tissue engagement regions 491*h*, 491*i*, and, hence, the top and bottom jaw members 462*a*, 462*b*.

In a preferred embodiment, the distal ends 474*b*, 473*b* of the top and bottom jaw members 462*a*, 462*b* and hence, top and bottom tissue engaging surfaces 495*k*, 495*m* are thus similarly configured and adapted to engage, grasp and capture at least defined, finite portions of soft tissue proximate the distal ends 474*b*, 473*b* of the top and bottom jaw members 462*a*, 462*b* within a confined surgical site when the soft tissue is advanced into the open jaw mechanism region 465 and/or jaw mechanism suture-tissue capture region 465' defined by the top and bottom jaw members 462*a*, 462*b* of the multi-function jaw mechanism 460*f* and the multi-function jaw mechanism 460*f* transitions to and is in the closed jaw configuration illustrated in FIG. 31B.

In a preferred embodiment, the distal ends 474*b*, 473*b* of the top and bottom jaw members 462*a*, 462*b* and hence, top and bottom tissue engaging surfaces 495*k*, 495*m* are similarly also configured and adapted to engage, grasp and capture surgical instruments and devices proximate the distal ends 474*b*, 473*b* of the top and bottom jaw members 462*a*, 462*b* when the surgical instruments and devices are advanced into the open jaw mechanism region 465 and/or jaw mechanism suture-tissue capture region 465' defined by the top and bottom jaw members 462*a*, 462*b* of the multi-function jaw mechanism 460*f* and the multi-function jaw mechanism 460*f* transitions to and is in the closed jaw configuration illustrated in FIG. 31B.

As indicated above, in a preferred embodiment, the top and bottom jaw member suture engaging surfaces 495€, 495*n* comprise smooth planar surfaces to facilitate engaging, grasping and capturing finite portions of sutures and soft tissue.

As also indicated above and illustrated in FIG. 31B, when the multi-function jaw mechanism 460*f* is in the closed jaw configuration, at least the top and bottom suture engaging regions 491*h*''', 491*i*''' and, hence, top and bottom jaw member suture engaging surfaces 495€, 495*n* are in contact.

Thus, in a preferred embodiment, when the multi-function jaw mechanism 460*f* transitions to and is in a closed jaw configuration, as illustrated in FIG. 31B, the top and bottom suture engaging regions 491*h*''', 491*i*''' of the top and bottom jaw members 462*a*, 462*b* will similarly engage, grasp and capture at least sutures within a confined surgical site when the sutures are advanced into the open jaw mechanism region 465 and/or jaw mechanism suture-tissue capture region 465' defined by the top and bottom jaw members 462*a*, 462*b* of the jaw mechanism 460*f* and the multi-function jaw mechanism 460*f* transitions to and is in the closed jaw configuration illustrated in FIG. 31B.

Referring back to FIGS. 26C-26E and indicated above, in a preferred embodiment, the raised distal guide regions 475*a*, 475*b*, 475*c* of the bottom jaw member 462*b* comprise a distal tissue guide region 477, which is sized and configured to position the portion of soft tissue in the tissue capture region 471 when the portion of the soft tissue is advanced therein.

In a preferred embodiment, systems of the invention employing the multi-function jaw mechanisms, i.e., multi-function jaw mechanisms 460*b*, 460*c*, 460*d*, 460*e*, 460*f* described above similarly comprise (i) a jaw articulation control system that is adapted to modulate articulation of the multi-function jaw mechanisms, (ii) a needle articulation control system that is adapted to modulate articulation of needle 170, and (iii) a suture control system that is adapted to modulate engagement, retainment and release of suture 170.

Preferred jaw articulation control systems, needle articulation control systems and suture control systems are described in detail in Applicant's priority U.S. application Ser. No. 18/623,903, now U.S. Pat. No. 12,390,213, which is expressly incorporated herein in its entirety.

In a preferred embodiment, the suture passing systems also comprise a multi-function actuation system that is configured to control the jaw articulation control system, needle articulation control system and suture control system.

Preferred multi-function actuation systems similarly comprise the multi-function actuation systems (denoted "405" and "505") that are described in detail in U.S. application Ser. No. 18/623,903.

According to the invention, control of the multi-function jaw mechanisms of the invention, needle 170 and suture engagement, retainment and release by the suture passing systems of the invention can also be provided via robotic systems.

By way of example, in some embodiments, a robotic system comprises at least one robotic interface or manipulator configured and adapted to interface with a suture passing system of the invention, such as suture passing system 400, and, hence, the multi-function jaw mechanisms, and a control system comprising programming means and associated algorithms adapted to control the robotic interface, whereby, at least the following synchronized functions are provided: axial articulation of the multi-function jaw mechanisms, needle articulation, and suture control, including access of suture into the open internal jaw region of multi-function jaw mechanisms, releasable engagement of the suture by the needle, and release of the suture by the needle.

According to the invention, the suture passing systems of the invention can also be adapted and configured to operate in conjunction with commercial robotic surgical systems, such as the da Vinci surgical systems (Intuitive Surgical), Hugo robotic-assisted surgery systems (Medtronic), and Versius surgical systems (CMR Surgical).

Figure 27B:
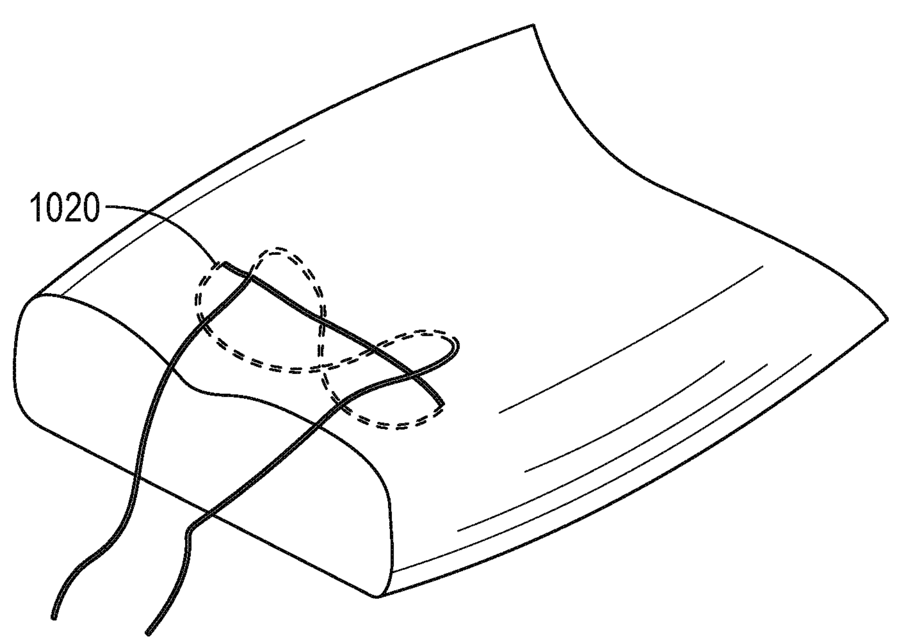
FIG. 27B is an illustration of a modified Mason-Allen stitch pattern.

As indicated above, an additional surgical function and, hence, feature of the multi-function jaw mechanisms of the invention comprises means for measuring stitch placement positions in soft tissue for accurate and precise provision of complex stitch patterns, such as the modified Mason-Allen stitch pattern illustrated in FIG. 27B.

Referring to FIG. 26A, in some embodiments, the means for measuring stitch placement positions in soft tissue comprises a first plurality of markers 485*a* disposed on a lateral side 463*c* or 463*d* of the bottom jaw member 462*b* that are defined distances from the suture loading slot 472 and, hence, needle engagement and stitch point referenced above.

In some embodiments, the means for measuring stitch placement positions in soft tissue further comprises a second plurality of markers 485*b* disposed on an opposing lateral side 463*a* or 463*b* of the top jaw member 462*a*, wherein the first and second plurality of markers 485*a*, 485*b* are aligned when the multi-function jaw mechanism 460*b* is in a closed configuration.

In a preferred embodiment, the first plurality of markers 485*a* is disposed on both lateral sides, i.e., lateral sides 463*c* and 463*d*, of the bottom jaw member 462*b* and the second plurality of markers 485*b* is disposed on both lateral sides, i.e., lateral sides 463*a* or 463*b*, of the top jaw member 462*a*, the first and second plurality of markers 485*a*, 485*b* being similarly aligned when the multi-function jaw mechanism 460*b* is in a closed configuration.

According to the invention, the distance from a border of soft tissue captured in the open jaw mechanism region 465 to a desired stitch position in the soft tissue, e.g., "$d_2$" in FIG. 26B, can be determined and realized by advancing the border of the soft tissue into the open jaw mechanism region 465 of the jaw mechanism 460*b* and aligning the border of the soft tissue with a desired marker of the first or second plurality of markers 485*a*, 485*b*.

According to the invention, the markers 485*a*, 485*b* can comprise any suitable form, such as printed markers, engraved markers, radiopaque markers, and any combination thereof, e.g., printed and engraved markers.

As will be readily appreciated by one having ordinary skill in the art, the multi-function jaw mechanisms of the invention, i.e., multi-function jaw mechanisms 460*b*, 460*c*, 460*d*, 460*e*, 460*f*, thus facilitate multiple seminal surgical functions, including highly effective and efficient means for (i) uncomplicated and highly reliable suture loading with minimal visual guidance, (ii) optimal suture manipulation and retrieval in soft tissue in a confined surgical site, (iii)

stitch placement measurement and positions in soft tissue in a confined surgical site for accurate and precise provision of complex stitch patterns, such as modified Mason-Allen stitch patterns, and (iv) grasping, engaging and capturing soft tissue, suture and surgical instruments (and devices) in a confined surgical site with minimal visual guidance.

The suture passing systems of the invention employing the multi-function jaw mechanisms of the invention thus obviate the need for various multiple surgical instruments, such as tissue graspers and suture retrievers, which are typically employed during a surgical procedure.

As further indicated above, additional features and advantages of the multi-function jaw mechanisms comprise (i) unique needle wear resistance means that increases the durability and longevity of a needle employed with the jaw mechanism 460*b* and (ii) needle protection means that prevents breakage of the needle 170; particularly, the needle tip (or suture ensnarement end 171), when subjected to high strain.

Referring now to FIG. 26X, in a preferred embodiment, the needle wear resistance means comprises two (2) wear resistance members that are positioned and configured to abut the outer surface of the needle employed within the multi-function jaw mechanisms, in this instance, needle 170, at defined needle abutment points (denoted $AP_1$, $AP_2$ in FIG. 26X) when the needle 170 is slidably translated through the needle guide channel 478.

As illustrated in FIG. 26X, in a preferred embodiment, a first wear resistance member 484 is disposed proximate the distal end 473*b* of the bottom jaw member 462*b*, i.e., at needle abutment point $AP_1$, and a second wear resistance member 486 is disposed on the bottom surface of the bottom jaw member 462*b* proximate the proximal end 473*a* thereof and transects the bottom jaw member window 470*b*, i.e., at needle abutment point $AP_2$.

According to the invention, the first and second wear resistance members 484, 486 can comprise any suitable size and shape. As illustrated in FIGS. 26X and 26Y1, in a preferred embodiment, the first wear resistance member 484 comprises a cylindrical-shaped pin member, which, as discussed below, preferably comprises a metal or metal alloy subjected to a cold-working process that enhances hardening of at least the surface region 487*a* and, thereby wear resistance and friction reduction of the wear resistance "pin" member 484.

As illustrated in FIGS. 26X and 26Y2, in a preferred embodiment, the second wear resistance member 486 comprises a partial cylindrical-shaped structure. In a preferred embodiment, the second wear resistance member 486 is formed from a cylindrical-shaped pin structure, which has similarly been subjected to a cold-working process that enhances hardening of the surface region.

As further illustrated in FIGS. 26X and 26Y2, after the cylindrical-shaped pin structure is subjected to the cold-working process, the cylindrical-shaped pin structure is further fabricated to form the illustrated partial cylindrical-shaped structure to minimize the profile size, while the critical work hardened surface 487*b*, which will interface with the needle 170, remains intact.

Figure 26Z:
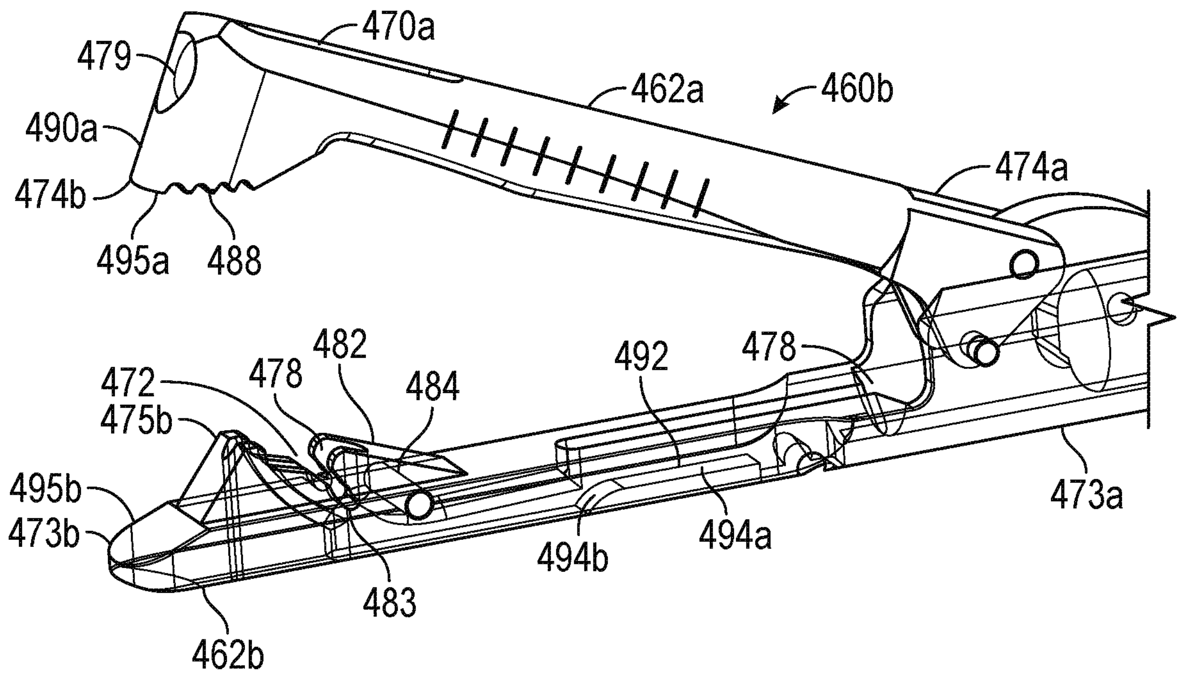
FIG. 26Z is a side perspective view of the multi-function jaw mechanism shown in FIG. 26A, showing the distal wear resistance member shown in FIG. 26Y1 and a further embodiment of a second wear resistance member positioned in the lower jaw mechanism of the multi-function jaw mechanism, in accordance with the invention.

Referring now to FIG. 26Z, in some embodiments, the second wear resistance member (now denoted "492") comprises a wedge-shaped insert member comprising a top needle abutment surface 494*a*. In a preferred embodiment of the invention, the "wedge-shaped" wear resistance member 492 is similarly comprises a cold-worked metal or metal alloy, i.e., a surface hardened sheet.

According to the invention, the "wedge-shaped" wear resistance member 492 can also be subjected to a forming process to form the rounded distal end 494*b*, and a subsequent process to minimize the profile size with the hardened surface remaining intact and providing enhanced wear resistance and friction reduction.

As indicated above, in a preferred embodiment, the wear resistance members 484, 486, 492 comprise a metal or metal alloy subjected to a cold-working process, i.e., a work-hardened metal or metal alloy, that enhances hardening and, thereby wear resistance and friction reduction of the wear resistance members 484, 486, 492; particularly, the surfaces thereof.

According to the invention, suitable metals and metal alloys include, without limitation, stainless steel and alloys thereof, particularly, nitrogen-strengthened (austenitic) stainless-steel alloys (e.g., Nitronic 60 and Nitronic 30), nickel-chromium-iron alloys (e.g., Inconel 625) and cobalt-chromium-nickel alloys (e.g., Elgaloy 60).

In a preferred embodiment, the wear resistance members 484, 486, 492 comprise cold-worked Nitronic 60 or Elgaloy 60.

According to the invention, the wear resistance members 484, 486, 492 can also comprise various polymeric materials comprising low wear rates and/or coefficients of friction, such as, without limitation, acetal, nylon, ultra-high molecular weight polyethylene (UHMW-PE), polyphenylene sulfide (PPS), polyether ether ketone (PEEK) and polyamide-imide (PAI).

According to the invention, to further enhance wear resistance of the wear resistance members 484, 486, 492 and, hence, durability and longevity of a needle employed with the multi-function jaw mechanisms of the invention, the wear resistance members 484, 486, 492 can further comprise a surface coating that further lowers the coefficient of friction and, hence, wear rate.

According to the invention, suitable friction abatement coatings comprise, without limitation, diamond-like carbon (DLC) materials, graphene-based coatings, synthetic fluoropolymers and combinations thereof.

According to the invention, other components of the suture passing systems of the invention, such as needle 170 and surfaces of needle guide channel 478, can also comprise one or more of the aforementioned friction abatement coatings.

According to the invention, components of the suture passing systems of the invention, such as top and bottom jaw members 462*a*, 462*b*, can also comprise an anti-reflective coating, e.g., a cerium oxide ($CeO_2$) or $CeO_2$-based coating, to prevent glare, such as arthroscope glare, during a surgical procedure to facilitate visualization within a surgical site.

According to the invention, the outer coatings can also comprise various pharmaceutical agents, including, without limitation, antibiotics, anti-microbial agents, anti-viral agents, analgesic agents, anti-inflammatory agents, anti-neoplastic agents, anti-spasmodic agents, anticoagulant agents and agents that modulate proliferation and growth of tissue.

As indicated above, an additional feature and advantage of the multi-function jaw mechanisms of the invention comprises needle protection means that prevents breakage of the needle when subjected to high strain during a surgical procedure.

According to the invention, the needle protection means is provided via the uniquely configured needle guide channel 478.

Referring back to FIG. 26X, in a preferred embodiment, when slidable translation of the needle 170 is induced through the guide channel 478 and the suture ensnarement end 171 of the needle 170 abuts a semi-penetrable or impenetrable object, the "open" needle guide channel 478 allows needle 170 to flex (or bend) at abutment points $AP_1$, $AP_2$ and, hence, prevent fracture and/or breakage of the needle 170 at the suture ensnarement end 171, and thus prevent small fragments of the needle 170 from being introduced into the surgical site.

An additional feature of the multi-function jaw mechanisms of the invention is that the multi-function jaw mechanisms are readily adapted to receive and advance virtually all conventional sutures into and through various soft tissues and soft tissue structures, including, without limitation, the HS-Fiber Suture Implants developed by Tensor Surgical, Inc. (NV) and various additional sutures comprising biodegradable polymers; particularly, poly(glycerol sebacate) (PGS) and derivatives thereof, such as poly(glycerol-co-sebacate) acrylate (PGSA).

As set forth in Yu, et al., *Development of Poly (Glycerol Sebacate) and its Derivatives: A Review of the Progress Over the Past Two Decades*, Polymer Reviews, vol. 63, no. 3, pp. 613-678 (2023) and Wu, et al., *A Review: Optimization for Poly (Glycerol Sebacate) and Fabrication Techniques for its Centered Scaffolds*, Macromolecular Bioscience, vol. 21, no. 9, pg. 2100022 (2021), PGS and derivatives thereof possess a plurality of unique structural and chemical properties, whereby PGS and its derivatives induce remodeling of damaged soft tissue and bone tissue and structures, and, hence, healing thereof, when disposed proximate thereto.

As will readily be appreciated by one having ordinary skill in the art, the suture passing systems, apparatus and methods of the invention thus provide numerous advantages compared to prior art systems, apparatus and methods for passing suture through soft tissue and soft tissue structures. Among the advantages are the following:

- The provision of highly reliable suture passing systems, apparatus and associated methods that can be readily employed to effectively approximate, ligate, fixate soft tissue and soft tissue structures and/or close soft tissue structures;
- The provision of suture passing systems, apparatus and associated methods that can be readily employed to pass suture into and through soft tissue and soft tissue structures without collateral damage to extraneous soft tissue and bone structures;
- The provision of suture passing systems, apparatus and associated methods that provide an enhanced degree of control of soft tissue and soft tissue structure engagement, needle articulation and suture manipulation by an operator with minimal complexity;
- The provision of suture passing systems, apparatus and associated methods that enable an operator to load suture with greater ease and efficiency compared to conventional suture passing systems;
- The provision of suture passing systems, apparatus and associated methods that provide enhanced suture manipulation in a confined surgical site with minimal visual guidance;
- The provision of suture passing systems, apparatus and associated methods that enable an operator to precisely measure stitch placement locations in soft tissue and soft tissue structures in a confined surgical site for accurate and precise provision of complex stitch patterns, such as modified Mason-Allen stitch patterns;
- The provision of suture passing systems, apparatus and associated methods that can be readily employed to effectively capture and engage soft tissue, soft tissue structures and surgical instruments within a confined surgical site;
- The provision of suture passing systems, apparatus and associated methods that provide enhanced needle durability over thousands of cycles of suture passing in and through soft tissue and soft tissue structures;
- The provision of suture passing systems and apparatus that can be readily employed to endure multiple use cycles with limited impact on suture passing efficacy;
- The provision of suture passing systems, apparatus and associated methods that prevent needle breakage in a surgical site during a surgical procedure; and
- The provision of multi-function jaw mechanisms and suture passing systems, apparatus and associated methods employing the multi-function jaw mechanisms, which (i) enable an operator to load suture with greater ease and efficiency compared to conventional suture passing systems, and (ii) provide enhanced suture manipulation and retrieval in a confined surgical site with minimal visual guidance, and (iii) enable an operator to precisely measure stitch placement locations in soft tissue and soft tissue structures in a confined surgical site for accurate and precise provision of complex stitch patterns, such as modified Mason-Allen stitch patterns, and (iv) can be readily employed to effectively capture and engage soft tissue, soft tissue structures and surgical instruments within a confined surgical site, and (v) provide enhanced needle durability over thousands of cycles of antegrade and retrograde passing of suture, and (vi) prevent needle breakage in a surgical site during a surgical procedure.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A system for grasping, approximating and fixating soft tissue, comprising:

a needle comprising a tissue piercing distal end configured and adapted to releasably engage a suture and pierce into and through soft tissue with said suture said releasably engaged thereto; and a multi-function jaw mechanism adapted to receive and cooperate with said needle, wherein said needle is allowed to linearly articulate with respect to said jaw mechanism, said multi-function jaw mechanism comprising top and bottom jaw members, said top jaw member adapted to axially articulate with respect to said bottom jaw member, whereby said multi-function jaw mechanism is adapted to transition from a fully open jaw configuration, wherein said top and bottom jaw members provide an open jaw mechanism region, to a closed jaw configuration, said open jaw mechanism region configured to receive a suture and at least first soft tissue therein, said multi-function jaw mechanism further adapted to transition to a partially open jaw configuration from said fully open jaw configuration and said closed jaw configuration, said partially open jaw configuration similarly configured to said receive said suture and said at least first soft tissue therein, said top jaw member comprising a top jaw member longitudinal axis, a top jaw member proximal end and a top jaw member distal end, said bottom jaw member comprising a bottom jaw member proximal end and a bottom jaw member distal end, said top jaw member distal end disposed proximate said bottom jaw member distal end when said multi-function jaw mechanism is in said closed jaw configuration, said top jaw member distal end comprising a first suture-tissue engagement region, said first suture-tissue engagement region comprising a top jaw member tissue engagement region, a top jaw member suture engagement region and a recessed region disposed between said top jaw member tissue engagement region and said top jaw member suture engagement region, said top jaw member suture engagement region extending proximally from said top jaw member distal end no greater than 4.0 mm, said top jaw member tissue engagement region comprising a first tissue engaging surface adapted to grasp second soft tissue, said top jaw member suture engagement region comprising a first suture engaging surface adapted to removably engage said suture, said bottom jaw member distal end comprising a second suture-tissue engagement region, said second suture-tissue engagement region comprising a bottom jaw member tissue engagement region and a bottom jaw member suture engagement region, said bottom jaw member tissue engagement region comprising a second tissue engaging surface adapted to grasp said second soft tissue, said bottom jaw member suture engagement region comprising a second suture engaging surface adapted to removably engage said suture, said first suture-tissue engagement region of said top jaw member positioned relative to said second suture-tissue engagement region of said bottom jaw member, whereby, when said multi-function jaw mechanism is in said closed jaw configuration, said first suture-tissue engagement region of said top jaw member and said second suture-tissue engagement region of said bottom jaw member are aligned and form a jaw mechanism suture-tissue engagement region, wherein at least said top jaw member suture engagement region and said bottom jaw member suture engagement region are in contact, said first suture-tissue engagement region of said top jaw member and said second suture-tissue engagement region of said bottom jaw member further forming a jaw mechanism suture-tissue capture region when said multi-function jaw mechanism is in said partially open jaw configuration, wherein, when said suture is received in said jaw mechanism suture-tissue capture region and said multi-function jaw mechanism is in said closed jaw configuration, said top jaw member suture engagement region and said bottom jaw member suture engagement region jointly grasp and retain said suture in said jaw mechanism suture-tissue engagement region.

2. The system of claim 1, wherein, when said suture is received in said open jaw mechanism region said provided by said multi-function jaw mechanism and said multi-function jaw mechanism is in said closed jaw configuration, said top jaw member suture engagement region and said bottom jaw member suture engagement region jointly grasp and retain said suture in said jaw mechanism suture-tissue engagement region.

3. The system of claim 1, wherein, when said second soft tissue is received in said open jaw mechanism region said provided by said multi-function jaw mechanism or said jaw mechanism suture-tissue capture region and said multi-function jaw mechanism is in said closed jaw configuration, said top jaw member tissue engagement region and said bottom jaw member tissue engagement region jointly grasp and retain at least a portion of said second soft tissue in said jaw mechanism suture-tissue engagement region.

4. The system of claim 1, wherein said top jaw member suture engagement region comprises a width no greater than about 4.0 mm.

5. The system of claim 1, wherein said top jaw member comprises a first jaw member length that extends from said top jaw member proximal end to said top jaw member distal end, and said bottom jaw member comprising a second jaw member length that extends from said bottom jaw member proximal end to said bottom jaw member distal end.

6. The system of claim 5, wherein said jaw mechanism suture-tissue engagement region extends proximally less than 20% of said first jaw member length and less than 20% of said second jaw member length when said multi-function jaw mechanism is in said closed jaw configuration.

7. The system of claim 6, wherein said first suture-tissue engagement region of said top jaw member comprises a third jaw member length from said top jaw member distal end no greater than 12.0 mm.

8. The system of claim 6, wherein said second suture-tissue engagement region of said bottom jaw member comprises a fourth jaw member length from said bottom jaw member distal end no greater than 12.0 mm.

9. The system of claim 1, wherein said top jaw member suture engagement region comprises a planar structure that extends distally from said top jaw member tissue engagement region.

10. The system of claim 9, wherein said planar structure of said top jaw member suture engagement region defines a longitudinal plane that is parallel to said top jaw member longitudinal axis.

11. The system of claim 1, wherein said first tissue engaging surface of said top jaw member comprises a first serrated surface and said second tissue engaging surface of said bottom jaw member comprises a corresponding second serrated surface.

12. The system of claim 1, wherein said first suture-tissue engagement region of said top jaw member defines a linear plane.

13. The system of claim 1, wherein said first suture-tissue engagement region of said top jaw member defines first and second linear planes, said first linear plane defined by said top jaw member tissue engagement region, said second linear plane defined by said top jaw member suture engagement region.

14. The system of claim 1, wherein said first tissue engaging surface of said top jaw member and said second tissue engaging surface of said bottom jaw member are further adapted to grasp a surgical device.

15. The system of claim 14, wherein said surgical device is selected from the group consisting of tissue graspers and suture retrievers.

16. The system of claim 14, wherein, when said surgical device is received in said open jaw mechanism region said provided by said multi-function jaw mechanism or said jaw mechanism suture-tissue capture region and said multi-function jaw mechanism is in said closed jaw configuration, said top jaw member tissue engagement region and said bottom jaw member tissue engagement region jointly engage and retain said surgical device in said jaw mechanism suture-tissue engagement region.

17. The system of claim 1, wherein said first suture-tissue engagement region only comprises said top jaw member tissue engagement region and said top jaw member suture engagement region.

18. The system of claim 1, wherein said jaw mechanism suture-tissue engagement region comprises a jaw mechanism suture-tissue engagement region proximal end and a jaw mechanism suture-tissue engagement region distal end.

19. The system of claim 18, wherein said bottom jaw member further comprises a suture engagement region comprising a raised proximal guide region, a raised distal guide region, and a suture loading slot disposed between said raised proximal guide region and said raised distal guide region, said suture loading slot sized and configured to receive said suture therein.

20. The system of claim 19, wherein said raised distal guide region of said suture engagement region is disposed proximate said jaw mechanism suture-tissue engagement region proximal end.

21. The system of claim 20, wherein said raised distal guide region of said suture engagement region comprises a distal suture-tissue abatement region and a first proximal suture guide region.

22. The system of claim 21, wherein said distal suture-tissue abatement region of said raised distal guide region is positioned and configured to abate proximal translation of said suture and said second soft tissue past said raised distal guide region when said suture and said second soft tissue are said received in said jaw mechanism suture-tissue capture region.

23. The system of claim 21, wherein said first proximal suture guide region of said raised distal guide region is positioned and configured to guide said suture into said suture loading slot when said suture is said received in said suture engagement region.

24. The system of claim 21, wherein said raised proximal guide region comprises a second proximal suture guide region and a distal suture guide region.

25. The system of claim 24, wherein said distal suture guide region of said raised proximal guide region is positioned and configured to further guide said suture into said suture loading slot when said suture is said received in said suture engagement region.

26. The system of claim 25, wherein said first proximal suture guide region of said raised distal guide region comprises a first continuous outer edge and an opposing second continuous outer edge, said second proximal suture guide region of said raised proximal guide region comprises a third continuous outer edge and an opposing fourth continuous outer edge, and said distal suture guide region of said raised proximal guide region comprises a fifth continuous outer edge and an opposing sixth continuous outer edge, said first, second, third, fourth, fifth and sixth continuous outer edges comprising rounded configurations configured to abate disruption of said receipt of said suture into said suture engagement region and said suture loading slot.

27. The system of claim 1, wherein said multi-function jaw mechanism further comprises a retractable suture control ribbon adapted to control access of said suture into said open jaw mechanism region of said multi-function jaw mechanism and said releasable engagement of said suture by said needle.

28. The system of claim 27, wherein said system further comprises system control means for synchronizing said axial articulation of said top jaw member, said linear articulation of said needle, said access of said suture into said open jaw mechanism region of said multi-function jaw mechanism and said releasable engagement of said suture by said needle.

* * * * *